US008389234B2

(12) United States Patent
Yang-Woytowitz et al.

(10) Patent No.: US 8,389,234 B2
(45) Date of Patent: Mar. 5, 2013

(54) KITS FOR THE DETECTION OF BETA-LACTAMASES

(75) Inventors: Mei Yang-Woytowitz, Baltimore, MD (US); Charles Yu, Lutherville, MD (US); Timothy Wiles, Manchester, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/307,426

(22) Filed: Nov. 30, 2011

(65) Prior Publication Data

US 2012/0077215 A1 Mar. 29, 2012

Related U.S. Application Data

(62) Division of application No. 12/254,594, filed on Oct. 20, 2008, now Pat. No. 8,097,434.

(60) Provisional application No. 60/981,156, filed on Oct. 19, 2007.

(51) Int. Cl.
C12Q 1/04 (2006.01)

(52) U.S. Cl. .............................. 435/34; 435/32; 435/975

(58) Field of Classification Search .................... 435/34, 435/32, 975
See application file for complete search history.

(56) References Cited

U.S. PATENT DOCUMENTS

| | | | |
|---|---|---|---|
| 4,712,310 A | 12/1987 | Roy | |
| 4,740,459 A | 4/1988 | Chen et al. | |
| 4,891,319 A | 1/1990 | Roser | |
| 4,965,193 A | 10/1990 | Chen | |
| 5,338,843 A | 8/1994 | Quante et al. | |
| 5,514,561 A | 5/1996 | Quante et al. | |
| 5,516,902 A | 5/1996 | Quante et al. | |
| 5,583,217 A | 12/1996 | Quante et al. | |
| 5,741,657 A | 4/1998 | Tsien et al. | |
| 5,776,563 A | 7/1998 | Buhi et al. | |
| 5,922,593 A | 7/1999 | Livingston | |
| 5,955,351 A | 9/1999 | Gerdes et al. | |
| 5,955,604 A | 9/1999 | Tsien et al. | |
| D421,498 S | 3/2000 | Livingston | |
| 6,043,048 A | 3/2000 | Johnston et al. | |
| 6,075,014 A | 6/2000 | Weston et al. | |
| 6,096,272 A | 8/2000 | Clark et al. | |
| 6,372,485 B1 | 4/2002 | Clark et al. | |
| 6,472,205 B1 | 10/2002 | Tsien et al. | |
| 6,849,422 B1 | 2/2005 | Wiles et al. | |
| 6,897,304 B2 | 5/2005 | Kawashima et al. | |
| 7,115,384 B2 | 10/2006 | Clark et al. | |
| 7,250,152 B2 | 7/2007 | Gentile et al. | |
| 8,097,434 B2 * | 1/2012 | Yang-Woytowitz et al. ... | 435/34 |
| 2002/0115642 A1 | 8/2002 | Chan et al. | |
| 2003/0119042 A1 | 6/2003 | Franco De Sarabia Rosado et al. | |
| 2004/0115756 A1 | 6/2004 | Black et al. | |
| 2005/0089947 A1 | 4/2005 | Black et al. | |
| 2005/0244917 A1 | 11/2005 | Black et al. | |
| 2005/0277170 A1 | 12/2005 | Black et al. | |
| 2006/0014230 A1 | 1/2006 | Murata | |
| 2007/0082376 A1 | 4/2007 | Black et al. | |
| 2011/0262957 A1 | 10/2011 | Yang-Woytowitz et al. | |

FOREIGN PATENT DOCUMENTS

| | | |
|---|---|---|
| GB | 2 093 994 A | 9/1982 |
| WO | WO 89/03889 | 5/1989 |
| WO | WO 92/19763 | 11/1992 |
| WO | WO 96/30540 | 10/1996 |
| WO | WO 03/041483 A2 | 5/2003 |
| WO | WO 03/078654 A1 | 9/2003 |
| WO | WO 2004/076054 A2 | 9/2004 |
| WO | WO 2005/040412 A1 | 5/2005 |
| WO | WO 2005/071096 A2 | 8/2005 |
| WO | WO 2006/031936 A2 | 3/2006 |
| WO | WO 2006/085978 A2 | 8/2006 |
| WO | WO 2006/119280 | 11/2006 |
| WO | WO 2006/121510 | 11/2006 |
| WO | WO 2009/051838 A1 | 4/2009 |
| WO | WO 2009/061864 | 5/2009 |
| WO | WO 2010/004778 | 1/2010 |
| WO | WO 2010/047778 A1 | 4/2010 |

OTHER PUBLICATIONS

Babini et al., 2000, "Effect of conalbumin on the activity of Syn 2190, a 1,5 dihydroxy-4-pyridon monobactam inhibitor of AmpC beta-lactamases , " J. of Antimicrob. Chemother., 45: 105-109.

Bebrone et al., Jun. 2001, "CENTA as a chromogenic substrate for studying beta-lactamases," Antimicrob. Agents & Chemo, 45(6): 1868-1871.

Birdsell et al., 1967, "Production and ultrastructure of lysozyme and ethylenediaminetetraacetate-lysozyme spheroplasts of *Escherichia coli*", Journal of Bacteriology; 93(1):427-437.

Boughton, Jun. 1982, "Rapid detection in spinal fluid of beta-lactamase produced by ampicillin-resistant *Haemophilus influenzae*," J. of Clinical Microbiol, 15(6): 1167-1168.

Bratu et al., Jun. 27, 2005, "Rapid spread of carbapenem-resistant *Klebsiella pneumoniae* in New York City: A new threat to our antibiotic armamentarium," Arch Intern Med, 165: 1430-1435.

Bush et al., 1995, "A Functional Classification Scheme for β-Lactamases and Its Correlation with Molecular Structure," Antimicrobial Agents and Chemotherapy 39(6): 1211-1233.

Colaco et al., Sep. 1992, "Extraordinary stability of enzymes dried in trehalose: simplified molecular biology," Bio/Technology, 10:1007-1011.

Connell et al., 1994, "Detection of beta lactamase in sputum," J. Clin Pathol, 47: 732-735.

(Continued)

Primary Examiner — Ralph Gitomer
(74) Attorney, Agent, or Firm — Jones Day

(57) ABSTRACT

Presented herein are kits for the detection of specific beta-lactamases, including class A serine carbapenemases, metallo-beta-lactamases, AmpC beta-lactamases, and extended-spectrum beta-lactamases (ESBLs). The kits presented herein include kits that permit the detection of the presence of specific beta-lactamases in bacterial samples within as few as 2 to 10 minutes.

20 Claims, No Drawings

OTHER PUBLICATIONS

Coudron, Aug. 2005, "Inhibitor-based methods for detection of plasmid-mediated AmpC beta-lactamases in *Klebsiella* spp., *Escherichia coli*, and *Proteus mirabilis*," J.Clin. Microbiol., 43(8): 4163-4167.
Database WPI Week 200505, AN 2005-045169 and RU 2240136: Thomson Scientific, London,GB.
Dirama et al., 2006, "Coupling between lysozyme and trehalose dynamics: microscopic insights from molecular-dynamics simulations," J Chem Phys., 124(3):034901.
Donay et al., Apr. 2004, "Evaluation of the automated phoenix system for potential routine use in the clinical microbiology laboratory," J. Clin. Microbiol., 42(4): 1542-1546.
Drawz et al., 2010, "Three Decades of β-Lactamase Inhibitors," Clinical Microbiology Reviews 23(1): 160-201.
Fiett et al., Mar. 2006, "Molecular epidemiology of acquired-metallo-beta-lactamase-producing bacteria in Poland," Antimicrob. Agents & Chemo., 50(3): 880-886.
Hanaki et al., Mar. 31, 2004, "Characterization of HMRZ-86: a novel chromogenic cephalosporin for the detection of extended-spectrum beta-lactamases," J. Antimicro. Chemo. Advance Access Pub., 888-889.
Hanson, 2003, "AmpC beta-lactamases: what do we need to know for the future," J. Antimicrob. Chemother., 52: 2-4.
Hedoux et al., 2006, "Analysis of sugar bioprotective mechanisms on the thermal denaturation of lysozyme from Raman scattering and differential scanning calorimetry investigations," J Phys Chem B. 110(45):22886-93.
International Search Report dated Jan. 19, 2009, issued in International Patent Application No. PCT/US2008/011934.
International Search Report of International application PCT/US2009/005701, dated Mar. 30, 2010.
Jacoby et al., Jan. 27, 2005, "The new beta-lactamases," The New England J. of Med., 352(4): 380-391.
Jamieson et al., May 2003, "In vitro and in vivo activities of AM-112, a novel oxapenem," Antimicro Agents & Chemo., 47(5): 1652-1657.
Jiang et al., Sep. 2006, "Detection of extended-spectrum beta-lactamases in clinical isolates of *Pseudomonas aeruginosa*," Antimicro Agents & Chemo., 50(9): 2990-2995.
Jones et al., May 1982, "In vitro evaluation of CENTA, a new beta-lactamase-susceptible chromogenic cephalosporin reagent," J. of Clinical Micro., 15(5): 954-958.
Jovanovic et al., 2004, "Stabilization of proteins in dry powder formulations using supercritical fluid technology," Pharm Res., 21(11):1955-1969.
Jovanovic et al., 2006, "Distinct effects of sucrose and trehalose on protein stability during supercritical fluid drying and freeze-drying," Eur J Pharm. Sci., 27(4):336-45.
Jovanovic et al., 2006, "Near-infrared imaging for studying homogeneity of protein-sugar mixtures," Pharm. Res., 23(9):2002-2013.
Jovanovic et al., 2008, "Stable sugar-based protein formulations by supercritical fluid drying," Intl J. Pharm., 346(1-2):102-8.
Kaushik et al., 2003, "Why is trehalose an exceptional protein stabilizer? An analysis of the thermal stability of proteins in the presence of the compatible osmolyte trehalose", J Biol Chem; 278(29):26458-26465.
Lerbret et al., 2007, "How do trehalose, maltose, and sucrose influence some structural and dynamical properties of lysozyme? Insight from molecular dynamics simulations," J Phys Chem. B., 111(31):9410-20.
Liao et al., 2002, "Effects of sucrose and trehalose on the preservation of the native structure of spray-dried lysozyme," Pharm Res., 19(12):1847-1853.
Liao et al., 2002, "Protective mechanism of stabilizing excipients against dehydration in the freeze-drying of proteins," Pharm Res., 19(12):1854-1861.
Liao et al., 2003, "Investigation of the physical properties of spray-dried stabilised lysozyme particles," J Pharm Pharmacol., 55(9):1213-21.
Liao et al., 2004, "Investigation of the stabilisation of freeze-dried lysozyme and the physical properties of the formulations," Eur J. Pharm Biopharm., 58(1):15-24.

Livermore et al., 2006, "The beta-lactamase threat in enterobacteriaceae, *Pseudomonas* and *Acinetobacter*," Trends in Microbiol, 14(9): 413-420.
Marchiaro et al., Nov. 2005, "Sensitive EDTA-based microbiological assays for detection of metallo-beta-lactamases in nonfermentative gram-negative bacteria," J. of Clinical Microbiol., 43(11): 5648-5652.
Martin et al., 1990, "Increase in the activity of third-generation cephalosporins in combination with clavulanic acid and Sulbactam™ against *Bacteroides fragilis*," Med Lab Sciences, 47: 163-167.
Martin et al., 1991, "A comparative study of the activity of first and second generation cephalosporins and their combinations with beta-lactamase inhibitors against *Bacteroides fragilis*," Microbios, 67: 195-202.
Miller et al., Oct. 2001, "Beta-lactamase-inhibitor combinations in the $21^{st}$ century current agents and new developments," Current Opinion of Pharmacology, 1(5): 451-458.
Moland et al., Sep. 2006, "Prevalence of newer beta-lactamases in gram-negative clinical isolates collected in the United States from 2001 to 2002," J. of Clinical Microbiol, 44(9): 3318-3324.
Notice of Allowance and Fees Due of U.S. Appl. No. 12/254,594, dated Sep. 1, 2011.
Nukaga, et al., Nov. 2003, "Inhibition of class A and class C beta-lactamases by penems: crystallographic structures of a novel 1,4-thiazepine intermediate," Biochem, 42: 13152-13159.
O'Callaghan et al., Apr. 1972, "Novel method for detection of beta-lactamases by using a chromogenic cephalosporin substrate," Antimicro Agents & Chemo, 1(4): 283-288.
Office Action of U.S. Appl. No. 12/254,594, dated Apr. 4, 2011—Non-Final Action.
Office Action of U.S. Appl. No. 12/254,594, dated Jan. 6, 2011—Restriction Requirement.
Papanicolaou et al., Nov. 1990, "Discrimination of extended-spectrum beta-lactamases by a novel nitrocefin competition assay," Antimicro Agents & Chemo, 34(11): 2184-2192.
Payne et al., May 1994, "Rapid identification of metallo- and serine beta-lactamases," Antimicro Agents & Chemo, 38(5): 991-996.
Petropoulou et al., 2006, "Evaluation of imipenem/imipenem+EDTA disk method for detection of metallo-beta-lactamase-producing *Klebsiella pneumoniae* isolated from blood cultures," Microbiol Drug Resistance, 12(1): 39-43.
Philippon et al., 2002, "Plasmid-determined AmpC-type beta-lactamases," Antimicrob. Agents Chemother, 46: 1-11.
Queenan et al., 2007, "Carbapenemases: the versatile beta-lactamases," Clinical Microbiology Review, 20(3): 440-458.
Ramachandran et al., 2006, "Dry-reagent storage for disposable tab-on-a-card diagnosis of enteric pathogens", Proceedings of the $1^{st}$ Distributed Diagnosis and Home Healthcare (D2H2) Conference; Arlington, Virginia.
Rasheed et al., 2000, "Characterization of the extended-spectrum beta-lactamase reference strain, *Klebsiella pneumoniae* K6 (ATCC 700603), which produces the novel enzyme SHV-18," Antimicrob. Agents Chem. Ther. 44: 2382-2388.
Reig et al., 1991, "[Characterization of *Haemophilus influenzae's* resistance to ampicillin ]," Med Clin (Barc), 96: 727-729.
Response to Non-Final Office Action mailed Apr. 4, 2011 of U.S. Appl. No. 12/254,594, dated Aug. 4, 2011.
Response to Restriction Requirement and Preliminary Amendment of U.S. Appl. No. 12/254,594, dated Feb. 7, 2011.
Sanders et al., 1986, "Characterization of beta-lactamases in situ on polyacrylamide gels," Antimicro Agents & Chemo., 30(6): 951-952.
Shannon et al., 1980, "Beta-lactamase detection by three simple methods: Intralactam, nitrocefin and acidimetric," J. Antimicrobiol Chemo., 6: 617-621.
Sharma et al., 2004, "Detection and assay of beta lactamases in clinical and non-clinical strains of *Yersinia enterocolitica* biovar IA", J Antimicrobial Chemotherapy; 54(2):401-105.
Singh et al., 2003, "Effect of polyols on the conformational stability and biological activity of a model protein lysozyme," AAPS PharmSciTech, 4(3) Article 42, pp. 1-9 (http://www.pharmscitech.org.).

Thomson et al., 2006, "Comparison of phoenix and vitek 2 ESBL confirmatory tests against *E. coli* and *Klebsiella* isolates with well-characterized beta-lactamases," 106th General Meeting of the American Society for Microbiology, Orlando, FL 2006.

Turner et al., 2000, "Detection of ESBL producing *E. coli* and *Klebsiella* in the Phoenix™ automated microbiology system," 10th European Congress of Clinical Microbiology & Infectious Diseases, May 2000.

URI, 1985, "Detection of beta-lactamase activity with nitrocefin of multiple strains of various microbial genera," Acta Micro Hungarica, 32(2): 133-145.

Walsh et al., 2005, "Metallo-beta-lactamases: the quiet before the storm?" Clinical Microbiol Reviews, 18( 2): 306-325.

Walsh, 2005, "The emergence and implications of metallo-beta-lactamases in Gram-negative bacteria," Clinical Microbiol & Infect. Disc., 11(Supp. 6): 2-9.

Written Opinion of International application PCT/US2008/011934, dated Oct. 19, 2007.

Written Opinion of International application PCT/US2009/005701, dated Mar. 30, 2010.

Yigit et al., 2001, "Novel carbapenem-hydrolyzing beta-lactamase, KPC-1, from a carbapenem-resistant strain of *Klebsiella pneumoniae*," Antimicrob. Agents Chemother., 45: 1151-1161.

Yigit et al., 2003, "Carbapenem-resistant strain of *Klebsiella oxytoca* harboring carbapenem-hydrolyzing beta-lactamase KPC-2," Antimicrob. Agents & Chemother., 47: 3881-3889.

Yong et al., May 2006, "Increasing prevalence and diversity of metallo-beta-lactamases in *Pseudomonas* spp., *Acinetobacter* spp., and *Enterobacteriaceae* from Korea," Antimicro Agents & Chemo, 50(5): 1884-1886.

Yu et al., 1999, "Rapid detection of beta-lactamase production in penicillin sensitive *Staphylococci* by the phoenix™ automated ID/AST system," 9th European Congress of Clinical Microbiology & Infection Disease, Berlin, Germany, Mar. 1999.

Office Action of U.S. Appl. No. 12/257,594, dated Dec. 7, 2011—IDS Considered.

Papanicolaou et al., Nov. 1990, "Discrimination of extended-spectrum beta-lactamases by a novel nitrocefin competition assay," Antimiero Agents & Chemo, 34(11): 2184-2192.

\* cited by examiner

KITS FOR THE DETECTION OF BETA-LACTAMASES

This application is a divisional of U.S. patent application Ser. No. 12/254,594, filed Oct. 20, 2008, now U.S. Pat. No. 8,097,434, which claims priority under 35 U.S.C. §119(e) to U.S. provisional application Ser. No. 60/981,156, filed Oct. 19, 2007, each of which is incorporated herein by reference in its entirety.

1. INTRODUCTION

Presented herein are methods and compositions for the detection of specific beta-lactamases, including class A serine carbapenemases, metallo-beta-lactamases, AmpC beta-lactamases, and extended-spectrum beta-lactamases (ESBLs). The methods presented herein include methods that permit the detection of the presence of specific beta-lactamases in bacterial samples within as few as 2 to 10 minutes.

2. BACKGROUND

Beta-lactamases are a family of enzymes that hydrolyze beta-lactam rings, such as beta-lactam rings of beta-lactam antibiotic drugs. Beta-lactamases are found in gram positive and gram negative bacteria and are responsible for the antibiotic resistance of many bacterial strains.

Beta-lactamases can be classified on the basis of their primary structure into four molecular classes, namely classes A to D. Classes A, C and D have a serine residue at their active site and class B, or metallo-beta-lactamases, have zinc at their active site. Carbapenemases are a diverse group of beta-lactamases that include enzymes belonging to class A, B and D. Class A carbapenemases include KPC-1, KPC-2, KPC-3 and KPC-4. Class B carbapenemases include the IMP family, VIM family, GIM-1 and SPM-1 as well as others. Class D carbapenemases include OXA-23, OXA-24, OXA-25, OXA-26, OXA-27, OXA-40 and OXA-40 as well as others. AmpC beta-lactamases are class C enzymes and can be encoded by chromosomal genes or be plasmid-borne. AmpC beta-lactamases hydrolyze broad and extended-spectrum cephalosporins cephamycins and oxyimino-beta-lactams). Extended-spectrum beta-lactamases (ESBLs) are beta-lactamases that hydrolyze cephalosporins with an oxyimino chain. ESBLs include the TEM family, SHV family as well as others, and CTX-M family, which are class A enzymes. Original-spectrum beta-lactamases (OSBLs) include class A enzymes.

The spread of beta-lactamases between bacteria has increased the resistance of bacteria to beta-lactam drugs. The administration of beta-lactam drugs to patients with bacteria resistant to those drugs selects for those bacteria and leads to an increase in the transmission of beta-lactamases. Thus, there is a need to rapidly detect bacteria expressing specific beta-lactamases so that an appropriate therapeutic regimen is selected for a given patient and the likelihood of the spread of resistant bacteria is reduced.

3. SUMMARY

In one aspect, presented herein are methods for the rapid detection of particular beta-lactamases using a detectable beta-lactamase substrate and certain beta-lactamase inhibitors. For example, presented herein are methods for the rapid detection of serine carbapenemases, metallo-beta-lactamases, AmpC, and extended-spectrum beta-lactamases (ESBLs). Some methods presented herein do not require the production of a bacterial cell extract and some methods presented herein only require a small amount of a bacterial sample (e.g., less than $10^{10}$ CFU or less than $10^{8}$ CFU of bacteria). Further, methods presented herein permit the detection of the presence of such beta-lactamases in bacterial samples within as few as 2 to 10 minutes. Detection of the presence of the beta-lactamases can provide information for the selection of the appropriate therapeutic regimen for a patient with a bacterial infection.

The methods presented herein can comprise: (a) contacting two or more bacterial samples from the same source with different compositions comprising a detectable beta-lactamase substrate (e.g., nitrocefin) and one or more beta-lactamase inhibitors; and (b) detecting utilization of the substrate in the compositions, wherein the utilization of the substrate in the compositions indicates whether the presence of the one or more inhibitors inhibits the beta-lactamase(s) present in the bacterial source. Via the results of the different compositions, the presence of certain beta-lactamases in the bacterial source can be determined and the presence of other beta-lactamases can be excluded. Different compositions comprising a detectable beta-lactamase substrate and one or more beta-lactamase inhibitors can be contacted with a bacterial sample from the same source simultaneously or sequentially. The compositions can be presented in any type of carrying vessel or device amenable to detection of substrate utilization following contact of the composition with a bacterial sample. For example, the compositions may be presented in the form of a liquid composition, embedded in an agar plate, a paper disk, a paper strip or a dry form in wells or tubes. In a specific embodiment, the beta-lactamase inhibitors included in one or more of the compositions are a serine beta-lactamase inhibitor, an AmpC inhibitor, a metal chelator and/or an ESBL inhibitor.

The methods and compositions presented herein are based, in part, on the discovery that particular concentrations of beta-lactamase inhibitors can affect its inhibition ability on different beta-lactamases in surprising, unpredictable ways. For example, clavulanic acid at certain concentrations inhibits ESBLs and original-spectrum beta-lactamases (OSBLs) but not class A serine carbapenemases. The inventors, e.g., discovered that the presence of class A serine carbapenemases in a bacterial sample can be differentiated from the presence of ESBLs and OSBLs in a bacterial sample by using certain concentrations of clavulanic acid. The inventors also discovered that a cloxacillin inhibitor at certain concentrations inhibits class A beta-lactamases as well as class C beta-lactamases.

In one embodiment, presented herein is a method for detecting the presence of a beta-lactamase, comprising: (a) contacting: (i) a first bacterial sample with a first composition comprising a detectable beta-lactamase substrate and an AmpC inhibitor, and (ii) a second bacterial sample with a second composition comprising a detectable beta-lactamase substrate, an AmpC inhibitor, and a serine beta-lactamase inhibitor in an amount sufficient to inhibit an ESBL and an OSBL but not a class A serine carbapenemase, wherein the first and second bacterial samples are from the same source; and (b) detecting utilization of the substrate in the first composition and the second composition, such that a beta-lactamase that is a class A serine carbapenemase or a metallo-beta-lactamase is detected if the substrate has been utilized in the first and second compositions.

To differentiate between the presence of a serine carbapenemase and a metallo-beta-lactamase, a third bacterial sample from the same source can be contacted with a third composition comprising a detectable beta-lactamase substrate, an AmpC inhibitor, a serine beta-lactamase inhibitor in an amount sufficient to inhibit an ESBL and an OSBL but not a class A serine carbapenemase, and a metal chelator, and the utilization of the substrate in the third composition is detected. If substrate utilization in the third composition as well as in the first and second compositions is detected, then the presence of a class A serine carbapenemase is detected in the bacterial source. If, on the other hand, there is no substrate utilization detected in third composition but there is substrate utilization detected in the first and second compositions, then the presence of a metallo-beta-lactamase is detected in the bacterial source. If no substrate utilization is detected in the third composition but substrate utilization in the first and second compositions is detected, then the presence of a class A serine carbapenemase can be excluded.

In another embodiment, presented herein is a method for detecting a beta-lactamase, comprising: (a) contacting: (i) a first bacterial sample with a first composition comprising a detectable beta-lactamase substrate, and (ii) a second bacterial sample with a second composition comprising a detectable beta-lactamase substrate and a metal chelator, wherein the first and second bacterial samples are from the same source; and (b) detecting utilization of the substrate in the first composition and the second composition such that: (i) a beta-lactamase other than a metallo-beta-lactamase is detected if the substrate in the first composition and the second composition has been utilized, and (ii) a beta-lactamase that is a metallo-beta-lactamase is detected if the substrate in the first composition has been utilized but the substrate in the second composition has not been utilized. In addition, the failure to detect substrate utilization by the first composition indicates that there is no beta-lactamase present in the bacterial source.

In another embodiment, presented herein is a method for detecting a beta-lactamase, comprising: (a) contacting: (i) a first bacterial sample with a first composition comprising a detectable beta-lactamase substrate and an AmpC inhibitor, (ii) a second bacterial sample with a second composition comprising a detectable beta-lactamase substrate, an AmpC inhibitor, and a serine beta-lactamase inhibitor in an amount sufficient to inhibit an ESBL and an OSBL but not a class A serine carbapenemase, (iii) a third bacterial sample with a third composition comprising a detectable beta-lactamase substrate, an AmpC inhibitor, a serine beta-lactamase inhibitor in an amount sufficient to inhibit an ESBL and an OSBL but not a class A serine carbapenemase, and a metal chelator, and (iv) a fourth bacterial sample with a fourth composition comprising a detectable beta-lactamase substrate and a serine beta-lactamase inhibitor in an amount sufficient to inhibit an ESBL and an OSBL but not a class A serine carbapenemase, wherein the first, second, third and fourth bacterial samples are from the same source; and (b) detecting utilization of the substrate in the first composition, the second composition, the third composition, and the fourth composition such that: (i) a beta-lactamase that is a class A serine carbapenemase is detected if the substrate in the first composition, the second composition, the third composition and the fourth composition has been utilized; (ii) a beta-lactamase that is a metallo-beta-lactamase is detected if the substrate in the first composition, the second composition, and the fourth composition has been utilized but the substrate in the third composition has not been utilized, and (iii) a beta-lactamase that is an AmpC beta-lactamase is detected if the substrate in the fourth composition has been utilized but the substrate in the first composition, the second composition, and the third composition has not been utilized. In addition, the detection of substrate utilization in the first, second and fourth compositions but the failure to detect substrate utilization in the third composition indicates that a class A serine carbapenemase is not present in the bacterial source. Further, the detection of substrate utilization in fourth composition but the failure to detect substrate utilization in the first, second and third compositions indicates that a class A serine carbapenemase, a metallo-beta-lactamase and an ESBL are not present in the bacterial source.

In yet another embodiment, presented herein is a method for detecting the presence of a beta-lactamase, comprising: (a) contacting: (i) a first bacterial sample with a first composition comprising a detectable beta-lactamase substrate and an AmpC inhibitor, (ii) a second bacterial sample with a second composition comprising a detectable beta-lactamase substrate, an AmpC inhibitor, and a serine beta-lactamase inhibitor in an amount sufficient to inhibit an ESBL and an OSBL but not a class A serine carbapenemase, (iii) a third bacterial sample with a third composition comprising a detectable beta-lactamase substrate, an AmpC inhibitor, a serine beta-lactamase inhibitor in an amount sufficient to inhibit an ESBL and an OSBL but not a class A serine carbapenemase, and a metal chelator, (iv) a fourth bacterial sample with a fourth composition comprising a detectable beta-lactamase substrate and a serine beta-lactamase inhibitor in an amount sufficient to inhibit an ESBL and an OSBL but not a class A serine carbapenemase, and (v) a fifth bacterial sample with a fifth composition comprising a detectable beta-lactamase substrate and an ESBL inhibitor, wherein the first, second, third, fourth and fifth bacterial samples are from the same source; and (b) detecting utilization of the substrate in the first composition, the second composition, the third composition, the fourth composition, and fifth composition such that: (i) a beta-lactamase that is an ESBL is detected if the substrate in the first composition has been utilized but the substrate in the second composition, the third composition, the fourth composition, and the fifth composition has not been utilized, (ii) a beta-lactamase that is an AmpC beta-lactamase is detected if the substrate in the fourth composition has been utilized but the substrate in the first composition, the second composition and the third composition has not been utilized, (iii) a beta-lactamase that is a metallo-beta-lactamase is detected if the substrate in the first composition, the second composition, and the fourth composition has been utilized but the substrate in the third composition has not been utilized, and (iv) a beta-lactamase that is a class A serine carbapenemase is detected if the substrate in the first composition, the second composition, the third composition, and the fourth composition has been utilized. In addition, the detection of substrate utilization in the first composition but the failure to detect substrate utilization in the second, third, fourth and fifth compositions indicates that a class A serine carbapenemase, a metallo-beta-lactamase, and an AmpC beta-lactamase are not present in the bacterial source. In addition, the detection of substrate utilization in the first, second and fourth compositions but the failure to detect substrate utilization in the third composition indicates that a class A serine carbapenemase is not present in the bacterial source. Further, the detection of substrate utilization in the fourth composition but the failure to detect substrate utilization in the first, second and third compositions indicates that a class A serine carbapenemase, a metallo-beta-lactamase and an ESBL are not present in the bacterial source.

In certain embodiments, the compositions used in accordance with the methods described herein comprise a lysis reagent. Lysis reagents (e.g., a lysis reagent in a buffer) are known to one of skill in the art. In a specific embodiment, the lysis reagent lyses or promotes lysis of the bacterial cells but does not interfere with either the hydrolysis of the beta-lactamase substrate or the activity of one or more beta-lactamase inhibitors, or both. In one embodiment, the lysis reagent is an enzyme or other agent that promotes the lysis of a bacterial cell. Non-limiting examples of such an enzyme include lysozyme, labiase, lysostaphin, achromopeptidase, and mutanolysin. In a specific embodiment, the compositions used in accordance with the methods described herein comprise lysozyme.

In certain embodiments, the compositions used in accordance with the methods described herein comprise a lysis reagent and an agent that promotes the stabilization of the lysis reagent. In one embodiment, the agent that promotes stabilization of the lysis reagent is thermal stable. In a specific embodiment, the compositions used in accordance with the methods described herein comprise a lysis reagent and a carbohydrate, e.g., a monosaccharide, a disaccharide, a polysaccharide, an oligosaccharide, or a polyol. Specific examples of carbohydrates include, but are not limited to, mannitol, ribose, glucose, fructose, mannose, sucrose, lactose, glycerol, Xanthan gum, trehalose and glycols (e.g., propylene glycol). In a specific embodiment, the compositions used in accordance with the methods described herein comprise lysozyme and trehalose.

In certain embodiments, the compositions used in accordance with the methods described herein comprise a lysis reagent, an agent that promotes stabilization of the lysis reagent, and an additional agent, e.g., an agent that enhances the lysis of a bacterial cell by a lysis reagent (e.g. a metal chelator). In a specific embodiment, the additional agent is EDTA or EGTA. In particular embodiments, either EDTA or EGTA, or both are not utilized if a metallo-beta-lactamase is or may be detected. In a specific embodiment, the compositions used in accordance with the methods described herein comprise a lysozyme, trehalose and EDTA.

In some embodiments, the compositions used in accordance with the methods described herein are in the form of a liquid composition, an agar plate, a paper strip, a paper disk, a tablet, a dry form in wells, or a dry form in one or more tubes, e.g., an array of tubes. In some embodiments, the compositions used in accordance with the methods described herein are dried and are present on or in a solid support, such as the wells of a plate, a tray, a cassette or a panel, a paper strip, a paper disk, or a tube (e.g., a test tube or Eppendorf tube). In certain embodiments, the compositions used in accordance with the methods described herein are dried and are present in the wells of a panel, cassette, tray or plate (e.g., a microtiter plate). In specific embodiments, the compositions used in accordance with the methods described herein are dried and are present in the wells of a Phoenix™ Panel (BD, USA) or the wells of a panel from a BBLT™ Crystal™ Identification System (BD, UDA). In other embodiments, the compositions used in accordance with the methods described herein are dried and are present in the wells of a Vitek® card (bioMerieux, USA). In other embodiments, the compositions used in accordance with the methods described herein are dried and present in the wells of a MicroScan panel (Dade Behring, USA). In other embodiments, the compositions used in accordance with the methods described herein are dried and are present in tubes of an API biochemical test (bioMerieux, USA). In other embodiments, the compositions used in accordance with the methods described herein are dried and are present in the wells of a panel of a Remel RapID™ System (Remel, USA).

In another aspect, presented herein are kits for detecting the presence of particular beta-lactamases. In one embodiment, the kits comprise, in one or more containers: (a) a first composition comprising a detectable beta-lactamase substrate and an AmpC inhibitor; and (b) a second composition comprising a detectable beta-lactamase substrate, an AmpC inhibitor, and a serine beta-lactamase inhibitor in an amount sufficient to inhibit an ESBL, and an OSBL but not a class A serine carbapenemase. In some embodiments, the kits further comprise a third composition comprising a detectable beta-lactamase substrate, a an AmpC inhibitor, a serine beta-lactamase inhibitor in an amount sufficient to inhibit an ESBL and an OSBL but not a class A serine carbapenemase, and a metal chelator. In some embodiments, the kits further comprise a fourth composition comprising a detectable beta-lactamase substrate and a serine beta-lactamase inhibitor in an amount sufficient to inhibit an ESBL and an OSBL but not a class A serine carbapenemase. In some embodiments, the kits further comprise a fifth composition comprising a detectable beta-lactamase substrate and an ESBL inhibitor.

In another embodiment, the kits comprise, in one or more containers: (a) a first composition comprising a detectable beta-lactamase substrate and an AmpC inhibitor; (b) a second composition comprising a detectable beta-lactamase substrate, an AmpC inhibitor, and a serine beta-lactamase inhibitor in an amount sufficient to inhibit an ESBL and an OSBL but not a class A serine carbapenemase; and (c) a third composition comprising a detectable beta-lactamase substrate and a serine beta-lactamase inhibitor in an amount sufficient to inhibit an ESBL and an OSBL but not a class A serine carbapenemase. In other embodiments, the kits comprise, in one or more containers: (a) a first composition comprising a detectable beta-lactamase substrate and an AmpC inhibitor; (b) a second composition comprising a detectable beta-lactamase substrate, an AmpC inhibitor, and a serine beta-lactamase inhibitor in an amount sufficient to inhibit an ESBL and an OSBL but not a class A serine carbapenemase; and (c) a third composition comprising a detectable beta-lactamase substrate and an ESBL inhibitor. In some embodiments, the kits comprise, in one or more containers: (a) a first composition comprising a detectable beta-lactamase substrate; and (b) a second composition comprising a detectable beta-lactamase substrate and a metal chelator.

In some embodiments, the kits described herein contain a composition comprising a lysis reagent. In certain embodiments, in addition to a beta-lactamase substrate and in some embodiments, one or more beta-lactamase inhibitors, the compositions in the kits described herein comprise a lysis reagent. In a specific embodiment, the lysis reagent lyses the bacterial cells but does not interfere with either the hydrolysis of the beta-lactamase substrate or the activity of one or more beta-lactamase inhibitors, or both. In one embodiment, the lysis reagent is a detergent, such as mild non-denaturing detergent (e.g., Triton® X-100 or CHAPS). In another embodiment, the lysis reagent is an enzyme or other agent that promotes the lysis of a bacterial cell. Non-limiting examples of such an enzyme include lysozyme, labiase, lysostaphin, achromopeptidase, and mutanolysin.

In some embodiments, the kits described herein contain a composition comprising a lysis reagent and an agent that promotes the stabilization of the lysis reagent. In certain embodiments, in addition to a beta-lactamase subtrate and in some embodiments, one or more beta-lactamase inhibitors, the compositions in the kits described herein comprise a lysis reagent and an agent that promotes the stabilization of the lysis reagent. In one embodiment, the agent that promotes the stabilization of the lysis reagent is thermal stable.

In a specific embodiment, the kits described herein contain a composition comprising a lysis reagent and a carbohydrate, e.g., a monosaccharide, a disaccharide, a polysaccharide, an oligosaccharide, or a polyol. Specific examples of carbohydrates include, but are not limited to, mannitol, ribose, glucose, fructose, mannose, sucrose, lactose, glycerol, Xanthan gum, trehalose and glycols (e.g., propylene glycol). In a specific embodiment, the compositions in the kits described herein comprise lysozyme and trehalose.

In some embodiments, the kits described herein contain a composition comprising a lysis reagent, an agent that promotes the stabilization of the lysis reagent, and an additional agent, e.g., an agent that enhances the lysis of a bacterial cell by a lysis reagent (e.g., a metal chelator). In a specific embodiment, the additional agent is EDTA or EGTA. In particular embodiments, either EDTA or EGTA, or both are not utilized if a metallo-beta-lactamase is or may be detected. In a specific embodiment, the compositions in the kits described herein comprise a lysozyme, trehalose and EDTA.

In some embodiments, the compositions in the kits described herein are in the form of a liquid composition, an agar plate, a paper strip, a paper disk, a tablet, a dry form in wells, or a dry form in one or more tubes, e.g., an array of tubes. In some embodiments, the compositions used in accordance with the methods described herein are dried and are present on or in a solid support, such as a well of a plate, a tray, a cassette or a panel, a paper strip, a paper disk or a tube (e.g., a test tube or Eppendorf tube). In certain embodiments, the compositions in the kits described herein are dried and are present in the wells of a panel, tray, cassette or plate (e.g., a microtiter plate). In specific embodiments, the compositions in the kits described herein are dried and are present in the wells of a Phoenix™ Panel (BD, USA) or the wells of a panel from a BBLT™ Crystal™ Identification System (BD, UDA). In other embodiments, the compositions in the kits described herein are dried and are present in the wells of a Vitek® card (bioMerieux, USA). In other embodiments, the compositions in the kits described herein are dried and are present in the wells of a MicroScan panel (Dade Behring, USA). In other embodiments, the compositions in the kits described herein are dried and are present in tubes of an API biochemical test (bioMerieux, USA). In other embodiments, the compositions in the kits described herein are dried the wells of a panel of a Remel RapID™ System (Remel, USA).

3.1 Terminology

As used herein, the terms "about" and "approximately", unless otherwise indicated, refer to a value that is no more than 20% above or below the value being modified by the term.

As used herein, the terms "agent that promotes the stabilization of the lysis reagent" and "agent that promotes the stabilization of a lysis reagent" refer to an agent that prevents the loss of a lysis reagent's ability to lyse bacterial cells after exposure to temperatures of greater than about 50° C. In a specific embodiment, the agent prevents the loss of a lysis reagent's ability to lyse bacterial cells after exposure to temperatures of about 50° C. to about 120° C., about 50° C. to about 100° C., about 50° C. to about 85° C., about 50° C. to about 80° C., or about 60° C. to about 75° C. In another specific embodiment, the agent prevents the loss of a lysis reagent's ability to lyse bacterial cells after exposure to temperatures of about 50° C. to about 120° C., about 50° C. to about 100° C., about 50° C. to about 85° C., about 50° C. to about 80° C., or about 60° C. to about 75° C. for at least 5 minutes, at least 10 minutes, at least 15 minutes, at least 20 minutes, at least 30 minutes, at least 45 minutes, at least 1 hour, at least 1.5 hours or at least 2 hours. In another specific embodiment, the agent prevents the loss of a lysis reagent's ability to lyse bacterial cells after exposure to temperatures of about 50° C. to about 120° C., about 50° C. to about 100° C., about 50° C. to about 85° C., about 50° C. to about 80° C., or about 60° C. to about 75° C. for about 2 minutes to about 3 hours, about 2 minutes to about 2 hours, about 2 minutes to about 1 hour, about 2 minutes to about 30 minutes, about 2 minutes to about 15 minutes, about 15 minutes to about 2 hours, about 15 minutes to about 1.5 hours, about 15 minutes to about 1 hour, about 15 minutes to about 45 minutes or about 15 minutes to about 30 minutes.

As used herein, the term "pure bacterial sample" means a sample collected from one or more bacterial colonies from the same source resulting from streaking an agar-containing medium with a biological sample containing bacteria. When the sample is from more than one colony, generally all of the colonies are from the same species.

As used herein, the term "same source" in the context of bacterial samples means two or more bacterial samples that are isolated, obtained or derived from a biological sample(s) from the same entity (e.g., a human subject). For example, two or more bacterial samples may be obtained from one, two or more tissues, organs or secretions from one subject.

As used herein, the terms "subject" and "patient" are used interchangeably to refer to an animal subject. In a specific embodiment, the subject is a mammal. In another embodiment, the subject is a non-human. In a preferred embodiment, the subject is a human.

With respect to beta-lactamases, as used herein, the term "substrate utilization" means the hydrolysis of a substrate by a beta-lactamase.

4. DETAILED DESCRIPTION

4.1 Beta-Lactamase Assays

Presented herein are methods for the rapid detection of particular beta-lactamases using compositions comprising a detectable beta-lactamase substrate and one or more beta-lactamase inhibitors. The methods presented herein can comprise: (a) contacting two or more bacterial samples from the same source with different compositions comprising a detectable beta-lactamase substrate (e.g., nitrocefin) and one or more beta-lactamase inhibitors; and (b) detecting utilization of the substrate in the compositions, wherein the utilization of the substrate in the compositions indicates whether the presence of the one or more inhibitors inhibits the beta-lactamase(s) present in the bacterial samples. Via the results of the different compositions, the presence of certain beta-lactamases in the bacterial source can be determined and/or the presence of other beta-lactamases can be excluded.

The methods presented herein may, for example, comprise: (a) contacting: (i) a first bacterial sample with a first composition comprising a detectable beta-lactamase substrate and one or more beta-lactamase inhibitors, and (ii) a second bacterial sample with a second composition comprising a detectable beta-lactamase substrate and one or more beta-lactamase inhibitors, wherein at least one such beta-lactamase inhibitor is different than the one or more beta-lactamase inhibitors in the first composition, wherein the first and second bacterial samples are from the same source; and (b) detecting utilization of the substrate in the first composition and the second composition, wherein substrate utilization in the first composition and/or second composition indicates the presence of one or more particular beta-lactamases in the bacterial source and in some instances, the absence of one or more particular beta-lactamases. In a specific embodiment, a control composition comprising a detectable beta-lactamase substrate and no beta-lactamase inhibitor is also contacted with a bacterial sample from the same source as the other compositions. Detection of substrate utilization in this control composition confirms that a beta-lactamase is present in the bacterial source. In some embodiments, a positive control comprising a bacterial sample that is known to express one or more beta-lactamases and/or a negative control comprising a bacterial sample that is known not to express one or more particular beta-lactamases is included in the methods presented herein.

In certain embodiments, the first composition, second composition and control composition described in the preceding paragraph comprise a lysis reagent. In a specific embodiment, the first composition, second composition and control composition described in the preceding paragraph comprise a lysis reagent and an agent that promotes the stabilization of the lysis reagent. In another embodiment, the first composition, second composition and control composition described in the preceding paragraph comprise a lysis reagent, an agent that promotes the stabilization of the lysis reagent, and an agent that enhances the lysis of a bacterial cell by a lysis reagent.

Table 1, below, provides an exemplary list of compositions that can be used to detect the presence of particular beta-lactamases in a bacterial sample and identifies beta-lactamases that can be detected based upon detection of substrate utilization in different compositions. By comparing substrate utilization when a bacterial sample from the same source is contacted with different compositions, the presence of a particular beta-lactamase can be detected and in some instances, the presence of a particular beta-lactamase can be excluded.

In some embodiments, 1, 2, 3, 4, 5 or all of the compositions in Table 1, below, are used to detect the presence of a particular beta-lactamase in a bacterial source. For example, in certain embodiments, a first bacterial sample, a second bacterial sample and a third bacterial sample from the same source are contacted with composition #1, composition #4, and composition #5 in Table 1, below, respectively, and the utilization of the substrate in the compositions is detected. If substrate utilization is detected in composition #1 and composition #4, but substrate utilization in composition #5 is not detected, then the presence of a metallo-beta-lactamase is present in the bacterial source. If substrate utilization is detected in all three compositions, then a class A serine carbapenemase is present in the bacterial source is detected. If substrate utilization is detected in composition #1, but substrate utilization is not detected in compositions #4 and #5, then a beta-lactamase other than a class A serine carbapenemase and a metallo-beta-lactamase is present in the bacterial source.

TABLE 1

| Composition | Class A Serine Carbapenemase | MBL | AmpC* + ESBL OR AmpC* + OSBL | AmpC* | ESBL | OSBL | No detectable beta-lactamase |
| --- | --- | --- | --- | --- | --- | --- | --- |
| Composition #1 (Detectable Substrate) | ++ | ++ | ++ | ++ | +/++ | +/++ | − |
| Composition #2 (Detectable substrate & serine beta-lactamase inhibitor) | + | ++ | ++ | ++ | − | − | − |
| Composition #3 (Detectable substrate & AmpC inhibitor) | + | + | + | − | + | +/− | − |
| Composition #4 (Detectable substrate, serine beta-lactamase inhibitor & AmpC inhibitor) | + | + | − | − | − | − | − |
| Composition #5 (Detectable substrate, metal chelator, serine beta-lactamase inhibitor & AmpC inhibitor) | + | − | − | − | − | − | − |

TABLE 1-continued

| Composition | Class A Serine Carbapenemase | MBL | AmpC* + ESBL OR AmpC* + OSBL | AmpC* | ESBL | OSBL | No detectable beta-lactamase |
|---|---|---|---|---|---|---|---|
| Composition # 6 (Detectable substrate & ESBL inhibitor) | +/− | +/− | +/− | +/− | − | + | − |

AmpC* refers to plasmid-mediated AmpC or inducible chromosomal AmpC beta-lactamase.
+ and ++ indicate substrate utilization.
+/− indicates the substrate may or may not be utilized in a particular reaction.
− indicates that the substrate is not utilized.

In one embodiment, a method for detecting the presence of a serine carbapenemase or a metallo-beta-lactamase, comprises: (a) contacting: (i) a first bacterial sample with a first composition comprising a detectable beta-lactamase substrate and an AmpC inhibitor, and (ii) a second bacterial sample with a second composition comprising a detectable beta-lactamase substrate, an AmpC inhibitor, and a serine beta-lactamase inhibitor in an amount sufficient to inhibit an extended-spectrum beta-lactamase (ESBL) and an original-spectrum beta-lactamase (OSBL) but not a class A serine carbapenemase, wherein the first and second bacterial samples are from the same source; and (b) detecting utilization of the substrate in the first composition and the second composition, such that a class A serine carbapenemase or a metallo-beta-lactamase is detected if the substrate has been utilized in the first and second compositions. To differentiate between the presence of a serine carbapenemase and a metallo-beta-lactamase, a third bacterial sample from the same source as the first and second bacterial samples can be contacted with a third composition comprising a detectable beta-lactamase substrate, an AmpC inhibitor, a serine beta-lactamase inhibitor in an amount sufficient to inhibit an ESBL and an OSBL but not a class A serine carbapenemase, and a metal chelator, and the utilization of the substrate in the third composition is detected. If substrate utilization in the third composition as well as in the first and second compositions is detected, then the presence of a class A serine carbapenemase is detected in the bacterial source. If, on the other hand, there is no substrate utilization detected in third composition but there is substrate utilization detected in the first and second compositions, then the presence of a metallo-beta-lactamase is detected in the bacterial source. In addition, if no substrate utilization is detected in the third composition but substrate utilization in the first and second compositions is detected, then the presence of a class A serine carbapenemase can be excluded. Table 2, below, summarizes results when a bacterial sample containing a class A serine carbapenemase or a metallo-beta-lactamase is contacted with the compositions described in this paragraph.

TABLE 2

| Composition | Substrate Utilization | |
|---|---|---|
| Detectable substrate & AmpC inhibitor | + | + |
| Detectable substrate, AmpC inhibitor & serine beta-lactamase inhibitor | + | + |
| Detectable substrate, AmpC inhibitor, serine beta-lactamase inhibitor & metal chelator | + | − |
| | Indicates the presence of a class A serine carbapenemase | Indicates the presence of a metallo-beta-lactamase & excludes the presence of a class A serine carbapenemase |

AmpC refers to plasmid-mediated AmpC or inducible chromosomal AmpC. beta-lactamase
+ indicates substrate utilization.
− indicates that the substrate is not utilized.

In a specific embodiment, a method for detecting the presence of a beta-lactamase, comprises: (a) contacting: (i) a first bacterial sample with a first composition comprising a chromogenic beta-lactamase substrate and an AmpC inhibitor, and (ii) a second bacterial sample with a second composition comprising a chromogenic beta-lactamase substrate, an AmpC inhibitor, and a serine beta-lactamase inhibitor in an amount sufficient to inhibit an ESBL and an OSBL but not a class A serine carbapenemase, wherein the first and second bacterial samples are from the same source; and (b) detecting the color of the first composition and the second composition, such that a beta-lactamase is detected if the color of the first and second compositions has changed in a manner indicating substrate utilization, wherein the beta-lactamase is a class A serine carbapenemase or a metallo-beta-lactamase. In one embodiment, the AmpC inhibitor is cloxacillin. In another embodiment, the serine beta-lactamase inhibitor is clavulanic acid. The first and second compositions, described in the preceding embodiments may be used independently or together in various combinations as one of skill in the art would appreciate. In another embodiment, the chromogenic beta-lactamase substrate is nitrocefin. In a specific embodiment, the first composition comprises 20 μM to 200 μM of nitrocefin, 20 μM to 5 mM of cloxacillin, and 0.05 M to 1 M phosphate, or MES buffer. In another embodiment, the second composition comprises 20 μM to 200 μM of nitrocefin, 20 μM to 5 mM of cloxacillin, 1 μM to 1.5 mM clavulanic acid, and 0.05 M to 1 M phosphate or MES buffer. In another embodiment, each composition is pH 5 to pH 7. In a specific embodiment, the concentration of inhibitor used in a composition is dependent on the concentration of beta-lactamase substrate in the composition.

In another specific embodiment, a method for detecting the presence of a beta-lactamase, comprises: (a) contacting: (i) a first bacterial sample with a first composition comprising a chromogenic beta-lactamase substrate and an AmpC inhibitor, (ii) a second bacterial sample with a second composition comprising a chromogenic beta-lactamase substrate, an AmpC inhibitor, and a serine beta-lactamase inhibitor in an amount sufficient to inhibit an ESBL and an OSBL but not a class A serine carbapenemase, and (iii) a third bacterial sample with a third composition comprising a chromogenic beta-lactamase substrate, an AmpC inhibitor, a serine beta-lactamase inhibitor in an amount sufficient to inhibit an ESBL and an OSBL but not a class A serine carbapenemase, and a metal chelator, wherein the first, second and third bacterial samples are from the same source; and (h) detecting the color of the first composition, the second composition, and the third composition, such that: (i) a beta-lactamase that is a class A serine carbapenemase is detected if the color of the first composition, the second composition and the third composition has changed in a manner indicating substrate utilization, and (ii) a beta-lactamase that is a metallo-beta-lactamase is detected if the color of the first composition and the second composition has changed in a manner indicating substrate utilization but the color of the third composition has not changed in a manner indicating substrate utilization. In one embodiment, the AmpC inhibitor is cloxacillin. In another embodiment, the serine beta-lactamase inhibitor is clavulanic acid. In another embodiment, the metal chelator is dipicolinic acid or diethyldithiocarbamate. In another embodiment, the chromogenic beta-lactamase substrate is nitrocefin. In a specific embodiment, the first composition comprises 20 μM to 200 μM of nitrocefin, 20 μM to 5 mM of cloxacillin, and 0.05 M to 1 M phosphate, or MES buffer. In another embodiment, the second composition comprises 20 μM to 200 μM of nitrocefin, 20 μM to 5 mM of cloxacillin, 0.1 μM to 1.5 mM of clavulanic acid, and 0.05 M to 1 M phosphate, or MES buffer. In another embodiment, the third composition comprises 20 μM to 200 μM of nitrocefin, 20 μM to 5 mM of cloxacillin, 0.1 μM to 1.5 mM of clavulanic acid, 0.5 mM to 1.5 mM of dipicolinic acid (DPC) or 1 mM to 20 mM diethyldithiocarbamate (DEDTC) and 0.05 M to 1 M phosphate, or MES buffer. The first, second and third compositions described in the preceding embodiments may be used independently or together in various combinations as one of skill in the art will appreciate. In another embodiment, each composition is pH 5 to pH 7. In a specific embodiment, the concentration of inhibitor used in a composition is dependent on the concentration of beta-lactamase substrate in the composition.

In another embodiment, presented herein is a method for detecting a beta-lactamase, comprising: (a) contacting: (i) a first bacterial sample with a first composition comprising a detectable beta-lactamase substrate, and (ii) a second bacterial sample with a second composition comprising a detectable beta-lactamase substrate and a metal chelator, wherein the first and second bacterial samples are from the same source; and (b) detecting utilization of the substrate in the first composition and the second composition such that: (i) a beta-lactamase other than a metallo-beta-lactamase is detected if the substrate in the first composition and the second composition has been utilized, and (ii) a beta-lactamase that is a metallo-beta-lactamase is detected if the substrate in the first composition has been utilized but the substrate in the second composition has not been utilized. In addition, the failure to detect substrate utilization by the first composition and the second composition indicates that there is no beta-lactamase present in the bacterial source. Table 3, below, summarizes results when a bacterial sample containing a metallo-beta-lactamase or a beta-lactamase other than a metal-beta-lactamase is contacted with the compositions described in this paragraph.

TABLE 3

| Composition | Substrate Utilization | |
| --- | --- | --- |
| Detectable beta-lactamase substrate | + | + |
| Detectable beta-lactamase substrate & metal chelator | + | − |
| | Indicates the presence of a beta-lactamase other than a metallo-beta-lactamase | Indicates the presence a metallo-beta-lactamase |

In another specific embodiment, a method for detecting the presence of a beta-lactamase, comprises: (a) contacting: (i) a first bacterial sample with a first composition comprising a chromogenic beta-lactamase substrate, and (ii) a second bacterial sample with a second composition comprising a chromogenic beta-lactamase substrate and a metal chelator, wherein the first and second samples are from the same source; and (b) detecting the color of the first composition and the second composition, such that: (i) a beta-lactamase other than a metallo-beta-lactamase is detected if the color of the first composition and the second composition has changed in a manner indicating substrate utilization, and (ii) a beta-lactamase that is a metallo-beta-lactamase is detected if the color of the first composition has changed in a manner indicating substrate utilization but the color of the second composition has not changed in a manner indicating substrate utilization. In one embodiment, the chromogenic beta-lactamase substrate is nitrocefin. In another embodiment, the metal chelator is dipicolinic acid (DPC) or diethyldithiocarbamate (DEDTC). In a specific embodiment, the first composition comprises 20 μM to 200 μM of nitrocefin and 0.05 M to 1 M phosphate or MES buffer. In another embodiment, the second composition comprises 20 μM to 200 μM of nitrocefin and 0.5 mM to 10 mM of dipicolinic acid (DPC) or 1 mM to 20 mM diethyldithiocarbamate (DEDTC) and 0.05 M to 1 M phosphate or MES buffer. The first and second compositions, described in the preceding embodiments may be used independently or together in various combinations as one of skill in the art would appreciate. In another embodiment, each composition is pH 5 to pH 7. In a specific embodiment, the concentration of inhibitor used in a composition is dependent on the concentration of beta-lactamase substrate in the composition.

In another embodiment, a method for detecting a beta-lactamase, comprises: (a) contacting: (i) a first bacterial sample with a first composition comprising a detectable beta-lactamase substrate and an AmpC inhibitor, (ii) a second bacterial sample with a second composition comprising a detectable beta-lactamase substrate, an AmpC inhibitor, and a serine beta-lactamase inhibitor in an amount sufficient to inhibit an ESBL and an OSBL but not a class A serine carbapenemase, (iii) a third bacterial sample with a third composition comprising a detectable beta-lactamase substrate, an AmpC inhibitor, a serine beta-lactamase inhibitor in an amount sufficient to inhibit an ESBL and an OSBL but not a class A serine carbapenemase, and a metal chelator, and (iv) a fourth bacterial sample with a fourth composition comprising a detectable beta-lactamase substrate and a serine beta-lactamase inhibitor in an amount sufficient to inhibit an ESBL and an OSBL but not a class A serine carbapenemase, wherein the first, second, third and fourth bacterial samples are from the same source; and (b) detecting utilization of the substrate in the first composition, the second composition, the third composition, and the fourth composition such that: (i) a beta-lactamase that is a class A serine carbapenemase is detected if the substrate in the first composition, the second composition, the third composition and the fourth composition has been utilized; (ii) a beta-lactamase that is a metallo-beta-lactamase is detected if the substrate in the first composition, the second composition, and the fourth composition has been utilized but the substrate in the third composition has not been utilized, and (iii) a beta-lactamase that is an AmpC beta-lactamase is detected if the substrate in the fourth composition has been utilized but the substrate in the first composition, the second composition, and the third composition has not been utilized. In addition, the detection of substrate utilization in the first, second and fourth compositions but the failure to detect substrate utilization in the third composition indicates that a class A serine carbapenemase is not present in the bacterial source. Further, the detection of substrate utilization in the fourth composition but the failure to detect substrate utilization in the first, second and third compositions indicates that a class A serine carbapenemase, a metallo-beta-lactamase and an ESBL are not present in the bacterial source. Table 4, below, summarizes results when a bacterial sample containing a class A serine carbapenemase, a metallo-beta-lactamase or an AmpC beta-lactamase is contacted with the compositions described in this paragraph.

class A serine carbapenemase is detected if the color of the first composition, the second composition, the third composition and the fourth composition has changed in a manner indicating substrate utilization; (ii) a beta-lactamase that is a metallo-beta-lactamase is detected if the color of the first composition, the second composition, and the fourth composition has changed in a manner indicating substrate utilization but the color of the third composition has not changed in a manner indicating substrate utilization, and (iii) a beta-lactamase that is an AmpC beta-lactamase is detected if the color of the fourth composition has changed in a manner indicating substrate utilization but the color of the first composition, the second composition, and the third composition has not changed in a manner indicating substrate utilization. In one embodiment, the AmpC inhibitor is cloxacillin. In another embodiment, the serine beta-lactamase inhibitor is clavulanic acid. In another embodiment, the metal chelator is DPC or DEDTC. In another embodiment, the chromogenic substrate is nitrocefin. In a specific embodiment, the first composition comprises 20 µM to 200 µM of nitrocefin, 20 µM to 5 mM of cloxacillin, and 0.05 M to 1 M phosphate or MES buffer. In another embodiment, the second composition comprises 20 µM to 200 µM of nitrocefin, 20 µM to 5 mM of cloxacillin, 1

TABLE 4

| Composition | Substrate Utilization | | |
|---|---|---|---|
| Detectable substrate & AmpC inhibitor | + | ++ | − |
| Detectable substrate, AmpC inhibitor & serine beta-lactamase inhibitor | + | + | − |
| Detectable substrate, AmpC inhibitor, serine beta-lactamase inhibitor & metal chelator | + | − | − |
| Detectable substrate & serine beta-lactamase inhibitor | + | + | + |
| | Indicates the presence of a class A serine carbapenemase | Indicates the presence of metallo-beta-lactamase & excludes the presence of a class A serine carbapenemase | Indicates the presence of an AmpC & excludes the presence of a class A serine carbapenemase & a metallo-beta-lactamase & ESBL |

AmpC refers to plasmid-mediated AmpC or inducible chromosomal AmpC beta-lactamase.
+ indicates substrate utilization.
− indicates that the substrate is not utilized.

In a specific embodiment, a method for detecting a beta-lactamase, comprises: (a) contacting: (i) a first bacterial sample with a first composition comprising a chromogenic beta-lactamase substrate and an AmpC inhibitor, (ii) a second bacterial sample with a second composition comprising chromogenic beta-lactamase substrate, an AmpC inhibitor, and a serine beta-lactamase inhibitor in an amount sufficient to inhibit an ESBL and an OSBL but not a class A serine carbapenemase, (iii) a third bacterial sample with a third composition comprising a chromogenic beta-lactamase substrate, an AmpC inhibitor, a serine beta-lactamase inhibitor in an amount sufficient to inhibit an ESBL and an OSBL but not a class A serine carbapenemase, and a metal chelator, and (iv) a fourth bacterial sample with a fourth composition comprising a chromogenic beta-lactamase substrate and a serine beta-lactamase inhibitor in an amount sufficient to inhibit an ESBL and an OSBL but not a class A serine carbapenemase, wherein the first, second, third and fourth bacterial samples are from the same source; and (b) detecting the color of the first composition, the second composition, the third composition, and the fourth composition such that: (i) a beta-lactamase that is a µM to 1.5 mM of clavulanic acid, and 0.05 M to 1 M phosphate or MES buffer. In another embodiment, the third composition comprises 20 µM to 200 µM of nitrocefin, 20 µM to 5 mM of cloxacillin, 1 µM to 1.5 mM of clavulanic acid, 0.5 mM to 10 mM of DPC or 1 mM to 20 mM DEDTC and 0.05 M to 1 M phosphate or MES in buffer. In another embodiment, the fourth composition comprises 20 µM to 200 µM of nitrocefin, 1 µM to 1.5 mM of clavulanic acid and 0.05 M to 1 M phosphate or MES buffer. The first, second, third and fourth compositions described in the preceding embodiments may be used independently or together in various combinations as one of skill in the art will appreciate. In another embodiment, each composition is pH 5 to pH 7. In a specific embodiment, the concentration of inhibitor used in a composition is dependent on the concentration of beta-lactamase substrate in the composition.

In another embodiment, a method for detecting the presence of a beta-lactamase, comprises: (a) contacting: (i) a first bacterial sample with a first composition comprising a detectable beta-lactamase substrate and an AmpC inhibitor, (ii) a second bacterial sample with a second composition comprising a detectable beta-lactamase substrate, an AmpC inhibitor, and a serine beta-lactamase inhibitor in an amount sufficient to inhibit an ESBL and an OSBL but not a class A serine carbapenemase, (iii) a third bacterial sample with a third composition comprising a detectable beta-lactamase substrate, an AmpC inhibitor, a serine beta-lactamase inhibitor in an amount sufficient to inhibit an ESBL and an OSBL but not a class A serine carbapenemase, and a metal chelator, (iv) a fourth bacterial sample with a fourth composition comprising a detectable beta-lactamase substrate and a serine beta-lactamase inhibitor in an amount sufficient to inhibit an ESBL and an OSBL but not a class A serine carbapenemase, and (v) a fifth bacterial sample with a fifth composition comprising a detectable beta-lactamase substrate and an ESBL inhibitor, wherein the first, second, third, fourth and fifth bacterial samples are from the same source; and (b) detecting utilization of the substrate in the first composition, the second composition, the third composition, the fourth composition, and fifth composition such that: (i) a beta-lactamase that is an ESBL is detected if the substrate in the first composition has been utilized but the substrate the second composition, the third composition, the fourth composition, and the fifth composition has not been utilized, (ii) a beta-lactamase that is an AmpC beta-lactamase is detected if the substrate in the fourth composition has been utilized but the substrate in the first composition, the second composition and the third composition has not been utilized, (iii) a beta-lactamase that is a metallo-beta-lactamase is detected if the substrate in the first composition, the second composition, and the fourth composition has been utilized but the substrate in the third composition has not been utilized, and (iv) a beta-lactamase that is a class A serine carbapenemase is detected if the substrate in the first composition, the second composition, the third composition, and the fourth composition has been utilized. In addition, the detection of substrate utilization in first composition but the failure to detect substrate utilization in the second, third, fourth and fifth compositions indicates that a class A serine carbapenemase, a metallo-beta-lactamase, and an AmpC beta-lactamase are not present in the sample. In addition, the detection of substrate utilization in the first, second and fourth compositions but the failure to detect substrate utilization in the third composition indicates that a class A serine carbapenemase is not present in the bacterial source. Further, the detection of substrate utilization in the fourth composition but the failure to detect substrate utilization in the first, second and third compositions indicates that a class A serine carbapenemase, a metallo-beta-lactamase and an ESBL are not present in the bacterial source. Table 5, below, summarizes results when a bacterial sample containing a serine carbapenemase, a metallo-beta-lactamase, an AmpC or an ESBL is contacted with the compositions described in this paragraph.

In another embodiment, a method for detecting the presence of a beta-lactamase, comprises: (a) contacting: (i) a first bacterial sample with a first composition comprising a chromogenic beta-lactamase substrate and an AmpC inhibitor, (ii) a second bacterial sample with a second composition comprising a chromogenic beta-lactamase substrate, an AmpC inhibitor, and a serine beta-lactamase inhibitor in an amount sufficient to inhibit an ESBL and an OSBL but not a class A serine carbapenemase, (iii) a third bacterial sample with a third composition comprising a chromogenic beta-lactamase substrate, an AmpC inhibitor, a serine beta-lactamase inhibitor in an amount sufficient to inhibit an ESBL and an OSBL but not a class A serine carbapenemase, and a metal chelator, (iv) a fourth bacterial sample with a fourth composition comprising a chromogenic beta-lactamase substrate and a serine beta-lactamase inhibitor in an amount sufficient to inhibit an ESBL and an OSBL but not a class A serine carbapenemase, and (v) a fifth bacterial sample with a fifth composition comprising a chromogenic beta-lactamase substrate and an ESBL inhibitor, wherein the first, second, third, fourth and fifth bacterial samples are from the same source; and (b) detecting the color of the first composition, the second composition, the third composition, the fourth composition, and fifth composition such that: (i) a beta-lactamase that is an ESBL is detected if the color of the first composition has changed in a manner indicating substrate utilization but the color of the second composition, the third composition, the fourth composition, and the fifth composition has not changed in a manner indicating substrate utilization, (ii) a beta-lactamase that is an AmpC beta-lactamase is detected if the color of the fourth composition has changed in a manner indicating substrate utilization but the color of the first composition, the second composition and the third composition has not changed in a manner indicating substrate utilization, (iii) a beta-lactamase that is a metallo-beta-lactamase is detected if the color of the first composition, the second composition, and the fourth composition has changed in a manner indicating substrate utilization but the color of the third composition has not changed in a manner indicating substrate utilization, and (iv) a beta-lactamase that is a class A serine carbapenemase is detected if the color of the first composition, the second composition, the third composition, and the fourth composition has changed in a manner indicating substrate utilization. In one embodiment, the AmpC inhibitor is cloxacillin. In another embodiment, the serine beta-lactamase inhibitor is clavulanic acid. In another embodiment, the metal chelator is DEDTC or DPC. In another embodiment, the ESBL inhibitor is cefotaxime or ceftazidime. In another embodiment, the chromogenic substrate is nitrocefin. In a specific embodiment, the first composition comprises 20 µM to 200 µM of nitrocefin, 20 µM to 5 mM of cloxacillin, and 0.05 M to 1 M phosphate or MES buffer. In another embodiment, the second composition comprises 20 µM to 200 µM of nitrocefin, 20 µM to 5 mM of cloxacillin, 0.5 mM to 1.5 mM of clavulanic acid, and 0.05 M to 1 M phosphate or MES buffer. In another embodiment, the third composition comprises 20 µM to 200 µM of nitrocefin, 20 µM to 5 mM of cloxacillin, 0.1 µM to 1.5 mM of clavulanic acid, 0.5 mM to 10 mM of DPC or 1 mM to 20 mM DEDTC and 0.05 M to 1 M phosphate or MES buffer. In another embodiment, the fourth composition comprises 20 µM to 200 µM of nitrocefin, 0.1 µM to 1.5 mM of clavulanic acid and 0.05 M to 1 M phosphate or MES buffer. In another embodiment, the fifth composition comprises 20 µM to 200 µM of nitrocefin, 1 mM to 10 mM of cefotaxime or ceftazidime and 0.05 M to 1 M phosphate or MES buffer. The first, second, third, fourth and fifth compositions described in the preceding embodiments may be used independently or together in various combinations as one of skill in the art will appreciate. In another embodiment, each composition is pH 5 to pH 7. In a specific embodiment, the concentration of inhibitor used in a composition is dependent on the concentration of beta-lactamase substrate in the composition.

TABLE 5

| Composition | Substrate Utilization | | | |
|---|---|---|---|---|
| Detectable substrate & AmpC inhibitor | + | + | − | + |
| Detectable substrate, AmpC inhibitor and serine beta-lactamase inhibitor | + | + | − | − |
| Detectable substrate, AmpC inhibitor, serine beta-lactamase inhibitor & a metal chelator | + | − | − | − |
| Detectable substrate & serine beta-lactamase inhibitor | + | + | − | − |
| Detectable substrate & ESBL inhibitor | +/− | +/− | +/− | − |
| | Indicates the presence of a class A serine carbapenemase | Indicates the presence of a metallo-beta-lactamase & excludes the presence of a class A serine carbapenemase | Indicates the presence of an AmpC & excludes the presence of a class A serine carbapenemase, a metallo-beta-lactamase & ESBL | Indicates the presence of ESBL & excludes the presence of a class A serine carbapenemase, a metallo-beta-lactamase and an AmpC |

AmpC refers to plasmid-mediated AmpC or inducible chromosomal AmpC beta-lactamase.
+ indicates substrate utilization.
+/− indicates the substrate may or may not be utilized in a particular reaction.
− indicates that the substrate is not utilized.

In another embodiment, a method for detecting the presence of a beta-lactamase(s), comprises: (a) contacting: (i) a first bacterial sample with a first composition comprising a detectable beta-lactamase substrate and an AmpC inhibitor, (ii) a second bacterial sample with a second composition comprising a detectable beta-lactamase substrate and a serine beta-lactamase inhibitor in an amount sufficient to inhibit an ESBL and an OSBL but not a class A serine carbapenemase, and (iii) a third bacterial sample with a third composition comprising a detectable beta-lactamase substrate, an AmpC inhibitor, and a serine beta-lactamase inhibitor in an amount sufficient to inhibit an ESBL and an OSBL but not a class A serine carbapenemase, wherein the first, second and third, bacterial samples are from the same source; and (b) detecting utilization of the substrate in the first composition, the second composition, and the third composition such that: (i) beta-lactamases that are an AmpC and an ESBL or that is an AmpC and OSBL is detected if the substrate in the first composition and second composition has been utilized but the substrate in the third composition has not been utilized, (ii) a beta-lactamase that is an AmpC is detected if the substrate in the second composition has been utilized but the substrate in the first composition and the third composition has not been utilized, and (iii) a beta-lactamase that is an ESBL and/or OSBL is detected if the substrate in the first composition has been utilized but the substrate in the second composition and the third composition has not been utilized. In addition, the detection of substrate utilization in the second composition but the failure to detect substrate utilization in the first and third compositions indicates that an ESBL and/or an OSBL are not present in the bacterial source. Table 6, below, summarizes results when a bacterial sample containing an AmpC, an ESBL and/or an OSBL is contacted with the compositions described in this paragraph.

TABLE 6

| Composition | Substrate Utilization | | |
|---|---|---|---|
| Detectable substrate & AmpC inhibitor | + | − | + |
| Detectable substrate & serine beta-lactamase inhibitor | + | + | − |
| Detectable substrate, AmpC inhibitor & serine beta-lactamase inhibitor | − | − | − |
| | Indicates the presence of AmpC + ESBL or AmpC + OSBL | Indicates the presence of an AmpC & excludes the presence of ESBL &/or OSBL | Indicates the presence of an ESBL &/or OSBL |

AmpC means plasmid-mediated AmpC or inducible chromosomal AmpC.

In another embodiment, a method for detecting the presence of a beta-lactamase, comprises: (a) contacting: (i) a first bacterial sample with a first composition comprising a chromogenic beta-lactamase substrate and an AmpC inhibitor, (ii) a second bacterial sample with a second composition comprising a chromogenic beta-lactamase substrate and a serine beta-lactamase inhibitor in an amount sufficient to inhibit an ESBL and an OSBL but not a class A serine carbapenemase, and (iii) a third bacterial sample with a third composition comprising a chromogenic beta-lactamase substrate, an AmpC inhibitor, and a serine beta-lactamase inhibitor in an amount sufficient to inhibit an ESBL and an OSBL but not a class A serine carbapenemase, wherein the first, second and third bacterial samples are from the same source; and (b) detecting the color of the first composition, the second composition, and the third composition such that: (i) beta-lactamases that are an AmpC and an ESBL or an AmpC and OSBL is detected if the color of the first composition and second composition has been changed in a manner indicating substrate utilization but the color of the third composition has not changed in a manner indicating substrate utilization, (ii) a beta-lactamase that is an AmpC is detected if the color of the second composition has changed in a manner indicating substrate utilization but the color of the first composition and the third composition has not changed in a manner indicating substrate utilization, and (iii) a beta-lactamase that is an ESBL and/or OSBL is detected if the color of the first composition has changed in a manner indicating substrate utilization but the color of the second composition and the third composition has not changed in a manner indicating substrate utilization. In one embodiment, the AmpC inhibitor is cloxacillin. In another embodiment, the serine beta-lactamase inhibitor is clavulanic acid. In another embodiment, the chromogenic substrate is nitrocefin. In a specific embodiment, the first composition comprises 20 µM to 200 µM of nitrocefin, 20 µM to 5 mM of cloxacillin, and 0.05 M to 1 M phosphate or MES buffer. In another embodiment, the second composition comprises 20 µM to 200 µM of nitrocefin, 1 µM to 1.5 mM of clavulanic acid, and 0.05 M to 1 M phosphate or MES buffer. In another embodiment, the third composition comprises 20 µM to 200 µM of nitrocefin, 20 µM to 5 mM of cloxacillin, 1 µM to 1.5 mM of clavulanic acid, and 0.05 M to 1 M phosphate or MES buffer. In another embodiment, each composition is pH 5 to pH 7. In another embodiment, the fourth composition comprises 20 µM to 200 µM of nitrocefin, 1 µM to 1.5 mM of clavulanic acid and 0.05 M to 1 M phosphate or MES buffer. The first, second and third compositions described in the preceding embodiments may be used independently or together as one of skill in the art will appreciate. In another embodiment, each composition is pH 5 to pH 7. In a specific embodiment, the concentration of inhibitor used in a composition is dependent on the concentration of beta-lactamase substrate in the composition.

In certain embodiments, the compositions used in accordance with the methods described herein comprise a lysis reagent. Lysis reagents (e.g., a lysis reagent in a lysis buffer) are known to one of skill in the art. In a specific embodiment, the lysis reagent lyses the bacterial cells but does not interfere with either the hydrolysis of the beta-lactamase substrate or the activity of one or more beta-lactamase inhibitors, or both. In one embodiment, the lysis reagent is a detergent, such as a mild non-denaturing detergent (e.g., Triton® X-100 or CHAPS). In another embodiment, the lysis reagent is an enzyme or other agent that promotes the lysis of a bacterial cell. Non-limiting examples of such an enzyme include lysozyme, labiase, lysostaphin, achromopeptidase, and mutanolysin. In a particular embodiment, the compositions used in accordance with the methods described herein comprise about 0.1 mg/ml to about 10 mg/ml, about 0.5 mg/ml to about 10 mg/ml, about 1 mg/ml to about 10 mg/ml, about 2 mg/ml to about 10 mg/ml, about 3 mg/ml to about 10 mg/ml, about 4 mg/ml to about 10 mg/ml or about 5 mg/ml to about 10 mg/ml of an enzyme or other agent that promotes the lysis of a bacterial cell. In another embodiment, the compositions used in accordance with the methods described herein comprise about 0.1 mg/ml to about 8 mg/ml, about 1 mg/ml to about 6 mg/ml, about 1 mg/ml to about 5 mg/ml, about 1 mg/ml to about 5 mg/ml, about 2 mg/ml to 4 mg/ml, or about 3 mg/ml of an enzyme or other agent that promotes the lysis of a bacterial cell.

In a specific embodiment, the compositions used in accordance with the methods described herein comprise lysozyme. In a particular embodiment, the compositions used in accordance with the methods described herein comprise about 0.1 mg/ml to about 10 mg/ml, about 0.5 mg/ml to about 10 mg/ml, about 1 mg/ml to about 10 mg/ml, about 2 mg/ml to about 10 mg/ml, about 3 mg/ml to about 10 mg/ml, about 4 mg/ml to about 10 mg/ml or about 5 mg/ml to about 10 mg/ml of lysozyme. In another embodiment, the compositions used in accordance with the methods described herein comprise about 0.1 mg/ml to about 8 mg/ml, about 1 mg/ml to about 6 mg/ml, about 1 mg/ml to about 5 mg/ml, about 1 mg/ml to about 5 mg/ml, about 2 mg/ml to 4 mg/ml, or about 3 mg/ml of lysozyme.

In certain embodiments, the compositions used in accordance with the methods described herein comprise a lysis reagent (e.g., lysozyme, labiase, lysostaphin, achromopeptidase, or mutanolysin) and an agent that promotes the stabilization of the lysis reagent. In a specific embodiment, the agent that promotes the stabilization of the lysis reagent does not interfere with either the hydrolysis of the beta-lactamase substrate or the activity of one or more beta-lactamase inhibitors, or both. In one embodiment, the agent that promotes the stabilization of the lysis reagent is thermal stable. In a specific embodiment, the agent that promotes the stabilization of the lysis reagent is stable at temperatures of about 60° C. or higher, about 50° C. to about 100° C., about 60° C. to about 90° C., about 60° C. to about 85° C., about 60° C. to about 75° C., or about 60° C. to about 70° C. In a particular embodiment, the compositions used in accordance with the methods described herein comprise about 0.1% to about 10%, about 1% to about 10%, about 2% to about 10%, about 4% to about 10%, about 1% to about 8%, about 2% to about 8%, about 2% to about 6%, or about 2% to about 4% of an agent that promotes the stabilization of the lysis reagent.

In a specific embodiment, the compositions used in accordance with the methods described herein comprise a lysis reagent and a carbohydrate, e.g., a monosaccharide, a disaccharide, a polysaccharide, an oligosaccharide, or a polyol. Specific examples of carbohydrates include, but are not limited to mannitol, ribose, glucose, fructose, mannose, sucrose, lactose, glycerol, Xanthan gum, trehalose and glycols (e.g. propylene glycol). In a specific embodiment, the carbohydrate is trehalose.

In a specific embodiment, the compositions used in accordance with the methods described herein comprise lysozyme and trehalose. In a particular embodiment, the compositions used in accordance with the methods described herein comprise about 0.1 mg/ml to about 10 mg/ml, about 0.5 mg/ml to about 10 mg/ml, about 1 mg/ml to about 10 mg/ml, about 2 mg/ml to about 10 mg/ml, about 3 mg/ml to about 10 mg/ml, about 4 mg/ml to about 10 mg/ml or about 5 mg/ml to about 10 mg/ml of lysozyme and about 0.1% to about 10%, about 1% to about 10%, about 2% to about 10%, about 4% to about 10%, about 1% to about 8%, about 2% to about 8%, about 2% to about 6%, or about 2% to about 4% of trehalose. In another embodiment, the compositions used in accordance with the methods described herein comprise about 0.1 mg/ml to about 8 mg/ml, about 1 mg/ml to about 6 mg/ml, about 1 mg/ml to about 5 mg/ml, about 1 mg/ml to about 5 mg/ml, about 2 mg/ml to 4 mg/ml, or about 3 mg/ml of lysozyme and about 0.1% to about 10%, about 1% to about 10%, about 2% to about 10%, about 4% to about 10%, about 1% to about 8%, about 2% to about 8%, about 2% to about 6%, or about 2% to about 4% of trehalose.

In certain embodiments, the compositions used in accordance with the methods described herein comprise a lysis reagent (e.g., lysozyme, labiase, lysostaphin, achromopeptidase, or mutanolysin) and an additional agent, e.g., an agent that enhances the lysis of a bacterial cell by a lysis reagent (e.g., a metal chelator). In certain embodiments, the compositions used in accordance with the methods described herein comprise a lysis reagent (e.g., lysozyme, labiase, lysostaphin, achromopeptidase, or mutanolysin), an agent that promotes the stabilization of the lysis reagent, and an additional agent, e.g., an agent that enhances the lysis of a bacterial cell by a lysis reagent (e.g., a metal chelator). In a specific embodiment, the agent that promotes the stabilization of the lysis reagent does not interfere with either the hydrolysis of the beta-lactamase substrate or the activity of one or more beta-lactamase inhibitors, or both. In specific embodiments, an agent that enhances the lysis of a bacterial cell by a lysis reagent increases rate at which the lysis reagent lyses bacterial cells by about 10%, about 20%, about 25%, about 30%, about 40%, about 50%, about 60% or about 75% relative the rate at which the lysis reagent lyses bacterial cells in the absence of the agent. In other embodiments, an agent that enhances the lysis of a bacterial cell by a lysis reagent increases rate at which the lysis reagent lyses bacterial cells by about 10% to about 50%, about 10% to about 75%, about 25% to about 75%, about 25% to about 50%, about 25% to about 40%, about 25% to about 30% or about 50% or about 75% relative the rate at which the lysis reagent lyses bacterial cells in the absence of the agent. In certain embodiments, the compositions used in accordance with the methods described herein comprise about 0.1 mM to about 5 mM, about 1 mM to about 4 mM, about 1 mM to about 3 mM, about 2 mM to about 3 mM, or about 0.1 to about 2 mM of an agent that enhances the lysis of a bacterial cell by a lysis reagent.

In a specific embodiment, the compositions used in accordance with the methods described herein comprise a lysis reagent, an agent that promotes the stabilization of the lysis reagent, and EDTA or EGTA. In particular embodiments, either EDTA or EGTA, or both are not utilized if a metallo-beta-lactamase is or may be detected.

In a specific embodiment, the compositions used in accordance with the methods described herein comprise a lysozyme, trehalose and EDTA. In a particular embodiment, the compositions used in accordance with the methods described herein comprise about 0.1 mg/ml to about 10 mg/ml, about 0.5 mg/ml to about 10 mg/ml, about 1 mg/ml to about 10 mg/ml, about 2 mg/ml to about 10 mg/ml, about 3 mg/ml to about 10 mg/ml, about 4 mg/ml to about 10 mg/ml or about 5 mg/ml to about 10 mg/ml of lysozyme, about 0.1% to about 10%, about 1% to about 10%, about 2% to about 10%, about 4% to about 10%, about 1% to about 8%, about 2% to about 8%, about 2% to about 6%, or about 2% to about 4% of trehalose, and about 0.1 mM to about 5 mM, about 1 mM to about 4 mM, about 1 mM to about 3 mM, about 2 mM to about 3 mM, or about 0.1 to about 2 mM of EDTA. In another embodiment, the compositions used in accordance with the methods described herein comprise about 0.1 mg/ml to about 8 mg/ml, about 1 mg/ml to about 6 mg/ml, about 1 mg/ml to about 5 mg/ml, about 1 mg/ml to about 5 mg/ml, about 2 mg/ml to 4 mg/ml, or about 3 mg/ml of lysozyme, about 0.1% to about 10%, about 1% to about 10%, about 2% to about 10%, about 4% to about 10%, about 1% to about 8%, about 2% to about 8%, about 2% to about 6%, or about 2% to about 4% of trehalose, and about 0.1 mM to about 5 mM, about 1 mM to about 4 mM, about 1 mM to about 3 mM, about 2 mM to about 3 mM, or about 0.1 to about 2 mM of EDTA.

In some embodiments, the compositions used in accordance with the methods described herein are in the form of a liquid composition, an agar plate, a paper strip, a paper disk, a tablet, a dry form in wells, or a dry form in one or more tubes, e.g., an array of tubes. In some embodiments, the compositions used in accordance with the methods described herein are dried and are present on or in a solid support, such as the well of a plate, a panel, a cassette or a tray, a paper strip, a paper disk, or a tube. As used herein, the term "solid support" in the context of the form of a composition described herein refers to a solid surface that a composition described herein may be dried or adhered to and is suitable for the detection of a beta-lactamase in accordance with the methods presented herein. Non-limiting examples of solid supports include silica gels, resins, derivatized plastic films, glass beads, and polystyrene beads.

In certain embodiments, the compositions used in accordance with the methods described herein are dried onto or in a solid support using heat at temperatures of, e.g., 50° C. to 100° C., 50° C. to 85° C., 50° C. to 75° C., 60° C. to 75° C. or 60° C. to 70° C. In one embodiment, the compositions used in accordance described herein are dried onto or in a solid support using heat under forced air or vacuum conditions at temperatures of, e.g., 50° C. to 100° C., 50° C. to 85° C., 50° C. to 75° C., 60° C. to 75° C. or 60° C. to 70° C. In other embodiments, the compositions used in accordance with the methods described herein are dried onto or in a solid support using a lypholization technique. In other embodiments, the compositions described herein are dried onto or in a solid support using a spray drying technique.

In certain embodiments, the compositions used in accordance with the methods described herein are pre-mixed and dried into the wells of a panel, tray, cassette or plate (e.g., a microtiter plate). In specific embodiments, the compositions used in accordance with the methods described herein are pre-mixed and dried into the wells of a tray, a cassette, a microtiter plate or a panel, such as a well of the Phoenix™ Panel (BD, USA), a well of a panel for the BBL™ Crystal™ Identification System (BD, USA), a Vitek® card (bioMerieux, USA), a well of a MicroScan panel (Dade Behring, USA), or a well of a panel for the Remel RapID™ System (Remel, USA). See, e.g., U.S. Pat. No. 5,922,593 and Des. 421,498 (each of which are incorporated herein by reference) for a description of panels with wells that the compositions described herein may be dried in or on using, e.g., heat at temperatures of, e.g., 50° C. to 100° C., 50° C. to 85° C., 50° C. to 75° C., 60° C. to 75° C. or 60° C. to 70° C. In other embodiments, the compositions used in accordance with the methods described herein are pre-mixed and dried into the tubes, e.g., test tubes or Eppendorf tubes. In a specific embodiment, the compositions used in accordance with the methods described herein are pre-mixed and dried into the tubes for the API biochemical test (bioMerieux, USA).

In a particular embodiment, the compositions used in the accordance with the methods described herein are dried and are present in the wells of a Phoenix™ Panel (BD, USA) and an automated system, such as the BD Phoenix™ Automated Microbiology System (BD, USA), is used to detect substrate utilization. See, e.g., U.S. Pat. Nos. 5,922,593, 6,096,272, 6,372,485 and 7,115,384 (each of which are incorporated herein by reference) for a description of an automated system for detection of substrate utilization. In specific embodiments, a pure bacterial sample resuspended in a saline buffer or broth (e.g., AST broth or ID broth (BD, USA)), is added to a Phoenix™ panel (BD. USA) with individual wells comprising a composition described herein, the panel is incubated for a period of time in the BD Phoenix™ Automated Microbiology System (BD, USA) and substrate utilization is detect at different time points.

In another embodiment, the compositions used in accordance with the methods described herein are dried and present in the wells of a panel for the BBL™ Crystal™ Identification System (BD, USA) and an automated system, such as the BBL™ Crystal™ Identification System (BD, USA), is used to detect substrate utilization. In another embodiment, the compositions used in the accordance with the methods described herein are dried and are present in the wells of a Vitek® card (bioMerieux, USA) and an automated system, such as the Vitek® system (bioMerieux, USA), is used to detect substrate utilization. In another embodiment, the compositions used in the accordance with the methods described herein are dried and are present in the wells of a MicroScan panel (Dade Behring, USA) and an automated system, such as the MicroScan Walk-Away® system (Dade Behring, USA), is used to detect substrate utilization.

In another embodiment, the compositions used in accordance with the methods described herein are in the form of a tablet. The tablet and a bacterial cell suspension may be combined in any type of suitable container (e.g., the wells of microtiter plate, a test tube or an Eppendorf tube), and substrate utilization may be detected by an appropriate technique or device which will vary depending on the substrate chosen.

In another embodiment, the compositions used in accordance with the methods described herein are in the faint of a dry powder. The dry powder and a bacterial cell suspension may be combined in any type of suitable container (e.g., the wells of microtiter plate, a test tube or an Eppendorf tube), and substrate utilization may be detected by an appropriate technique or device which will vary depending on the substrate chosen.

Different compositions for use in detecting the presence of particular beta-lactamases can be contacted with a bacterial sample from the same source simultaneously or sequentially. In a specific embodiment, different compositions (e.g., a first composition and a second composition) are contacted with a bacterial sample from the same source within about 1 minute to about 15 minutes, about 1 minute to about 10 minutes, about 1 minute to about 5 minutes, about 2 seconds to about 60 seconds, about 2 seconds to about 45 seconds, about 2 seconds to about 30 seconds, about 5 second to about 60 seconds or about 5 second to about 30 seconds of each other. In another embodiment, different compositions (e.g., a first composition and a second composition) are contacted with a bacterial sample from the same source within about 15 minutes, about 10 minutes, about 5 minutes, about 4 minutes, about 2 minutes or about 1 minute of each other.

In some embodiments, in addition to a bacterial sample to be tested for the presence of particular beta-lactamases, a bacterial sample that is known to express one or more particular beta-lactamases (i.e., a positive control) is included in the methods presented herein. In other embodiments, in addition to a bacterial sample to be tested for the presence of particular beta-lactamases, a bacterial sample that is known to not express one or more particular beta-lactamases (i.e., a negative control) is included in the methods presented herein. In yet other embodiments, in addition to a bacterial sample to be tested for the presence of particular beta-lactamases, a bacterial sample that is known to express one or more particular beta-lactamases (i.e., a positive control) and a bacterial sample that is known to not express one or more particular beta-lactamases (i.e., a negative control) are included in the methods presented herein. For example, a positive control for an AmpC beta-lactamase can be ATCC No. 700603 and a negative control can be ATCC No. 25922. Positive and negative controls for the assays described herein may be identified using molecular and/or biochemical methods, such as sequencing, to determine the expression of a particular beta-lactamase by a particular bacterial strain.

Generally, the bacterial samples contacted with the different compositions utilized as part of the methods presented herein are from the same source. In some embodiments, a bacterial sample contacted with a composition in accordance with the methods presented herein is a pure bacterial sample. In certain other embodiments, a bacterial sample contacted with a composition in accordance with the methods presented herein is a sample from a bacterial culture, which was inoculated with a sample from a particular source, such as a patient specimen, and incubated for a period of time to allow the bacteria to proliferate. In one embodiment, the bacterial sample contains at least the minimum amount of bacteria required to detect substrate utilization of a detectable beta-lactamase substrate. In a specific embodiment, a bacterial sample comprises at least $10^3$ colony forming units (CFU)/ml, preferably at least $10^5$ CFU/ml, more preferably at least $10^6$, and most preferably at least $10^7$ CFU/ml of bacteria. In another embodiment, a bacterial sample comprises about $10^3$ CFU/ml to about $10^{12}$ CFU/ml, about $10^5$ CFU/ml to about $10^{12}$ CFU/ml, about $10^6$ CFU/ml to about $10^{12}$ CFU/ml, or about $10^7$ CFU/ml to about $10^{12}$ CFU/ml of bacteria. In a particular embodiment, a bacterial sample comprises about $10^7$ CFU/ml to about $10^{10}$ CFU/ml of bacteria. In one embodiment, approximately the same number of bacteria are in each bacterial sample contacted with each of the compositions. In a specific embodiment, approximately the same amount of CFU are contacted with each of the compositions.

In some embodiments, a bacterial sample is a sample of bacteria that is added to a buffer, sterile water, saline or a broth (e.g., AST broth or ID broth (BD, USA)) to make a cell suspension. In one embodiment, the same amount of the cell suspension is contacted with each of the compositions. In a specific embodiment, the turbidity of the cell suspension contacted with each composition is within an acceptable range for the device utilized to detect substrate utilization. In another embodiment, the turbidity of the cell suspension contacted with each of the compositions is about 0.1 to about 3, about 0.2 to about 2.5 or about 0.2 to about 2 as measured by a Dade Behring Microscan turbidity reader. In another embodiment, the turbidity of the cell suspension contacted with each of the compositions is about 0.1 to about 4, about 0.2 to about 5, or about 0.25 to about 4 MacFarland as measured by PhoenixSpec. In another embodiment, the turbidity of the cell suspension contacted with each of the compositions is about 0.1 to about 5, about 0.1 to about 4, about 0.2 to about 5, or about 0.25 to about 4 MacFarland as measured by PhoenixSpec after being diluted about 5 to 10 times. In another embodiment, the turbidity of the cell suspension contacted with each of the compositions is about 0.4 to about 0.8, about 0.5 to about 0.7, or about 0.5 to about 0.6 MacFarland as measured by PhoenixSpec (BD, USA).

In a specific embodiment, the concentration of the same inhibitor present in more than one, two or more of the compositions is the same or similar (within about 10% of each other). In another, the concentration of detectable beta-lactamase substrate is the same or similar (i.e. within about 10% of each other) in all of the compositions. In another embodiment, each composition utilized in any method presented herein is about pH 5 to about pH 8, preferably about pH 5.5 to about pH 7.5, and more preferably pH 6 to about pH 7. In a specific embodiment, each composition has the same or a similar (i.e., within about 10% or about 5% of each other) pH.

In a specific embodiment, the contacting step of the methods presented herein is conducted at about 20° C. to about 42° C., more preferably about 25° C. to about 40° C., and most preferably about 37° C. In another embodiment, each of the compositions is contacted with a bacterial sample from the same source in accordance with the methods presented herein at the same or approximately the same (i.e., within 5° C.) temperature.

The detection step of the methods presented herein may be performed for the minimum amount of time needed for enough substrate to be utilized by a bacterial sample positive for beta-lactamase to allow detection by a standard method for a particular detectable substrate (e.g., visual observation and/or spectrophotometry for a chromogenic beta-lactamase substrate).

In a particular embodiment, the detection step of the methods presented herein is performed about 2 minutes to about 60 minutes, preferably about 2 minutes to about 45 minutes or about 2 minutes to about 30 minutes, more preferably about 2 minutes to about 15 minutes, and most preferably about 2 minutes to about 10 minutes after the contacting step. In another embodiment, the detection step of the methods presented herein is performed about 15 minutes to about 5 hours, about 30 minutes to about 5 hours, about 30 minutes to about 4 hours, about 30 minutes to about 5 hours, about 1 hour to about 2 hours, about 1 hour to about 3 hours, about 1 hour to about 4 hours, about 1 hour to about 5 hours, about 2 hours to about 4 hours, about 2 hours to about 5 hours, or about 2 hours to about 6 hours after the contacting step. In another embodiment, the detection step of the methods presented herein is performed at different time points over about 24 hours, about 20 hours, about 18 hours, about 16 hours, about 12 hours, about 8 hours, about 4 hours, about 2 hours or about 1 hour. In a specific embodiment, the detection step is performed after each bacterial sample from the same source is contacted with each composition for the same amount of time.

In some embodiments, the rate of substrate utilization when bacterial samples from the same source are contacted with different compositions is compared. In a specific embodiment, a spectrophotometer that has software to calculate the rate of substrate utilization is used. The enzymatic activity of different beta-lactamases may be affected differently by the concentration of detectable beta-lactamase substrate included in a composition, the concentration and type of inhibitors included in a composition, the pH of the composition, and the temperature at which the contacting step is conducted. For example, a serine carbapenemase can utilize a beta-lactamase substrate present in a composition comprising cloxacillin at a similar rate as a beta-lactamase substrate present in a composition comprising cloxacillin and clavulanic acid. On the other hand, a metallo-beta-lactamase can utilize a beta-lactamase substrate faster than it can utilize a beta-lactamase substrate present in a composition comprising a beta-lactamase substrate and a metal chelator.

In some embodiments, a qualitative difference between the compositions is compared when determining substrate utilization. For example, if a chromogenic beta-lactamase substrate, such as nitrocefin, is used in the compositions, whether or not the compositions turn a particular color (e.g., red for nitrocefin) may be assessed. In other embodiments, a quantitative difference between the compositions is compared when determining substrate utilization. For example, if nitrocefin, a chromogenic beta-lactamase substrate, is used in the compositions, the percentage of the substrate that turns red may be assessed.

The particular technique used to assess substrate utilization will vary depending upon the substrate chosen. For example, if the detectable beta-lactamase substrate is a chromogenic substrate (e.g., nitrocefin or PADAC®), then substrate utilization can be assessed by visual observation or spectrophotometry (at, e.g., a wavelength of 492 nm or 390 nm for nitrocefin). In particular, the hydrolysis of nitrocefin can be, for example, detected by visually observing the color of the substrate turning from yellow to red. The hydrolysis of PADAC® can be detected by visually observing the color of the substrate turning from violet to yellow. If the detectable beta-lactamase substrate is a fluorogenic substrate, then substrate utilization can be detected by measuring the fluorescence of the substrate. Different antibiotics have different wavelengths and the use of an antibiotic as a substrate by a bacterial species will result in a change in the wavelength of the composition. Thus, in some embodiments, a spectrophometer is used to monitor changes in the wavelength of a composition comprising an antibiotic as the beta-lactamase substrate.

In specific embodiments, the BD Phoenix™ Automated Microbiology System (BD, USA) is used to assess substrate utilization. In other embodiments, the Vitek® 2 automated system (bioMerieux, USA) is used to assess substrate utilization. In other embodiments, the MicroScan Walk-Away® automated system (Dade Behring, USA) is used to assess substrate utilization.

4.2 Compositions for Use in the Beta-Lactamase Assays

Compositions for use in the detection of particular beta-lactamases can comprise a detectable beta-lactamase substrate. Any beta-lactamase substrate that is readily detectable may be used in the compositions presented herein. Non-limiting examples of detectable beta-lactamase substrates include chromogenic substrates, fluorogenic substrates, and antibiotics. Chromogenic beta-lactamase substrates include, but are not limited to, nitrocefin (3-[2,4-dinitrostyryl]-7-(2-thienylacetamido]3-cephem-4-carobxylic acid (Calbiochem, San Diego, Calif.)), PADAC® (Pyridinium-2-azo-p-dimethylaniline chromophore (Calbiochem. San Diego, Calif.)), CENTA™ (EMD Chemicals, Inc., San Diego, Calif.), HMRZ-86 ((7R)-7[2-aminothiazol-4-yl]-(z)-2-(1-carboxy-1-methylethoxyimino)acetamido)-3-(2,4-dinitrostyryl)-3-cephem-4-carboxylic acid trifluoroacetate, E-isomer (Kanto Chemical Co., Inc. Tokyo, Japan)), and cefesone. Fluorogenic substrates include, but are not limited to, Fluorcillin Green 495/525 and Fluorocillin Green 345/350 LIVE BLAZER™-FRET B/G (Invitrogen, Carlsbad, Calif.). Antibiotics include beta-lactams, penicillin, amoxicillin, etc. In a specific embodiment, the concentration of substrate that exhibits substrate utilization as detected by a technique know to one of skill in the art, such as spectrophotometry and visual observation, is used in the compositions presented herein.

In a specific embodiment, the detectable beta-lactamase substrate is nitrocefin. In a particular embodiment, nitrocefin is present in a composition described herein at a concentration of about 1 µM to about 1 mM, about 1 µM to about 750 µM, about 1 µM to about 500 µM, or about 1 to about 250 µM. In another embodiment, nitrocefin is present in a composition described herein at a concentration of about 20 µM to about 200 µM.

In another embodiment, the detectable beta-lactamase substrate is CENTAT™. In a particular embodiment, CENTA™ is present in a composition described herein at a concentration of about 1 µM to about 1 mM, about 1 µM to about 750 µM, about 1 µM to about 500 µM, or about 1 µM to about 250 µM. In another embodiment, CENTA™ is present in a composition described herein at a concentration of about 20 µM to about 200 µM.

In another embodiment, the detectable beta-lactamase substrate is HMRZ-86. In a particular embodiment, HMRZ-86 is present in a composition described herein at a concentration of about 1 µM to about 1 mM, about 1 µM to about 750 µM, about 1 µM to about 500 µM, or about 1 µM to about 250 µM. In another embodiment, HMRZ-86 is present in a composition described herein at a concentration of about 20 µM to about 200 µM.

In addition to a detectable beta-lactamase substrate, the compositions for use in the methods presented herein may comprise one, two or more of the following beta-lactamase inhibitors: an AmpC inhibitor, a serine beta-lactamase inhibitor, a metal chelator and an ESBL inhibitor. In a specific embodiment, a composition comprises a detectable beta-lactamase substrate and an AmpC inhibitor. In another embodiment, a composition comprises a detectable beta-lactamase substrate, an AmpC inhibitor and a serine beta-lactamase inhibitor in an amount sufficient to inhibit ESBL and an OSBL but not a class A serine carbapenemase. In another embodiment, a composition comprises a detectable beta-lactamase substrate, an AmpC inhibitor, a serine beta-lactamase inhibitor in an amount sufficient to inhibit ESBL and an OSBL but not a class A serine carbapenemase, and a metal chelator. In another embodiment, a composition comprises a detectable beta-lactamase substrate and a serine beta-lactamase inhibitor in an amount sufficient to inhibit ESBL and an OSBL but not a class A serine carbapenemase. In another embodiment, a composition comprises a detectable beta-lactamase substrate and a metal chelator. In another embodiment, a composition comprises a detectable beta-lactamase substrate and an ESBL inhibitor. As one of skill in the art will appreciate, the concentration of bacteria and the concentration of detectable beta-lactamase substrate will affect the concentration of an inhibitor added to a composition. Further, one of skill in the art will be able to routinely determine the concentration range of an inhibitor to use in a composition empirically by contacting a positive control bacterial sample (and optimally a negative control bacterial sample) with different compositions, each composition comprising different combinations of detectable beta-lactamase substrate and/or inhibitor.

As used herein, the term "AmpC inhibitor" refers to an agent that at particular concentrations inhibits the enzymatic activity of AmpC, but not the enzymatic activity of serine carbapenemases, metallo-beta-lactamases, OSBL and ESBL. Non-limiting examples of an AmpC inhibitor include cloxacillin (VWR, Pennsylvania, USA), salt forms of cloxacillin, syn2190 (NAEJA Pharmaceutical, Inc., Edmonton, Alberta, Canada), salt forms of cloxacillin (such as a sodium or potassium salt form of cloxacillin), aztreonam (VWR, Pennsylvania, U.S.A.) and boronic acid and its derivatives thereof (Focus Synthesis LLC, San Diego, Calif.), and a combination thereof. In one embodiment, the AmpC inhibitor is cloxacillin. In a specific embodiment, a composition comprising an AmpC inhibitor contains about 1 µM to about 100 mM, about 1 µM to about 75 mM, about 1 µM to about 50 mM, about 1 µM to about 25 mM, about 1 µM to about 10 mM, or about 1 µM to about 5 mM of an AmpC inhibitor. In another embodiment, a composition comprising an AmpC inhibitor contains about 100 µM to about 4 mM, about 200 µM to about 4 mM, 500 µM to about 4 mM, about 750 µM to about 4 mM, or about 1 mM to about 4 mM of an AmpC inhibitor. In another embodiment, a composition comprising an AmpC inhibitor contains about 500 µM to about 3 mM, about 1 mM to about 3 mM, about 1.5 mM to about 3 mM, or about 2 mM to about 3 mM of an AmpC inhibitor. In a particular embodiment, the AmpC inhibitor is cloxacillin. In a specific embodiment, a composition comprises about 20 µM to about 5 mM of cloxacillin or a salt form thereof.

As used herein, the term "serine beta-lactamase inhibitor" refers to an agent that at particular concentrations inhibits the enzymatic activity of ESBLs and OSBLs, but not class A serine carbapenemases and AmpC. Non-limiting examples of a serine beta-lactamase inhibitor include clavulanic acid (GlaxoSmithKline, UK), salt forms of clavulanic acid (such as a sodium salt form of clavulanic acid), tazobactum (Wyeth Ayerst Research, New York, U.S.A.), sulbactam (Pfizer, New York, U.S.A.), and a combination thereof. In one embodiment, the serine beta-lactamase inhibitor is clavulanic acid. In a specific embodiment, a composition comprising clavulanic acid or a salt form thereof in an amount sufficient to inhibit an ESBL and an OSBL but not a class A serine carbapenemase contains about 10 µM to about 100 mM, about 10 µM to about 75 mM, about 10 µM to about 50 mM, about 10 µM to about 25 mM, about 10 µM to about 10 mM, or about 10 µM to about 5 mM of clavulanic acid or a salt form thereof. In another embodiment, a composition comprising clavulanic acid or a salt form thereof in an amount sufficient to inhibit an ESBL and an OSBL but not a class A serine carbapenemase contains about 10 µM to about 2 mM, about 25 µM to about 2 mM, 50 µM to about 2 mM, about 75 µM to about 2 mM, or about 100 µM to about 2 mM of clavulanic acid or a salt form thereof. In another embodiment, a composition comprising clavulanic acid or a salt form thereof in an amount sufficient to inhibit an ESBL and an OSBL but not a class A serine carbapenemase contains about 200 µM to about 2 mM, about 250 µM to about 2 mM, about 300 µM to about 2 mM, about 400 µM to about 2 mM, or about 500 µM to about 2 mM of clavulanic acid or a salt form thereof. In another embodiment, a composition comprising clavulanic acid or a salt form thereof in an amount sufficient to inhibit an ESBL and an OSBL but not a class A serine carbapenemase contains about 1 µM to about 2 mM, about 1 µM to about 1.5 mM, about 1 µM to about 1 mM, about 1 µM to about 750 µM, about 1 µM to about 500 µM, about 1 µM to about 250 µM, or about 1 µM to 50 µM of clavulanic acid or a salt form thereof. In a particular embodiment, a composition comprising clavulanic acid or a salt form thereof in an amount sufficient to inhibit an ESBL and an OSBL but not a class A serine carbapenemase contains about 500 µM to about 1.5 mM of clavulanic acid or a salt form thereof. In one embodiment, the serine beta-lactamase inhibitor is tazobactum. In a specific embodiment, a composition comprising tazobactum or a salt form thereof in an amount sufficient to inhibit an ESBL and an OSBL but not a class A serine carbapenemase contains about 100 µM to about 1 mM, about 100 µM to about 750 µM, about 100 µM to about 500 µM, or about 100 µM to about 250 µM of tazobactum or a salt form thereof. In another embodiment, the serine beta-lactamase inhibitor is sulbactam. In a specific embodiment, a composition comprising sulbactam or a salt form thereof in an amount sufficient to inhibit an ESBL and an OSBL but not a class A serine carbapenemase contains about 100 µM to about 5 mM, about 100 µM to about 4 mM, about 100 µM to about 3 mM, about 100 µM to about 2 mM, or about 100 µM to about 1 mM of sulbactam or a salt form thereof. In another embodiment, a composition comprising sulbactam or a salt form thereof in an amount sufficient to inhibit an ESBL and an OSBL but not a class A serine carbapenemase contains about 100 µM to about 750 µM, about 100 µM to about 500 µM, 100 µM to about 250 µM, about 100 µM to about 200 mM, or about 100 µM to about 150 µM of sulbactam or a salt form thereof.

Non-limiting examples of a metal chelator include dipicolinic acid (DPC), diethyldithiocarbamate (DEDTC), N,N, N',N'-tetrakis-(2-pyridylmethyl)-ethylenediamine (TPEN) (VWR, Pennsylvania, U.S.A.), EDTA (VWR, Pennsylvania, U.S.A.), 2,3-dimercapto-1-propane sulfonic acid (DMPS) (Sigma, St. Louis, Mo., U.S.A.) and 1,10-phenanthroline (Sigma, St. Louis, Mo., U.S.A.). In a specific embodiment, the metal chelator is zinc-specific. TPEN is a non-limiting example of a zinc-specific metal chelator. In alternative embodiment, the metal chelator is able to bind to zinc but is not zinc-specific. DMPS, EDTA, 1,10-phenanthroline, DPC and DEDTC are non-limiting examples of metal chelators that are not zinc-specific. In a preferred embodiment, the metal chelator is membrane permeable. In some embodiments, a composition comprise EDTA, DMPS, 1,10-phenanthroline, DPC, DEDTC or TPEN at a concentration of about 0.5 mM to about 200 mM, about 1 mM to about 100 mM, or about 1 mM to about 50 mM. In a specific embodiment, a composition comprises DPC at a concentration of about 0.5 mM to about 10 mM, about 0.5 mM to about 7 mM, about 0.5 mM to about 5 mM, about 0.5 mM to about 2 mM or about 0.5 mM to about 1 mM. In another embodiment, a composition comprises DEDTC at a concentration of about 1 mM to about 20 mM, about 1 mM to about 15 mM, about 1 mM to about 10 mM, about 1 mM to about 7 mM, about 1 mM to about 5 mM or about 1 mM to about 2 mM.

As used herein, the term "ESBL inhibitor" refers to an agent that at particular concentrations inhibits the enzymatic activity of ESBLs, but not the enzymatic activity of OSBLs. Non-limiting examples of an ESBL inhibitor include ceftazidime (GlaxoSmithKline, UK), a salt form of ceftazidime, cefotaxime (MP Biomedicals, Solon, Ohio, U.S.A.), a salt form of cefotaxime and a combination thereof. In one embodiment, the ESBL inhibitor is ceftazidime. In a specific embodiment, a composition comprises ceftazidime or a salt form thereof at a concentration of about 1 mM to about 20 mM, about 1 mM to about 15 mM, about 1 mM to about 10 mM, about 1 mM to about 7 mM, about 1 mM to about 5 mM, or about 1 mM to about 2 mM. In another embodiment, the ESBL inhibitor is cefotaxime or a salt form thereof. In a specific embodiment, a composition comprises cefotaxime or a salt form thereof at a concentration of about 1 mM to about 20 mM, about 1 mM to about 15 mM, about 1 mM to about 10 mM, about 1 mM to about 7 mM, about 1 mM to about 5 mM, or about 1 mM to about 2 mM. In another embodiment, the ESBL inhibitor is a combination of ceftazidime and cefotaxime. In a specific embodiment, a composition comprises a combination of ceftazidime or a salt form thereof and cefotaxime or a salt form thereof at a concentration of about 1 mM to about 20 mM, about 1 mM to about 15 mM, about 1 mM to about 10 mM, about 1 mM to about 7 mM, about 1 mM to about 5 mM, or about 1 mM to about 2 mM.

In addition to a detectable beta-lactamase substrate and one or more beta-lactamase inhibitors, the compositions for use in the detection of one or more beta-lactamases may include a buffer. Any buffer that aids in maintaining the pH of the composition and does not interfere with either the hydrolysis of the beta-lactamase substrate or the activity of one or more beta-lactamase inhibitors, or both may be used. Non-limiting examples of buffers include phosphate MES buffer, acetate buffer, Tris buffer, ADA buffer, MDPS buffer, and HEPES buffer. In a specific embodiment, a composition comprises 0.05 to 1 ml of phosphate or MES buffer.

In some embodiments, in addition to a detectable beta-lactamase substrate and one or more beta-lactamase inhibitors, the compositions comprise an agent such as an enzyme, non-ionic detergent or EDTA to facilitate the rupture of the cell wall of the bacteria. As one of skill in the art will appreciate, the use of EDTA in a composition presented herein, may, depending upon the concentration, inhibit metallo-beta-lactamases. Accordingly, one of skill in the art should consider this before adding EDTA to a composition presented herein. In a preferred embodiment, the compositions do not comprise an additional agent that facilitates the rupture of cell wall of the bacteria.

In certain embodiments, in addition to a detectable beta-lactamase substrate and one or more beta-lactamase inhibitors, the compositions described herein comprise a lysis reagent. Lysis reagents are known to one of skill in the art. In a specific embodiment, the lysis reagent lyses the bacterial cells but does not interfere with either the hydrolysis of the beta-lactamase substrate or the activity of one or more beta-lactamase inhibitors, or both. In one embodiment, the lysis reagent is a detergent, such as a mild non-denaturing detergent (e.g., Triton® X-100 or CHAPS). In another embodiment, the lysis reagent is an enzyme or other agent that promotes the lysis of a bacterial cell. Non-limiting examples of such an enzyme include lysozyme, labiase, lysostaphin, achromopeptidase, and mutanolysin. In a particular embodiment, the compositions described herein comprise about 0.1 mg/ml to about 10 mg/ml, about 0.5 mg/ml to about 10 mg/ml, about 1 mg/ml to about 10 mg/ml, about 2 mg/ml to about 10 mg/ml, about 3 mg/ml to about 10 mg/ml, about 4 mg/ml to about 10 mg/ml or about 5 mg/ml to about 10 mg/ml of an enzyme or other agent that promotes the lysis of a bacterial cell. In another embodiment, the compositions described herein comprise about 0.1 mg/ml to about 8 mg/ml, about 1 mg/ml to about 6 mg/ml, about 1 mg/ml to about 5 mg/ml, about 1 mg/ml to about 5 mg/ml, about 2 mg/ml to 4 mg/ml, or about 3 mg/ml of an enzyme or other agent that promotes the lysis of a bacterial cell.

In a specific embodiment, the compositions described herein comprise lysozyme. In a particular embodiment, the compositions described herein comprise about 0.1 mg/ml to about 10 mg/ml, about 0.5 mg/ml to about 10 mg/ml, about 1 mg/ml to about 10 mg/ml, about 2 mg/ml to about 10 mg/ml, about 3 mg/ml to about 10 mg/ml, about 4 mg/ml to about 10 mg/ml or about 5 mg/ml to about 10 mg/ml of lysozyme. In another embodiment, the compositions described herein comprise about 0.1 mg/ml to about 8 mg/ml, about 1 mg/ml to about 6 mg/ml, about 1 mg/ml to about 5 mg/ml, about 1 mg/ml to about 5 mg/ml, about 2 mg/ml to 4 mg/ml, or about 3 mg/ml of lysozyme.

In certain embodiments, the compositions described herein comprise a lysis reagent (e.g., lysozyme, labiase, lysostaphin, achromopeptidase, or mutanolysin) and an agent that promotes the stabilization of the lysis reagent. In a specific embodiment, the agent that promotes the stabilization of the lysis reagent does not interfere with either the hydrolysis of the beta-lactamase substrate or the activity of one or more beta-lactamase inhibitors, or both. In one embodiment, the agent that promotes the stabilization of the lysis reagent is thermal stable. In a particular embodiment, the compositions described herein comprise about 0.1% to about 10%, about 1% to about 10%, about 2% to about 10%, about 4% to about 10%, about 1% to about 8%, about 2% to about 8%, about 2% to about 6%, or about 2% to about 4% of an agent that promotes the stabilization of the lysis reagent.

In a specific embodiment, the compositions described herein comprise a lysis reagent and a carbohydrate, e.g., a monosaccharide, a disaccharide, a polysaccharide, an oligosaccharide, or a polyol. Specific examples of carbohydrates include, but are not limited to, mannitol, ribose, glucose, fructose, mannose, sucrose, lactose, glycerol. Xanthan gum, trehalose and glycols (e.g., propylene glycol). In a specific embodiment, the carbohydrate is trehalose.

In a specific embodiment, the compositions described herein comprise lysozyme and trehalose. In a particular embodiment, the compositions described herein comprise about 0.1 mg/ml to about 10 mg/ml, about 0.5 mg/ml to about 10 mg/ml, about 1 mg/ml to about 10 mg/ml, about 2 mg/ml to about 10 mg/ml, about 3 mg/ml to about 10 mg/ml, about 4 mg/ml to about 10 mg/ml or about 5 mg/ml to about 10 mg/ml of lysozyme and about 0.1% to about 10%, about 1% to about 10%, about 2% to about 10%, about 4% to about 10%, about 1% to about 8%, about 2% to about 8%, about 2% to about 6%, or about 2% to about 4% of trehalose. In another embodiment, the compositions described herein comprise about 0.1 mg/ml to about 8 mg/ml, about 1 mg/ml to about 6 mg/ml, about 1 mg/ml to about 5 mg/ml, about 1 mg/ml to about 5 mg/ml, about 2 mg/ml to 4 mg/ml, or about 3 mg/ml of lysozyme and about 0.1% to about 10%, about 1% to about 10%, about 2% to about 10%, about 4% to about 10%, about 1% to about 8%, about 2% to about 8%, about 2% to about 6%, or about 2% to about 4% of trehalose.

In certain embodiments, the compositions described herein comprise a lysis reagent (e.g., lysozyme, labiase, lysostaphin, achromopeptidase, or mutanolysin) and an additional agent, e.g., an agent that enhances the lysis of a bacterial cell by a lysis reagent (e.g., a metal chelator). In certain embodiments, the compositions described herein comprise a lysis reagent (e.g., lysozyme, labiase, lysostaphin, achromopeptidase, or mutanolysin), an agent that promotes the stabilization of the lysis reagent, and an additional agent, e.g., an agent that enhances the lysis of a bacterial cell by a lysis reagent (e.g., a metal chelator). In a specific embodiment, the agent that enhances the lysis of a bacterial cell by a lysis reagent does not interfere with either the hydrolysis of the beta-lactamase substrate or the activity of one or more beta-lactamase inhibitors, or both. In specific embodiments, an agent that enhances the lysis of a bacterial cell by a lysis reagent increases rate at which the lysis reagent lyses bacterial cells by about 10%, about 20%, about 25%, about 30%, about 40%, about 50%, about 60% or about 75% relative the rate at which the lysis reagent lyses bacterial cells in the absence of the agent. In other embodiments, an agent that enhances the lysis of a bacterial cell by a lysis reagent increases rate at which the lysis reagent lyses bacterial cells by about 10% to about 50%, about 10% to about 75%, about 25% to about 75%, about 25% to about 50%, about 25% to about 40%, about 25% to about 30% or about 50% or about 75% relative the rate at which the lysis reagent lyses bacterial cells in the absence of the agent. In one embodiment, the compositions described herein comprise about 0.1 mM to about 5 mM, about 1 mM to about 4 mM, about 1 mM to about 3 mM, about 2 mM to about 3 mM, or about 0.1 to about 2 mM of an agent that enhances the lysis of a bacterial cell by a lysis reagent.

In a specific embodiment, the compositions described herein comprise a lysis reagent (e.g., lysozyme, labiase, lysostaphin, achromopeptidase, or mutanolysin), an agent that promotes the stabilization of the lysis reagent, and EDTA or EGTA. In particular embodiments, either EDTA or EGTA, or both are not utilized if a metallo-beta-lactamase is or may be detected.

In a specific embodiment, the compositions described herein comprise a lysozyme, trehalose and EDTA. In a particular embodiment, the compositions described herein comprise about 0.1 mg/ml to about 10 mg/ml, about 0.5 mg/ml to about 10 mg/ml, about 1 mg/ml to about 10 mg/ml, about 2 mg/ml to about 10 mg/ml, about 3 mg/ml to about 10 mg/ml, about 4 mg/ml to about 10 mg/ml or about 5 mg/ml to about 10 mg/ml of lysozyme, about 0.1% to about 10%, about 1% to about 10%, about 2% to about 10%, about 4% to about 10%, about 1% to about 8%, about 2% to about 8%, about 2% to about 6%, or about 2% to about 4% of trehalose, and about 0.1 mM to about 5 mM, about 1 mM to about 4 mM, about 1 mM to about 3 mM, about 2 mM to about 3 mM, or about 0.1 to about 2 mM of EDTA. In another embodiment, the compositions described herein comprise about 0.1 mg/ml to about 8 mg/ml, about 1 mg/ml to about 6 mg/ml, about 1 mg/ml to about 5 mg/ml, about 1 mg/ml to about 5 mg/ml, about 2 mg/ml to 4 mg/ml, or about 3 mg/ml of lysozyme, about 0.1% to about 10%, about 1% to about 10%, about 2% to about 10%, about 4% to about 10%, about 1% to about 8%, about 2% to about 8%, about 2% to about 6%, or about 2% to about 4% of trehalose, and about 0.1 mM to about 5 mM, about 1 mM to about 4 mM, about 1 mM to about 3 mM, about 2 mM to about 3 mM, or about 0.1 to about 2 mM of EDTA.

The compositions can be any form amenable to detection of substrate utilization following contact of a composition with a bacterial sample. For example, the compositions may be in the form of a liquid composition, a tablet, embedded in an agar plate, a paper disk, a paper strip, a dry form in wells, or a dry form in one or more tubes. In a specific embodiment, the compositions are liquid compositions with each liquid composition comprising a detectable beta-lactamase substrate and one or more different beta-lactamase inhibitors. The use of liquid compositions is exemplified in the examples provided in Section 6, infra.

In some embodiments, the compositions are dried and are present on or in a solid support, such as the well of a plate, a panel, a cassette or a tray, a paper strip, a paper disk or a tube. In certain embodiments, the compositions are dried onto or in the solid support using heat at temperatures of, e.g., 50° C. to 100° C., 50° C. to 85° C., 50° C. to 75° C., 60° C. to 75° C. or 60° C. to 70° C. In one embodiment, the compositions are dried onto or in the solid support using heat under forced air or vacuum conditions at temperatures of, e.g., 50° C. to 100° C., 50° C. to 85° C., 50° C. to 75° C. 60° C. to 75° C. or 60° C. to 70° C. In other embodiments, the compositions are dried onto or in the solid support using a lypholization technique. In other embodiments, the compositions are dried onto or in the solid support using a spray drying technique.

In another embodiment, the compositions are part of one agar plate that is divided up into different sections with each section comprising a different composition. For example, the agar plate may comprise three sections with each section comprising a composition comprising a detectable beta-lactamase substrate and one or more different beta-lactamase inhibitors. In another embodiment, there is only one composition per agar plate. In other words, each agar plate only comprises one composition so that two or more agar plates comprising different compositions are utilized in the methods presented herein.

In another embodiment, the compositions are part of a paper disk or paper strip that is divided up into different sections with each section comprising a different composition. For example, the paper disk or paper strip may comprise three sections with each section comprising a composition comprising a detectable beta-lactamase substrate and one or more different beta-lactamase inhibitors. In another embodiment, there is only one composition per paper disk or paper strip. In other words, each paper disk or paper strip only comprises one composition so that two or more paper disks or paper strips comprising different compositions are utilized in the methods presented herein. In a specific embodiment, the paper disk or paper strip is filter paper. In another specific embodiment, the compositions are presented in a form similar to BBL™ Dryslide™ Nitrocefin (Becton Dickinson, Diagnostic Systems, USA).

In certain embodiments, the compositions described herein are dried and are present in the wells of a panel, tray, cassette or plate (e.g., a microtiter plate). In specific embodiments, the compositions described herein are dried and are present in the wells of a tray or panel, such as a well of the Phoenix™ Panel (BD, USA), a well of a panel for the BBL™ Crystal™ Identification System (BD, USA), a Vitek® card (bioMerieux, USA), a well of a MicroScan panel (Dade Behring, USA), or a well of a panel for the Remel RapID™ System (Remel, USA). See, e.g., U.S. Pat. No. 5,922,593 and Des. 421,498 (each of which are incorporated herein by reference) for a description of panels with wells that the compositions described herein may be dried in or on using, e.g., heat. In some embodiments, the compositions described herein are dried and are present in a tube, such as a tube for the API biochemical test (bioMerieux, USA).

In a particular embodiment, the compositions described herein are dried and are present in the wells of a Phoenix™ Panel (BD, USA) and an automated system, such as the BD Phoenix™ Automated Microbiology System (BD, USA), is used to detect substrate utilization. See, e.g., U.S. Pat. Nos. 5,922,593, 6,372,485, 6,096,272, and 7,115,384 (each of which are incorporated herein by reference) for a description of an automated system for detection of substrate utilization. In a particular embodiment, the compositions described herein are dried and are present in the wells of a panel for the BBL™ Crystal™ Identification System (BD, USA) and an automated system, such as the BD BBL™ Crystal Identification System (BD, USA), is used to detect substrate utilization.

In other embodiments, the compositions are dried and are present in the wells of a Vitek® (bioMerieux, USA) and an automated system, such the bioMerieux Vitek® system (bioMerieux, USA), is used to detect substrate utilization. In other embodiments, the compositions are dried and are present in the wells of a MicroScan panel (Dade Behring, USA) and an automated system, such as the MicroScan Walk-Away® system, is used to detect substrate utilization (Dade Behring; USA).

In certain embodiments, the compositions described herein are in the form of a tablet. The tablet and a bacterial cell suspension may be combined in any type of container (e.g., the wells of a microtiter plate, a test tube, or an Eppendorf tube), and substrate utilization may be detected by an appropriate technique or device which will vary depending upon the substrate chosen.

In certain embodiments, the compositions described herein are in the form of a dry powder. The dry powder and a bacterial cell suspension may be combined in any type of container (e.g., the wells of a microtiter plate, a test tube, or an Eppendorf tube), and substrate utilization may be detected by an appropriate technique or device which will vary depending upon the substrate chosen.

4.3 Bacterial Samples

A bacterial sample isolated, obtained or derived from a biological sample from any source can be used in the methods presented herein. In one embodiment, a bacterial sample is isolated, obtained or derived from a biological sample obtained from a subject, e.g., a human subject. Examples of subjects from which such a biological sample may be obtained and utilized in accordance with the methods presented herein include, but are not limited to, asymptomatic subjects, subjects manifesting or exhibiting 1, 2, 3, 4 or more symptoms of an infection, subjects clinically diagnosed as having an infection, subjects predisposed to infections (e.g., subjects with a genetic predisposition to infections, and subjects that lead a lifestyle that predisposes them to infections or increases the likelihood of contracting an infection), subjects suspected of having an infection, subjects undergoing therapy for an infection, subjects with an infection and at least one other condition (e.g., subjects with 2, 3, 4, 5 or more conditions), subjects not undergoing therapy for an infection, and subjects that have not been diagnosed with an infection. In one embodiment, the infection is a gram negative bacterial infection. In another embodiment, the infection is a gram positive bacterial infection. Non-limiting examples of bacteria that cause bacterial infections include *E. coli, Klebsiella* (e.g., *Klebsiella pneumoniae* and *Klebsiella oxytoca*), *Staphylococcus* (e.g., *Staphylococcus aureus*), *Streptococcus* (e.g., *Streptococcus pneumoniae*), *Haemophilus influenzae, Neisseria gonorrhoeae, Pseudomonas* (e.g., *Pseudomonas aeruginosa*), *Enterococcus* and *Acinetobacter baumannii*.

In one embodiment, the subject is a mammal such as a non-primate (e.g., a cow, dog, pig, cat, dog, horse, etc.) and a primate (e.g., a human). In another embodiment, the subject is a non-human animal, such as a bird, reptile, and a non-human mammal. In another embodiment, the subject is a farm animal (e.g., a pig, horse, or cow), a pet (e.g., a guinea pig, dog, or cat) and/or a laboratory animal (e.g., a rat or mouse). In a preferred embodiment, the subject is a human.

A biological sample can be obtained from any tissue or organ in a subject, or a secretion from a subject. Representative biological samples from a subject include, without limitation, nasal swabs, throat swabs, feces, dermal swabs, blood (including blood culture), sputum, salvia, bronchio-alveolar lavage, bronchial aspirates, lung tissue, spinal fluid, synovial fluid and urine. In some embodiments, two, three or more biological samples are obtained from a subject. In specific embodiments, two or more biological samples are obtained from two or more tissues, organs and/or secretions from a subject. In addition to obtaining a biological sample from a subject, a biological sample may be obtained from food, a beverage, a phone, a counter, etc. Techniques for collecting biological samples are known to those of skill in the art.

In some embodiments, a biological sample is stored before use. For example, a biological sample from a subject can be stored at 4° C., −30° C. or −70° C. Techniques for storing biological samples are known to one of skill in the art.

In some embodiments, after a biological sample is obtained, the biological sample can be processed so that a pure bacterial sample is obtained or the biological sample can be stored before processing using techniques known to one of skill in the art. Any technique known to one of skill in the art may be used to obtain a pure bacterial sample. Generally, a biological sample is streaked onto a solid agar-containing medium so as to separate the bacterial population present in the biological sample into individual cells that grow as individual colonies. The media chosen as well as the growth conditions (e.g., the temperature and gases in the environment) will depend upon the bacteria being selected. For example, Trypticase™ Soy Agar with 5% sheep blood (BD, USA), incubated at 35° C. for 18 hours may be used to obtain individual bacterial colonies. In certain embodiments, a pure bacterial sample is used within 24 hours as a bacterial sample. In some embodiments, a pure bacterial sample is stored before use (e.g., at 4° C. or −70° C.). Techniques for storing bacterial samples are known to one of skill in the art. In some embodiments, an aliquot or inoculum of the pure bacterial sample is used as a bacterial sample. In other embodiments, an aliquot or inoculum of the pure bacterial sample is lysed and the bacterial cell extract produced is used as a bacterial sample. In some embodiments, the bacterial cell extract is stored before use.

In other embodiments, after obtaining a biological sample, the biological sample can be used to inoculate media and the inoculated media is incubated for a certain period of time to allow any bacteria present in the sample to proliferate. The media chosen as well as the growth conditions (e.g., temperature will depend upon the bacteria being collected). For example, Trypticase™ Soy Agar with 5% sheep blood (BD, USA), incubated at 35° C. for 18 hours may be used. In some embodiments, the bacterial culture is stored before use (e.g., at 4° C. or −70° C.). Techniques for storing bacterial cultures are known to one of skill in the art. In some embodiments, an aliquot or inoculum of the bacteria in the culture is used as a bacterial sample. In other embodiments, an aliquot or inoculum of the bacteria in the culture is lysed and the bacterial cell extract produced is used as a bacterial sample. In some embodiments, the bacterial cell extract is stored before use.

In some embodiments, a bacterial sample is stored before use. For example, a bacterial sample is stored at 4° C.

In certain embodiments, a sample of bacteria isolated, obtained or derived from a biological sample from any source is added to a buffer to make a cell suspension and an aliquot of the cell suspension is used as a bacterial sample. In some embodiments, a sample of bacteria isolated, obtained or derived from a biological sample from any source is added to sterile water to make a cell suspension and an aliquot of the cell suspension is used as a bacterial sample. In specific embodiments, a sample of bacteria isolated, obtained or derived from a biological sample from any source is added to a saline buffer or a broth (e.g., AST broth or ID broth sold as part of a kit for the BD Phoenix™ Automated Microbiology System (BD, USA)) to make a cell suspension and an aliquot of the cell suspension is used as a bacterial sample.

In certain embodiments, a pure bacterial sample is added to a buffer to make a cell suspension and an aliquot of the cell suspension is used as a bacterial sample. In some embodiments, a pure bacterial sample is added to sterile water to make a cell suspension and an aliquot of the cell suspension is used as a bacterial sample. In specific embodiments, a pure bacterial sample is added to a saline buffer or a broth (e.g., AST broth or ID broth sold as part of a kit for BD Phoenix™ Automated Microbiology System (BD, USA)) to make a cell suspension and an aliquot of the cell suspension is used as a bacterial sample. In a particular embodiment, the pure bacterial sample is added to the buffer, sterile water or broth within 24 hours or less of the generation of the pure bacterial sample.

In specific embodiments, a sample of bacteria isolated, obtained or derived from a biological sample from any source is lysed and an aliquot of the bacterial cell extract produced is used as a bacterial sample. Techniques for lysing bacteria are known to one of skill in the art. Non-limiting examples of techniques for lysing bacteria include the mechanical disruption techniques, freeze/thawing techniques, and lysis buffer techniques. For example, bacteria may be lysed utilizing mechanical force such as, e.g., a blender or grinder. When a sample volume is small, liquid homogenization or sonication may be used to lyse bacteria. Lysis buffer comprising one or more detergents, such as mild non-denaturing detergents (e.g., Triton® X-100 or CHAPS), may also be used to lyse bacteria. Lysis buffer comprising one or more enzymes (e.g., lysozyme, labiase, lysostaphin, achromopeptidase, or mutanolysin) or other agents that promote bacterial cell lysis may be used to lyse bacteria. In a specific embodiment, a lysis buffer comprising lysozyme and a metal chelator (e.g., EDTA or EGTA) may be used to lyse bacteria. In another embodiment, a lysis buffer comprising lysozyme and an agent that promotes the stabilization of the lysis reagent may be used to lyse bacteria. In another embodiment, a lysis buffer comprising lysozyme, an agent that promotes the stabilization of the lysis reagent and a metal chelator (e.g., EDTA or EGTA) may be used to lyse bacteria. In some embodiments, the bacterial cell extract is stored before use.

4.4 Characterization of Bacteria

In addition to or in conjunction with the beta-lactamase assays presented herein, a bacterial sample can be characterized using techniques known to one of skill in the art. For example, a bacterial sample may be observed for the morphology of the bacteria and/or different staining reactions may be performed. The morphological characteristics and staining reactions can aid in the identification of the bacteria. In a specific embodiment, a gram stain is performed using techniques known to one of skill in the art. In certain embodiments, the gram stain is performed before the beta-lactamase assays presented herein. In another embodiment, an assay to identify the species of bacteria is performed using techniques known to one of skill in the art. In a specific embodiment, an ID run on an automated antibiotic susceptibility instrument, such as the BD Phoenix ID/AST System, is performed to identify the species of bacteria.

4.5 Selection of Therapy

Detection of the presence of a specific beta-lactamase utilizing the methods presented herein can provide information for the selection of an appropriate therapeutic regimen for a patient diagnosed with a bacterial infection. For example, detecting the presence of a specific beta-lactamase in a bacterial source may indicate what antibiotics should not be used to treat an infection caused by the bacteria and suggest alternative therapies, e.g., other beta lactam drugs that the bacteria is not resistant to or non-beta lactam drugs. In addition to facilitating the appropriate therapeutic regimen for a patient, the detection of the presence of a specific beta-lactamase in a bacterial source may aid in reducing the transmission of beta-lactamase to other bacteria and/or reduce the spread of beta lactam-resistant bacteria.

4.6 Kits

Presented herein are kits for detecting the presence of particular beta-lactamases. The kits presented herein may comprise one or more of the compositions described herein. In one embodiment, the kits comprise, in one or more containers: (a) a first composition comprising a detectable beta-lactamase substrate and an AmpC inhibitor; and (b) a second composition comprising a detectable beta-lactamase substrate, an AmpC inhibitor, and a serine beta-lactamase inhibitor in an amount sufficient to inhibit an ESBL and an OSBL but not a class A serine carbapenemase. In some embodiments, the kits further comprise a third composition comprising a detectable beta-lactamase substrate, an AmpC inhibitor, a serine beta-lactamase inhibitor in an amount sufficient to inhibit an ESBL and an OSBL but not a class A serine carbapenemase, and a metal chelator. In some embodiments, the kits further comprise a fourth composition comprising a detectable beta-lactamase substrate and a serine beta-lactamase inhibitor in an amount sufficient to inhibit an ESBL and an OSBL but not a class A serine carbapenemase. In some embodiments, the kits further comprise a fifth composition comprising a detectable beta-lactamase substrate and an ESBL inhibitor. In some embodiments, the kits further comprise a sixth composition comprising a detectable beta-lactamase substrate and no beta-lactamase inhibitor. In certain embodiments, each of these compositions further comprises a lysis reagent, and optionally, an agent that promotes the stabilization of the lysis reagent and/or an agent that enhances the lysis of a bacterial cell by a lysis reagent.

In another embodiment, the kits comprise, in one or more containers: (a) a first composition comprising a detectable beta-lactamase substrate and an AmpC inhibitor; (b) a second composition comprising a detectable beta-lactamase substrate, an AmpC inhibitor, and a serine beta-lactamase inhibitor in an amount sufficient to inhibit an ESBL and an OSBL but not a class A serine carbapenemase; and (c) a third composition comprising a detectable beta-lactamase substrate and a serine beta-lactamase inhibitor in an amount sufficient to inhibit an ESBL and an OSBL but not a class A serine carbapenemase. In some embodiments, the kits further comprise a fourth composition comprising a detectable beta-lactamase substrate and no beta-lactamase inhibitor. In certain embodiments, each of these compositions further comprises a lysis reagent, and optionally, an agent that promotes the stabilization of the lysis reagent and/or an agent that enhances the lysis of a bacterial cell by a lysis reagent.

In another embodiment, the kits comprise, in one or more containers: (a) a first composition comprising a detectable beta-lactamase substrate and an AmpC inhibitor; (b) a second composition comprising a detectable beta-lactamase substrate, an AmpC inhibitor, and a serine beta-lactamase inhibitor in an amount sufficient to inhibit an ESBL and an OSBL but not a class A serine carbapenemase; and (c) a third composition comprising a detectable beta-lactamase substrate and an ESBL inhibitor. In some embodiments, the kits further comprise a fourth composition comprising a detectable beta-lactamase substrate and no beta-lactamase inhibitor. In certain embodiments, each of these compositions further comprises a lysis reagent, and optionally, an agent that promotes the stabilization of the lysis reagent and/or an agent that enhances the lysis of a bacterial cell by a lysis reagent.

In another embodiment, the kits comprise, in one or more containers: (a) a first composition comprising a detectable beta-lactamase substrate and an AmpC inhibitor; (b) a second composition comprising a detectable beta-lactamase substrate, an AmpC inhibitor, and a serine beta-lactamase inhibitor in an amount sufficient to inhibit an ESBL and an OSBL but not a class A serine carbapenemase; and (c) a third composition comprising a detectable beta-lactamase substrate, an AmpC inhibitor, a serine beta-lactamase inhibitor in an amount sufficient to inhibit an ESBL and an OSBL but not a class A serine carbapenemase and a metal chelator. In some embodiments, the kits further comprise a fourth composition comprising a detectable beta-lactamase substrate and no beta-lactamase inhibitor. In certain embodiments, each of these compositions further comprises a lysis reagent, and optionally, an agent that promotes the stabilization of the lysis reagent and/or an agent that enhances the lysis of a bacterial cell by a lysis reagent.

In another embodiment, the kits comprise, in one or more containers: (a) a first composition comprising a detectable beta-lactamase substrate and an AmpC inhibitor; (b) a second composition comprising a detectable beta-lactamase substrate, an AmpC inhibitor, and a serine beta-lactamase inhibitor in an amount sufficient to inhibit an ESBL and an OSBL but not a class A serine carbapenemase; (c) a third composition comprising a detectable beta-lactamase substrate, an AmpC inhibitor, a serine beta-lactamase inhibitor in an amount sufficient to inhibit an ESBL and an OSBL but not a class A serine carbapenemase and a metal chelator; and (d) a fourth composition comprising a detectable beta-lactamase substrate and a serine beta-lactamase inhibitor in an amount sufficient to inhibit an ESBL and an OSBL but not a class A serine carbapenemase. In some embodiments, the kits further comprise a fifth composition comprising a detectable beta-lactamase substrate and no beta-lactamase inhibitor. In certain embodiments, each of these compositions further comprises a lysis reagent, and optionally, an agent that promotes the stabilization of the lysis reagent and/or an agent that enhances the lysis of a bacterial cell by a lysis reagent.

In another embodiment, the kits comprise, in one or more containers: (a) a first composition comprising a detectable beta-lactamase substrate and an AmpC inhibitor; (b) a second composition comprising a detectable beta-lactamase substrate, an AmpC inhibitor, and a serine beta-lactamase inhibitor in an amount sufficient to inhibit an ESBL and an OSBL but not a class A serine carbapenemase; (c) a third composition comprising a detectable beta-lactamase substrate, an AmpC inhibitor, a serine beta-lactamase inhibitor in an amount sufficient to inhibit an ESBL and an OSBL but not a class A serine carbapenemase and a metal chelator; (d) a fourth composition comprising a detectable beta-lactamase substrate and a serine beta-lactamase inhibitor in an amount sufficient to inhibit an ESBL and an OSBL but not a class A serine carbapenemase; and (e) a fifth composition comprising a detectable beta-lactamase substrate and an ESBL inhibitor. In some embodiments, the kits further comprise a sixth composition comprising a detectable beta-lactamase substrate and no beta-lactamase inhibitor. In certain embodiments, each of these compositions further comprises a lysis reagent, and optionally, an agent that promotes the stabilization of the lysis reagent and/or an agent that enhances the lysis of a bacterial cell by a lysis reagent.

In another embodiment, the kits comprise, in one or more containers: (a) a first composition comprising a detectable beta-lactamase substrate; (b) a second composition comprising a detectable beta-lactamase substrate and a metal chelator. In certain embodiments, each of these compositions further comprises a lysis reagent, and optionally, an agent that promotes the stabilization of the lysis reagent and/or an agent that enhances the lysis of a bacterial cell by a lysis reagent.

The compositions included in the kits presented herein can contain any beta-lactamase substrate that is readily detectable. Non-limiting examples of detectable beta-lactamase substrates include, but are not limited, chromogenic substrates, fluorogenic substrates, and antibiotics. Chromogenic beta-lactamase substrates include nitrocefin (3-[2,4-dinitrostyryl]-7-(2-thienylacetamido]3-cephem-4-carboxylic acid (Calbiochem, San Diego, Calif.), PADAC® (Pyridinium-2-azo-p-dimethylaniline chromophore (Calbiochem, San Diego, Calif.)), CENTA™ (EMD Chemicals, Inc., San Diego, Calif.), HMRZ-86 ((7R)-7[2-aminothiazol-4-yl]-(z)-2-(1-carboxy-1-methylethoxyimino)acetamido)-3-(2,4-dinitrostyryl)-3-cephem-4-carboxylic acid trifluoroacetate, E-isomer (Kanto Chemical Co., Inc, Tokyo, Japan)), and cefesone. Fluorogenic substrates include Fluorcillin Green 495/525 and Fluorocillin Green 345/350 LiveBlazer™—FRET B/G (Invitrogen, Carlsbad, (CA). Antibiotics include beta-lactams, penicillin, amoxicillin, etc.

In one embodiment, each of the compositions included in a kit presented herein contains the same detectable beta-lactamase substrate. In another embodiment, each of the compositions included in a kit presented herein contain the same or a similar (generally within about 10% of each other) concentration of the same detectable beta-lactamase substrate. In some embodiments, the kits presented herein comprise concentrated solutions, e.g., 2×, 5× or 10× solutions of a detectable beta-lactamase substrate, that can be diluted and added to a composition. In some embodiments, the kits presented herein comprise a detectable beta-lactamase substrate as a frozen reagent. In other embodiments, the kits presented herein comprise a detectable beta-lactamase substrate as a dried reagent.

In a specific embodiment, the detectable beta-lactamase substrate included in the compositions of the kits presented herein is a chromogenic substrate. In a more specific embodiment, the detectable beta-lactamase substrate included in the compositions of the kits presented herein is nitrocefin. In a particular embodiment, nitrocefin is present in a composition included in the kits presented herein at a concentration of about 1 μM to about 1 mM, about 1 μM to about 750 μM, about 1 μM to about 500 or about 1 μM to about 250 μM. In another embodiment, nitrocefin is present in a composition described herein at a concentration of about 20 to about 200 μM.

In another embodiment, the detectable beta-lactamase substrate included in the kits presented herein is CENTA™. In a particular embodiment, a composition included in the kits presented herein comprises CENTA™ at a concentration of about 1 µM to about 1 mM, about 1 µM to about 750 µM, about 1 µM to about 500 µM, or about 1 µM to about 250 µM. In another embodiment, CENTA™ is present in a composition described herein at a concentration of about 20 µM to about 200 µM.

In another embodiment, the detectable beta-lactamase substrate included in the kits presented herein is HMRZ-86. In a particular embodiment, a composition included in the kits presented herein comprises HMRZ-86 at a concentration of about 1 µM to about 1 mM, about 1 µM to about 750 µM, about 1 µM to about 500 µM, or about 1 µM to about 250 µM. In another embodiment, HMRZ-86 is present in a composition described herein at a concentration of about 20 µM to about 200 µM.

In one embodiment, one or more of the compositions included in a kit presented herein contains one or more inhibitors. In another embodiment, for each of the compositions in a kit presented herein that comprises one or more of the same inhibitors the concentrations of those inhibitors is the same or similar (generally within about 10% of each other). In some embodiments, the kits presented herein comprise concentrated solutions, e.g., 2×, 5× or 10× solutions, of an inhibitor that can be diluted and added to a composition. In some embodiments, the kits presented herein comprise an inhibitor as a frozen reagent. In other embodiments, the kits presented herein comprise an inhibitor as a dried reagent. In some embodiments, the kits presented herein comprise a composition comprising a detectable beta-lactamase substrate and one or more inhibitors in a form in which the bacteria can be contacted with the composition in accordance with the methods presented herein. In some embodiments, the kits presented herein comprise all of the components that can be used to make the various compositions of the kits.

In one embodiment, a composition included in the kits presented herein comprise an AmpC inhibitor at a concentration of about 1 µM to about 100 mM, about 1 µM to about 75 mM, about 1 µM to about 50 mM, about 1 µM to about 25 mM, about 1 µM to about 10 mM, or about 1 µM to about 5 mM of an AmpC inhibitor. In another embodiment, a composition included in the kits presented herein comprise an AmpC inhibitor at a concentration of about 100 µM to about 4 mM, about 200 µM to about 4 mM, 500 µM to about 4 mM, about 750 µM to about 4 mM, or about 1 mM to about 4 mM of an AmpC inhibitor. In another embodiment, a composition included in the kits presented herein comprise an AmpC inhibitor at a concentration of about 500 µM to about 3 mM, about 1 mM to about 3 mM, about 1.5 mM to about 3 mM, or about 2 mM to about 3 mM of an AmpC inhibitor.

In a specific embodiment, a composition included in the kits presented herein comprise cloxacillin, a salt form of cloxacillin, syn2190 (NAEJA Pharmaceutical, Inc., Edmonton, Alberta, Canada), or boronic acid or its derivatives thereof (Focus Synthesis LLC, San Diego, Calif.) as the AmpC inhibitor. In a particular embodiment, a composition included in the kits presented herein comprise cloxacillin or a salt form thereof as the AmpC inhibitor. In a specific embodiment, a composition included in the kits presented herein comprises about 20 µM to about 5 mM of cloxacillin or a salt form thereof. In another embodiment, a composition included in the kits presented herein comprises about 20 µM to about 4 mM, about 20 µM to about 3 mM, about 20 µM to about 2 mM, about 20 µM to about 1 mM, about 20 µM to about 750 µM, about 20 µM to about 500 µM, about 20 µM to about 250 µM, or about 20 µM to about 75 µM of cloxacillin or a salt form thereof.

In another embodiment, a composition included in the kits presented herein comprise about 500 µM to about 5 mM, about 500 µM to about 4 mM, about 500 µM to about 3 mM, about 500 µM to about 2 mM, or about 500 µM to about 1 mM of cloxacillin or a salt form thereof. In another embodiment, a composition comprises about 1 mM to about 5 mM, about 2 mM to about 5 mM, about 1 mM to about 4 mM, about 2 mM to about 4 mM, about 1 mM to about 3 mM, or about 1 mM to about 2 mM of cloxacillin or a salt form thereof.

In one embodiment, a composition included in the kits presented herein comprises a serine beta-lactamase inhibitor. In a particular embodiment, a composition included in the kits presented herein comprises tazobactum or a salt form thereof. In a specific embodiment, a composition included in the kits presented herein comprises about 100 µM to about 1 mM, about 100 µM to about 750 µM, about 100 µM to about 500 µM, or about 100 µM to about 250 µM of tazobactum or a salt form thereof. In another embodiment, a composition included in the kits presented herein comprises sulbactam or a salt form thereof. In a specific embodiment, a composition included in the kits presented herein comprises about 100 µM to about 5 mM, about 100 µM to about 4 mM, about 100 µM to about 3 mM, about 100 µM to about 2 mM, or about 100 µM to about 1 mM of sulbactam or a salt form thereof. In another embodiment, a composition included in the kits presented herein comprises about 100 µM to about 750 about 100 µM to about 500 µM, 100 µM to about 250 µM, about 100 µM to about 200 mM, or about 100 µM to about 150 µM of sulbactam or a salt form thereof.

In one embodiment, a composition included in the kits presented herein, comprises clavulanic acid or a salt form thereof. In a specific embodiment, a composition included in the kits presented herein comprises about 10 µM to about 100 mM, about 10 µM to about 75 mM, about 10 µM to about 50 mM, about 10 µM to about 25 mM, about 10 µM to about 10 mM, or about 10 µM to about 5 mM of clavulanic acid or a salt form thereof. In another embodiment, a composition included in the kits presented herein comprises about 10 µM to about 2 mM, about 25 µM to about 2 mM, 50 µM to about 2 mM, about 75 µM to about 2 mM, or about 100 µM to about 2 mM of clavulanic acid or a salt form thereof. In another embodiment, a composition included in the kits presented herein comprises about 200 µM to about 2 mM, about 250 to about 2 mM, about 300 µM to about 2 mM, about 400 µM to about 2 mM, or about 500 µM to about 2 mM of clavulanic acid or a salt form thereof. In a particular embodiment, a composition included in the kits presented herein comprises about 500 µM to about 1.5 mM of clavulanic acid or a salt form thereof.

In a specific embodiment, a composition included in the kits presented herein comprise a zinc-specific metal chelator, such as TPEN. In alternative embodiment, a composition included in the kits presented herein comprise a metal chelator that is able to bind to zinc but is not zinc-specific, such as DMPS, EDTA. 1,10-phenanthroline, DPC or DEDTC. In a preferred embodiment, a composition included in the kits presented herein comprise a metal chelator that is membrane permeable. In some embodiments, a composition comprises EDTA, DMPS, 1,10-phenanthroline, DEDTC, TPEN or DPC at a concentration of about 0.5 mM to about 200 mM, about 1 mM to about 100 mM, or about 1 mM to about 50 mM.

In a specific embodiment, a composition included in the kits presented herein comprises DPC at a concentration of about 0.5 mM to about 10 mM, about 0.5 mM to about 7 mM, about 0.5 mM to about 5 mM, about 0.5 mM to about 2 mM or about 0.5 mM to about 1 mM. In another embodiment, a composition included in the kits presented herein DEDTC at a concentration of about 1 mM to about 20 mM, about 1 mM to about 15 mM, about 1 mM to about 10 mM, about 1 mM to about 7 mM, about 1 mM to about 5 mM or about 1 mM to about 2 mM.

In one embodiment, a composition included in the kits presented herein comprises an ESBL inhibitor. In one embodiment, a composition included in the kits presented herein comprises ceftazidime or a salt form thereof. In a specific embodiment, a composition included in the kits presented herein comprises ceftazidime at a concentration of about 1 mM to about 20 mM, about 1 mM to about 15 mM, about 1 mM to about 10 mM, about 1 mM to about 7 mM, about 1 mM to about 5 mM, or about 1 mM to about 2 mM. In another embodiment, a composition included in the kits presented herein comprises cefotaxime or a salt form thereof. In another embodiment, a composition included in the kits presented herein comprises cefotaxime at a concentration of about 1 mM to about 20 mM, to about 15 mM, about 1 mM to about 10 mM, about 1 mM to about 7 mM, about 1 mM to about 5 mM, or about 1 mM to about 2 mM. In another embodiment, a composition included in the kits presented herein comprises a combination of ceftazidime and cefotaxime. In another embodiment, a composition included in the kits presented herein comprises a combination of ceftazidime and cefotaxime or salt forms thereof at a concentration of about 1 mM to about 20 mM, about 1 mM to about 15 mM, about 1 mM to about 10 mM, about 1 mM to about 7 mM, about 1 mM to about 5 mM, or about 1 mM to about 2 mM.

In some embodiments, the kits described herein contain a composition comprising a lysis reagent. In certain embodiments, in addition to a beta-lactamase substrate and in some embodiments, one or more beta-lactamase inhibitors, the compositions in the kits described herein comprise a lysis reagent. In a specific embodiment, the lysis reagent lyses the bacterial cells but does not interfere with either the hydrolysis of the beta-lactamase substrate or the activity of one or more beta-lactamase inhibitors, or both. In one embodiment, the lysis reagent is a detergent, such as mild non-denaturing detergent (e.g., Triton® X-100 or CHAPS). In another embodiment, the lysis reagent is an enzyme or other agent that promotes the lysis of a bactierial cell. Non-limiting examples of such an enzyme include lysozyme, labiase, lysostaphin, achromopeptidase, or mutanolysin. In a particular embodiment, the kits described herein contain a composition comprising about 0.1 mg/ml to about 10 mg/ml, about 0.5 mg/ml to about 10 mg/ml, about 1 mg/ml to about 10 mg/ml, about 2 mg/ml to about 10 mg/ml, about 3 mg/ml to about 10 mg/ml, about 4 mg/ml to about 10 mg/ml or about 5 mg/ml to about 10 mg/ml of a lysis reagent (e.g., lysozyme). In another embodiment, the compositions used in accordance with the methods described herein comprise about 0.1 mg/ml to about 8 mg/ml, about 1 mg/ml to about 6 mg/ml, about 1 mg/ml to about 5 mg/ml, about 1 mg/ml to about 5 mg/ml, about 2 mg/ml to 4 mg/ml, or about 3 mg/ml of a lysis reagent (e.g., lysozyme). In a specific embodiment, the kits described herein contain a composition comprising lysozyme.

In some embodiments, the kits described herein contain a composition comprising a lysis reagent and an agent that promotes the stabilization of the lysis reagent. In certain embodiments, in addition to a beta-lactamase subtrate and in some embodiments, one or more beta-lactamase inhibitors, the compositions in the kits described herein comprise a lysis reagent and an agent that promotes the stabilization of the lysis reagent. In one embodiment, the agent that promotes the stabilization of the lysis reagent is thermal stable. In a particular embodiment, the kits described herein contain a composition comprising about 0.1% to about 10%, about 1% to about 10%, about 2% to about 10%, about 4% to about 10%, about 1% to about 8%, about 2% to about 8%, about 2% to about 6%, or about 2% to about 4% of an agent that promotes the stabilization of the lysis reagent.

In one embodiment, the kits described herein contain a composition comprising a lysis reagent and a carbohydrate, e.g., a monosaccharide, a disaccharide, a polysaccharide, an oligosaccharide, or a polyol. Specific examples of carbohydrates include, but are not limited to, mannitol, ribose, glucose, fructose, mannose, sucrose, lactose, glycerol, Xanthan gum, trehalose and glycols (e.g., propylene glycol). In a specific embodiment, the kits described herein contain a composition comprising lysozyme and trehalose.

In some embodiments, the kits described herein contain a composition comprising a lysis reagent, an agent that promotes the stabilization of the lysis reagent, and an additional agent, e.g., an agent that enhances the lysis of a bacterial cell by a lysis reagent (e.g., a metal chelator). In one embodiment, the kits described herein contain a composition comprising about 0.1 mM to about 5 mM, about 1 mM to about 4 mM, about 1 mM to about 3 mM, about 2 mM to about 3 mM, or about 0.1 to about 2 mM of an agent that enhances the lysis of a bacterial cell by a lysis reagent.

In a specific embodiment, the kits described herein contain a composition comprising a lysis reagent, an agent that promotes the stabilization of the lysis reagent, and EDTA or EGTA. In particular embodiments, either EDTA or EGTA, or both are not utilized if a metallo-beta-lactamase is or may be detected. In a specific embodiment, the kits described herein contain a composition comprising a lysozyme, trehalose and EDTA.

In a specific embodiment, for each of the compositions in a kit presented herein that comprises one or more of the same lysis reagents (and optionally, an agent that promotes the stabilization of the lysis reagent and/or an agent that promotes degradation of a bacterial cell wall) the concentrations of those reagents (and agents) is the same or similar (generally within about 10% of each other). In some embodiments, the kits presented herein comprise concentrated solutions, e.g., 2×, 5× or 10× solutions, of lysis reagents that can be diluted and added to a composition. In some embodiments, the kits presented herein comprise concentrated solutions, e.g., 2×, 5× or 10× solutions, of agents that stabilize the lysis reagent which can be diluted and added to a composition. In some embodiments, the kits presented herein comprise concentrated solutions, e.g., 2×, 5× or 10× solutions, of agents that promote the degradation of a bacterial cell wall which can be diluted and added to a composition. In some embodiments, the kits presented herein comprise one, two or all of the following as a frozen reagent or agent: a lysis reagent, an agent that promotes the stabilization of the lysis reagent, and an agent promotes degradation of a bacterial cell wall as a frozen reagent or agent. In other embodiments, the kits presented herein comprise one, two or all of the following as a dried reagent or agent: a lysis reagent, an agent that promotes the stabilization of the lysis reagent, and an agent enhances the lysis of a bacterial cell by a lysis reagent.

In specific embodiments, the kits presented herein comprise a composition in a form in which the bacteria can be contacted with the composition in accordance with the methods presented herein. In one embodiment, the composition comprises a detectable beta-lactamase substrate, a lysis reagent and optionally, one or more inhibitors, an agent that promotes the stabilization of the lysis reagent and/or an agent that enhances the lysis of a bacterial cell by a lysis reagent. In another embodiment, the composition comprises a detectable beta-lactamase substrate, a lysis reagent and one or more inhibitors, and optionally, either or both, an agent that promotes the stabilization of the lysis reagent and/or an agent that enhances the lysis of a bacterial cell by a lysis reagent. In another embodiment, the composition comprises a detectable beta-lactamase substrate, a lysis reagent and one or more inhibitors, an agent that promotes the stabilization of the lysis reagent and optionally an agent that enhances the lysis of a bacterial cell by a lysis reagent.

In addition to a detectable beta-lactamase substrate and one or more beta-lactamase inhibitors, the compositions included in the kits presented herein may include a buffer. Any buffer that aids in maintaining the pH of the composition and does not interfere with the hydrolysis of the beta-lactamase substrate may be used. In a specific embodiment, the buffer does not interfere with either the hydrolysis of the beta-lactamase substrate or the activity of one or more beta-lactamase inhibitors, or both. Non-limiting examples of buffers include phosphate, MES buffer, acetate buffer, Tris buffer, ADA buffer, MOPS buffer, and HEPES buffer. In one embodiment, each of the compositions included in a kit presented herein contains the same buffer. In another embodiment, each of the compositions included in a kit presented herein contains the same or a similar (i.e., within about 10% of each other) concentration of the same buffer. In a specific embodiment, a composition comprises 0.05 to 1 ml of phosphate or MES buffer. In some embodiments, the kits presented herein comprise concentrated solutions, e.g., 2×, 5× or 10× solutions, of a buffer which may be diluted and added to a composition.

In some embodiments, the kits presented herein may include a saline buffer or a broth. Any broth that does not interfere with either the hydrolysis of the beta-lactamase substrate or the activity of one or more beta-lactamase inhibitors, or both may be used. In a specific embodiment, the AST broth and/or ID broth utilized with a BD Phoenix™ Panel (BD, USA) is included in a kit presented herein. In some embodiments, the kits presented herein comprise concentrated solutions, e.g., 2×, 5× or 10× solutions, of a broth which may be diluted before use.

In a specific embodiment, each composition included in a kit presented herein has the same or a similar (i.e., within about 10% or about 5% of each other) pH. In one embodiment, a composition has a pH of about pH 5 to pH 8, preferably about pH 5.5 to about pH 7.5, and more preferably about pH 6 to about pH 7.

In some embodiments, a kit presented herein comprises a container comprising a detectable beta-lactamase substrate, one or more other containers comprising one or more inhibitors, and, optionally, instructions. In certain embodiments, a kit presented herein comprises a first container comprising a detectable beta-lactamase substrate, a second container comprising a composition comprising a lysis reagent, one or more other containers comprising one or more inhibitors, and, optionally, instructions. In other embodiments, a kit presented herein comprises a first container comprising a detectable beta-lactamase substrate, a second container comprising a composition comprising a lysis reagent and an agent that promotes the stabilization of the lysis reagent, one or more other containers comprising one or more inhibitors, and, optionally, instructions. In other embodiments, a kit presented herein comprises a first container comprising a detectable beta-lactamase substrate, a second container comprising a composition comprising a lysis reagent, an agent that promotes the stabilization of the lysis reagent, and an agent that enhances the lysis of a bacterial cell by a lysis reagent, one or more other containers comprising one or more inhibitors, and, optionally, instructions. In other embodiments, a kit presented herein comprises a first container comprising a detectable beta-lactamase substrate, a second container comprising a composition comprising a lysis reagent, a third container comprising an agent that promotes the stabilization of the lysis reagent, one or more other containers comprising one or more inhibitors, and, optionally, instructions. In other embodiments, a kit presented herein comprises a first container comprising a detectable beta-lactamase substrate, a second container comprising a composition comprising a lysis reagent, a third container comprising an agent that promotes the stabilization of the lysis reagent, a fourth container comprising an agent that enhances the lysis of a bacterial cell by a lysis reagent, one or more other containers comprising one or more inhibitors, and, optionally, instructions.

In some embodiments, a kit presented herein comprises a container comprising a composition and, optionally, instructions, wherein the composition comprises a detectable beta-lactamase substrate and one or more inhibitors. In certain embodiments, a kit presented herein comprises a container comprising a composition and, optionally, instructions, wherein the composition comprises a detectable beta-lactamase substrate, one or more inhibitors, and a lysis reagent. In other embodiments, a kit presented herein comprises a container comprising a composition and, optionally, instructions, wherein the composition comprises a detectable beta-lactamase substrate, one or more inhibitors and a lysis reagent and an agent that promotes the stabilization of the lysis reagent. In other embodiments, a kit presented herein comprises a container comprising a composition and, optionally, instructions, wherein the composition comprises a detectable beta-lactamase substrate, one or more inhibitors, a lysis reagent, an agent that promotes the stabilization of the lysis reagent, and an agent that enhances the lysis of a bacterial cell by a lysis reagent.

The instructions that can be included in the kit may instruct the kit user how to make up specific compositions, such as those described herein, so that specific beta-lactamases can be detected. For example, the instructions may inform the kit user to make up and add a certain concentration of a buffer to compositions as well as the concentration of a detectable beta-lactamase substrate and one or more inhibitors to add to a composition. In some embodiments, the detectable beta-lactamase substrate included in the kit needs to be diluted before being used. In some embodiments, one or more of the inhibitors needs to be diluted before being used. In some embodiments, the compositions included in the kits presented herein are in a form ready to be contacted with a bacterial sample.

The compositions included in the kits can be any form amenable to detection of substrate utilization following contact of a composition with a bacterial sample. For example, the compositions included in the kits may be in the form of a liquid composition, an agar plate, a paper disk, a paper strip, a tablet or dry form in wells. In a specific embodiment, the compositions are liquid compositions included in the kits with each liquid composition comprising a detectable beta-lactamase substrate and one or more different beta-lactamase inhibitors. In another embodiment, the compositions included in the kits are frozen.

In some embodiments, the compositions included in the kits described herein are dried and are present on or in a solid support, such as the well of a plate, panel, cassette or tray, a paper strip, paper disk, or a tube. In certain embodiments, the compositions are dried onto or in the solid support using heat, e.g., at temperatures of, e.g., 50° C. to 100° C., 50° C. to 85° C. 50° C. to 75° C., 60° C. to 75° C. or 60° C. to 70° C. In one embodiment, the compositions are dried onto or in the solid support using heat under forced air or vacuum conditions at, e.g., temperatures of, e.g., 50° C. to 100° C., 50° C. to 85° C., 50° C. to 75° C., 60° C. to 75° C. or 60° C. to 70° C. In other embodiments, the compositions are dried onto or in the solid support using a lypholization technique. In other embodiments, the compositions are dried onto or in the solid support using a spray drying technique.

In another embodiment, the compositions included in the kits are part of one agar plate that is divided up into different sections with each section comprising a different composition. For example, the agar plate may comprise three sections with each section comprising a composition comprising a detectable beta-lactamase substrate and one or more different beta-lactamase inhibitors. In another embodiment, there is only one composition per agar plate. In other words, each agar plate only comprises one composition so that two or more agar plates comprising different compositions are utilized in the methods presented herein.

In another embodiment, the compositions included in the kits are part of a paper disk or paper strip that is divided up into different sections with each section comprising a different composition. For example, the paper disk or paper strip may comprise three sections with each section comprising a composition comprising a detectable beta-lactamase substrate and one or more different beta-lactamase inhibitors. In another embodiment, there is only one composition per paper disk or paper strip. In other words, each paper disk or paper strip only comprises one composition so that two or more paper disks or paper strips comprising different compositions are utilized in the methods presented herein. In a specific embodiment, the paper disk or paper strip is filter paper. Non-limiting examples of the types of filter paper that may be used include Whatman paper (VWR, Pennsylvania, U.S.A.). In another embodiment, the compositions included in the kits are in dry wells that are hydrated before use. In a specific embodiment, the compositions included in the kits are in a form similar to BBL™ Dryslider™ Nitrocefin (BD Diagnostic Systems, USA). In some embodiments, substrate utilization is detected by visual inspection when the compositions included in the kits are in the form of a paper disk, a paper strip or a dry well.

In certain embodiments, the compositions included in the kits are dried and are present in the wells of a panel, tray, cassette or plate (e.g., a microtiter plate). In specific embodiments, the compositions included in the kits are dried and are present in the wells of a tray, cassette or panel, such as the Phoenix™ Panel (BD, USA), the Vitek® card (bioMerieux, USA), a panel for the BBL™ Crystal™ Identification System (BD, USA), a panel for the Remel RapID™ System (Remel, USA), or a MicroScan panel (Dade Behring, USA). See, e.g., U.S. Pat. No. 5,922,593 and Des. 421,498 (each of which are incorporated herein by reference) for a description of panels with wells that the compositions included in the kits may be dried on or in using, e.g., heat. In some embodiments, the compositions included in the kits are dried and are present in a tube for the API biochemical test (bioMerieux, USA).

In a particular embodiment, the compositions included in the kits are dried and are present in the wells of a Phoenix™ Panel (BD, USA) and an automated system, such as the BD Phoenix™ Automated Microbiology System (BD, USA), is used to detect substrate utilization. See, e.g., U.S. Pat. Nos. 5,922,593, 6,372,485, 6,096,272, and 7,115,384 (each of which are incorporated herein by reference) for a description of an automated system for detection of substrate utilization. In other embodiments, the compositions included in the kits are dried and are present in the wells of a panel for the BBL™ Crystal™ Identification System (BD, USA) and an automated system, such as the BBL™ Crystal™ Identification System (BD, USA), is used to detect substrate utilization. In other embodiments, the compositions included in the kits are dried and are present in the wells of a Vitek® card (bioMerieux, USA) and an automated system, such as the Vitek® system (bioMerieux, USA), is used to detect substrate utilization. In other embodiments, the compositions included in the kits are dried and are present in the wells of a MicroScan panel (Dade Behring, USA) and an automated system, such as the MicroScan Walk-Away® system, is used to detect substrate utilization.

In some embodiments, the compositions included in the kits comprise inert ingredients that stabilize the detectable beta-lactamase substrate and/or inhibitors for storage. For example, compositions included in the kits may comprise sucrose to promote stabilization of the compositions for storage.

In addition to compositions, the kits presented herein may comprise instructions for using the kits to detect particular beta-lactamases. In a specific embodiment, the instructions recommend that positive and negative controls are run in parallel with test samples. In some embodiments, the kits presented herein comprise a bacterial sample that is known to not express one or more particular beta-lactamases (i.e., a negative control). In other embodiments, the kits presented herein comprise a bacterial sample that is known to express one or more particular beta-lactamases (i.e., a positive control). In yet other embodiments, the kits presented herein comprise a bacterial sample that is known to express one or more particular beta-lactamases (i.e., a positive control) and a bacterial sample that is known to not express one or more particular beta-lactamases (i.e., a negative control). In some embodiments, the bacterial control(s) is lypholized.

4.7 Systems

Presented herein are systems comprising a kit or a component(s) of the kits presented herein and a computer program product for use in conjunction with a computer system. In such systems, the computer program product can comprise a computer readable storage medium and a computer program mechanism embedded therein. The computer program mechanism may comprise instructions for evaluating the presence of particular beta-lactamases, including class A serine carbapenemases, metallo-beta-lactamases, AmpC beta-lactamases and/or ESBLs, in one or a plurality of bacterial samples. In some embodiments, the computer program comprises instructions for evaluating the presence of one, two, three or more of the following: a class A serine carbapenemase, a metallo-beta-lactamase, an AmpC beta-lactamase and/or an ESBL.

In a specific embodiment, the system used for evaluating the presence of the beta-lactamases described herein is the same or similar to the BD Phoenix™ Automated Microbiology System (BD, USA). See, e.g., U.S. Pat. Nos. 5,922,593, 6,372,485, 6,096,272, and 7,115,384 (each of which are incorporated herein by reference) for a description of such an automated system. In another embodiment, the system for evaluating the presence of the beta-lactamase described herein is the same or similar to the BBL™ Crystal™ Identification System (BD, USA). In another embodiment, the system used for evaluating the presence of the beta-lactamases described herein is the same or similar to the Vitek® automated system from bioMerieux. In another embodiment, the system used for evaluating the presence of the beta-lactamases described herein is the same or similar to the MicroScan Walk-Away® automated system from Dade Behring.

Some systems presented herein comprise a kit or one or more components of the kits presented herein, a computer having a central processing unit and a memory coupled to the central processing unit. Some systems presented herein comprise a kit or one or more components of the kits presented herein, a computer readable medium (such as a handheld fluorometer or spectrophotometer), a computer having a central processing unit and a memory coupled to the central processing unit. The memory stores instructions for evaluating the presence of particular beta-lactamases, including class A serine carbapenemases, metallo-beta-lactamases, AmpC beta-lactamases and ESBLs. In specific embodiments, the memory stores instructions for evaluating the presence of one, two, three or more of the following: a class A serine carbapenemases, metallo-beta-lactamases, AmpC beta-lactamases and ESBL. In some embodiments, the memory comprises instructions for transmitting the results of a method presented herein to a remote computer and the remote computer includes instructions for evaluating ther presence of one, two, three or more beta-lactamases.

In some embodiments, presented herein is a computer system comprising a computer readable medium comprising the results of an evaluation for the presence of a particular beta-lactamase, including class A serine carbapenemases, metallo-beta-lactamases, AmpC beta-lactamases, and/or ESBLs, as described herein. In some embodiments, a computer system presented herein comprises:

a central processing unit;

a main non-volatile storage unit, for example, a hard disk drive, for storing software and data, the storage unit controlled by storage controller;

a system memory, such as high speed random-access memory (RAM), for storing system control programs, data and application programs, comprising programs and data loaded from non-volatile storage unit, and may also include a read-only memory (ROM);

a user interface, comprising one or more input devices (e.g., a keyboard) and display or other output device;

a network interface card for connecting to any wired or wireless communication network (e.g., a wide area network such as the Internet);

an internal bus for interconnecting the aforementioned elements of the system; and a power source to power the aforementioned elements.

Operation of the computer can be controlled primarily by an operating system, which is executed by a central processing unit. The operating system can be stored in the system memory. In addition to the operating system, an implementation system may include: a file system for controlling access to the various files and data structures presented herein; a training data set for use in the construction of one or more decision rules in accordance with the methods presented herein; a data analysis algothrithm module for processing training data and constructing decision rules; one or more decision rules; a profile evaluation module for determining whether a beta-lactamase is present.

The computer may comprise software program modules and data structures. Each of the data structures can comprise any form of a data storage system, including, but not limited to, a flat ASCII or binary file, an Excel spreadsheet, a relational database (e.g., SQL), or an on-line analytical processing (OLAP) database (e.g., MDX and/or variants thereof). In some embodiments, such data structures are each in the form of one or more databases that include a hierarchical structure (e.g., a star schema). In some embodiments, such data structures are each in the form of databases that do not have explicit hierarchy (e.g., dimension tables that are not hierarchically arranged).

In some embodiments, each of the data structures stored or accessible to the computer system are single data structures. In other embodiments, such data structures in fact comprise a plurality of data structures (e.g., databases, files, archives) that may or may not all be hosted by the same computer. For example, in some embodiments, a training data set may comprise a plurality of Excel spreadsheets that are stored either on the computer and/or computers that are addressable by the computer across wide area network. In another example, a training set may comprise a database that is either stored on the computer or is distributed across one or more computers that are addressable by the computer across a wide area network.

It will be appreciated that many of the modules and data structures mentioned above can be located on one or more remote computers. For example, in some embodiments, web service-type implementations are used. In such embodiments, an evaluation module can reside on a client computer that is in communication with the computer via a network. In some embodiments, a profile evaluation module can be an interactive web page.

In some embodiments, a training data set and/or decision rules are on a single computer and in other embodiments, one or more of such data structures and modules are hosted by one or more remote computers. Any arrangement of the data structures and software modules on one or more computers is within the scope the systems presented herein so long as these data structures and software modules are addressable with respect to each other across a network or by other electronic means.

In some embodiments, a digital signal embodied on a carrier wave comprises data with respect to a method presented herein. In some embodiments, a digital signal embodied on a carrier wave comprises a determination as to whether a particular beta-lactamase is present in a bacterial source. In some embodiments, a graphical user interface is provided for determining whether a beta-lactamase is present in a bacterial source. The graphical user interface may comprise a display field for displaying a result encoded in a digital signal embodied on a carrier wave received from a remote computer.

5. EXAMPLES

The examples presented herein demonstrate the accuracy and efficiency of using a detectable beta-lactamase substrate and one or more beta-lactamase inhibitors to detect the presence of specific beta-lactamases.

5.1 Carbapenemase Detection

This example demonstrates that compositions a comprising detectable beta-lactamase substrate and one or more beta-lactamase inhibitors may be used to detect the presence of a carbapenemase in a sample.

5.1.1 Materials & Methods

Chromogenic Beta-Lactamase Assay

Representative *E. coli* bacterial strains were each streaked on a Trypticase™ Soy Agar with 5% Sheep Blood agar plate and the plate was incubated at 35° C. for 18 hours. Afterwards, a sample from each plate was added to 1 ml sterile water in a BD 2054 Falcon tube to a turbidity of about 1.6 as measured by a Microscan turbidity reader. 50 µl of a cell suspension was added to each of the following 150 µl compositions to bring the final concentration in each compositions to the following: (i) Composition 1 comprising 50 µM of nitrocefin, 2 mM of cloxacillin, and 75 mM pH 7.0 phosphate buffer; and (ii) Composition 2 comprising 50 μM of nitrocefin, 2 mM of cloxacillin, 1 mM of clavulanic acid and 75 mM pH 7.0 phosphate buffer. The color of the nitrocefin was assessed visually after 10 minutes (for *Klebsiella oxytoca* strains) or 1 hour (for *E. coli* and *Klebsiella pneumoniae*). The hydrolysis of nitrocefin by a beta-lactamase causes the color of the composition to change from yellow to red.

Imipenem MIC Assay

Imipenem MIC Assay was performed by microbroth dilution method according to the CLSI (Clinical and Laboratory Standards Institute) standard.

5.1.2 Results

The results of a chromogenic beta-lactamase assay for representative *E. coli* strains are summarized in Table 7, below. Table 8, below, compares the conclusions based on the beta-lactamase assay described herein to the results obtained by the imipenem MIC assay and the beta-lactamase profile determined previously by isoelectric focusing (IEF) and PCR testing for the same *E. coli* strains in Table 7. The conclusions based on the chromogenic beta-lactamase assay results are consistent with the conclusions based upon the imipenem MIC, IEF and PCR results for the detection of the presence of a carbapenemase.

TABLE 7

| | Utilization of nitrocefin in composition 1 | Utilization of nitrocefin in composition 2 | Presence of carbapenemase |
|---|---|---|---|
| 1 | − | − | No |
| 2 | + | + | Yes |
| 3 | + | + | Yes |
| 4 | + | − | No |
| 5 | + | − | No |
| 6 | + | + | Yes |
| 7 | + | − | No |
| 8 | − | − | No |
| 9 | − | − | No |
| 10 | + | − | No |
| 11 | + | − | No |

+ indicates that nitrocefin is utilized and changes from yellow to red
− indicates that nitrocefin is not utilized and stays yellow.

TABLE 8

| | Presence of carbapenemase based on chromogenic beta-lactamase assay | Imipenem MIC (μg/ml) | Beta-lactamase profile based on reference methods (IEF, PCR, MIC assays) |
|---|---|---|---|
| 1 | no | <=2 | C-chromo |
| 2 | yes | 8 | Carb, C-plasmid |
| 3 | yes | =16 | Carb (KPC) |
| 4 | no | <=2 | ESBL, C-chromo |
| 5 | no | <=2 | IRT, C-chromo |
| 6 | yes | 8 | OSBL, Carb |
| 7 | no | <=2 | OSBL, C-plasmid |
| 8 | no | <=0.25 | WT |
| 9 | no | <=2 | WT |
| 10 | no | <=2 | OSBL, C-chromo |
| 11 | no | <=2 | ESBL, C |

WT means wild-type or without beta-lactamase.
C-chromo means chromosomal AmpC beta-lactamase.
C-plasmid means plasmid-borne AmpC beta-lactamase.
Carb means carbapenemase.
Carb(KPC) means carbapenemase encoded by KPCs (KPC-1, KPC-2, KPC-3 or KPC-4).
IRT means inhibitor-resistant TEM beta-lactamase.
ESBL means extended-spectrum beta-lactamase.
OSBL means original-spectrum beta-lactamase.
C means either C-chromo or C-plasmid beta-lactamase.

The results of a chromogenic beta-lactamase assay for representative *Klebsiella pneumoniae* strains are summarized in Table 9, below. Table 10, below, compares the conclusions based on the beta-lactamase assay described herein to the results obtained by the imipenem MIC assay and the beta-lactamase profile determined previously by isoelectric focusing (IEF) and PCR testing for the same *Klebsiella pneumoniae* strains in Table 9. The conclusions based on the chromogenic beta-lactamase assay results are consistent with the conclusions based upon the imipenem MIC, IEF and PCR results for the detection of the presence of a carbapenemase.

TABLE 9

| | Utilization of nitrocefin in composition 1 | Utilization of nitrocefin in composition 2 | Presence of carbapenemase |
|---|---|---|---|
| 1 | − | − | no |
| 2 | + | + | yes |
| 3 | − | − | no |
| 4 | + | + | yes |
| 5 | + | − | no |
| 6 | + | − | no |
| 7 | − | − | no |
| 8 | + | − | no |
| 9 | + | + | yes |
| 10 | + | − | no |
| 11 | + | reduced + | no |
| 12 | + | + | yes |
| 13 | + | + | yes |
| 14 | + | − | no |
| 15 | + | + | yes |
| 16 | + | + | yes |

+ indicates that nitrocefin is utilized and change from yellow to red.
− indicates that nitrocefin is not utilized and stays yellow.

TABLE 10

| | Presence of carbapenemase based on chromogenic beta-lactamase assay | Imipenem MIC (μg/ml) | Beta-lactamase Profile |
|---|---|---|---|
| 1 | no | <=2 | C-plasmid |
| 2 | yes | =4 | ESBL, MBL |
| 3 | no | <=2 | ESBL, C |
| 4 | yes | =8 | ESBL, Carb (KPC) |
| 5 | no | <=2 | ESBL, C-plasmid |
| 6 | no | <=2 | ESBL, C-plamid |
| 7 | no | <=2 | WT |
| 8 | no | <=2 | OSBL, C-plasmid |
| 9 | yes | >16 | OSBL, carb |
| 10 | no | <=2 | WT |
| 11 | no | <=2 | OSBL, C-plasmid |
| 12 | yes | >16 | MBL |
| 13 | yes | 4 | ESBL, MBL |
| 14 | no | <=2 | ESBL, C-plasmid |
| 15 | yes | =8 | Carb(KPC) |
| 16 | yes | =8 | ESBL, Carb(KPC) |

WT means wild-type or without beta-lactamase.
C-plasmid means plasmid-borne AmpC beta-lactamase.
C means an AmpC beta-lactamase either plasmid-borne or chromosomal.
Carb(KPC) means serine carbapenemase encoded by KPC.
ESBL means extended-spectrum beta-lactamase.
OSBL means original spectrum beta-lactamase.
MBL means metallo-beta-lactamase.

The results of a chromogenic beta-lactamase assay for representative *Klebsiella oxytoca* strains are summarized in Table 11, below. Table 12, below, compares the conclusions based on the beta-lactamase assay described herein to the results obtained by the imipenem MIC assay and the beta-lactamase profile determined previously by isoelectric focusing (IEF) and PCR testing for the same *Klebsiella oxytoca* strains in Table 11. The conclusions based on the chromogenic beta-lactamase assay results are consistent with the conclusions based upon the Imipenem MIC, IEF and PCR results for the detection of the presence of a carbapenemase.

TABLE 11

|   | Utilization of nitrocefin in composition 1 | Utilization of nitrocefin in composition 2 | Presence of carbapenemase based on Chromogenic Assay |
|---|---|---|---|
| 1 | + | − | No |
| 2 | + | − | no |
| 3 | + | + | yes |
| 4 | − | − | no |

+ indicates that nitrocefin is utilized and change from yellow to red.
− indicates that nitrocefin is not utilized and stays yellow.

TABLE 12

|   | Presence of carbapenemase based on chromogenic beta-lactamase assay | Imipenem MIC | Beta-lactamase Profile |
|---|---|---|---|
| 1 | no | <=2 | K1-high |
| 2 | no | <=2 | OSBL, K1-high |
| 3 | yes | >16 | OSBL, K1-high, Carb |
| 4 | no | <=2 | WT |

WT means wild-type or without beta-lactamase.
Carb means carbapenemase.
K1-high means high level of K1 beta-lactamase.
OSBL means original-spectrum beta-lactamase.

5.2 Detection of a Metallo-Beta-Lactamase

This example demonstrates that compositions comprising a detectable beta-lactamase substrate and one or more beta-lactamase inhibitors may be used to detect the presence of a metallo-beta-lactamase in a sample.

5.2.1 Materials & Methods

Chromogenic Beta-Lactamase Assay

Representative *Klebsiella pneumoniae* strains were each streaked on a Trypticase™ Soy Agar with 5% Sheep Blood agar plate and the plate was incubated at 35° C. for 18 hours. Afterwards, a sample of *Klebsiella pneumoniae* from each plate was added to 1 ml of sterile water in a BD 2054 Falcon tube to a turbidity of about 1.6 as measured by a Microscan turbidity reader. 50 µl of a cell suspension was added to each of the following 150 µl compositions to bring the final concentration in each composition to be the following (i) Composition 1 comprising 50 µM of nitrocefin, 2.5 mM of cloxacillin, and 50 mM phosphate buffer pH 7.0; (ii) Composition 2 comprising 50 µM of nitrocefin, 2.5 mM of cloxacillin, 1 mM of clavulanic acid and 50 mM phosphate buffer pH 7.0; and (iii) Composition 3 comprising 50 µM of nitrocefin, 2.5 mM of cloxacillin, 1 mM of clavulanic acid, DEDTC at a concentration of 5 mM or 15 mM, DPC at a concentration of 1.5 mM or 4.5 mM or TPEN at a concentration of 9 mM and 50 mM phosphate buffer pH 7.0. The color of the nitrocefin after 30 minutes or 1 hour was assessed visually. The hydrolysis of nitrocefin by a beta-lactamase causes the color of the composition to change from yellow to red.

Imipenem MIC Assay

Imipenem MIC Assay were performed by microbroth dilution method according to the CLSI (Clinical and Laboratory Standards Institute) standard.

5.2.2 Results

The results of a chromogenic beta-lactamase assay for representative *Klebsiella pneumoniae* strains are summarized in Table 13, below. In the assay, the affect of two different metal chelators at two different concentrations was assessed. Each composition was incubated for 30 minutes with a representative strain before the results of the assay were assessed by visual inspection. Table 14, below, compares the conclusions based on the chromogenic beta-lactamase assay described herein to the results obtained by the imipenem MIC assay, and the beta-lactamase profile determined previously by isoelectric focusing (IEF) and PCR testing for the same *Klebsiella pneumoniae* strains in Table 13. The conclusions based on the chromogenic beta-lactamase assay results are consistent with the conclusions based upon the imipenem MIC, IEF and PCR results for the detection of the presence of a metallo-beta-lactamase in a sample.

TABLE 13

|   | Comp. #1 Utilization of nitrocefin | Comp. #2 Utilization of nitrocefin | Comp. #3 (5 mM DEDTC) Utilization of nitrocefin | Comp. #3 (15 mM DEDTC) Utilization of nitrocefin | Comp. #3 (1.5 mM DPC) Utilization of nitrocefin | Comp. #3 (4.5 mM DPC) Utilization of nitrocefin | Presence of MBL based on Chromogenic Assay |
|---|---|---|---|---|---|---|---|
| 1 | + | + | reduced + | − | − | − | Yes |
| 2 | − | − | − | − | − | − | No |
| 3 | + | + | + | + | + | + | No |
| 4 | + | − | − | − | − | − | No |

TABLE 14

|   | Organism | Imipenem MIC | beta-lactamase profile | Conclusion from Chromogenic Beta-Lactamase Assay |
|---|---|---|---|---|
| 1 | KLEPNEP | =4 | ESBL, MBL | MBL |
| 2 | KLEPNEP | <=2 | WT | WT |
| 3 | KLEPNEP | >16 | OSBL, Carbapenemase | serine carbapenemase |
| 4 | KLEPNEP | <=2 | ESBL, C-plasmid | Beta-lactamase but not carbapenemase |

MBL means metallo-beta-lactamase.
WT means wild-type or without beta-lactamase.
Bold letters indicate the presence of a metallo-beta-lactamase or a serine carbapenemase which is consistent with the conclusion from the chromogenic beta-lactamase assay.

The results of a chromogenic beta-lactamase assay for representative *Klebsiella pneumoniae* (KLEPNEP) and *Pseudomonas aeruginosa* (PSEAER) strains are summarized in Table 15, below. In the assay, the affect of two different metal chelators was assessed. Each composition was incubated for 60 minutes with a representative strain before the results of the assay were assessed by visual inspection. Table 16, below, compares the conclusions based on the beta-lactamase assay described herein to the results obtained by the imipenem MIC assay, and the beta-lactamase profile determined previously by isoelectric focusing (IEF) and PCR testing for the same bacterial strains in Table 15. The conclusions based on the chromogenic beta-lactamase assay results are consistent with the conclusions based upon the Imipenem MIC, IEF and PCR results for the detection of the presence of a metallo-beta-lactamase or a serine carbapenemase in a sample.

Cefoxitin MIC Assay

Cefoxitin MIC Assay were performed by microbroth dilution method according to the CLSI (Clinical and Laboratory Standards Institute) standard.

5.3.2 Results

The results of a chromogenic beta-lactamase assay for representative *E. coli* strains are summarized in Table 17, below. Table 18, below, compares the conclusions based on

TABLE 15

| | Organism | Comp. #1 Utilization of nitrocefin | Comp. #2 Utilization of nitrocefin | Comp. #3 (4.5 mM DPC) Utilization of nitrocefin | Comp. #3 (15 mM DEDTC) Utilization of nitrocefin | Comp. #3 (9 mM TPEN) Utilization of nitrocefin | Presence of MBL based on Chromogenic Assay |
|---|---|---|---|---|---|---|---|
| 1 | KLEPNEP | + | + | − | − | reduced + | Yes |
| 2 | KLEPNEP | + | + | − | − | − | Yes |
| 3 | KLEPNEP | + | + | + | + | + | No |
| 4 | KLEPNEP | + | − | − | − | reduced + | No |
| 5 | KLEPENEP | − | − | − | − | − | No |
| 6 | PSEAER | + | + | − | − | reduced + | Yes |

TABLE 16

| | Organism | Imipenem MIC | Beta-lactamase profile | Conclusion from chromogenic beta-lactamase assay |
|---|---|---|---|---|
| 1 | KLEPNEP | 4 | ESBL, MBL | MBL |
| 2 | KLEPNEP | >16 | MBL | MBL |
| 3 | KLEPNEP | =8 | ESBL, Carbapenemase | Class A serine carbapenemase |
| 4 | KLEPNEP | <=2 | ESBL, C-plasmid | Beta-lactamase but not carbapenemase |
| 5 | KLEPENEP | <=2 | WT | WT or no beta-lacatamase |
| 6 | PSEAER | >16 | MBL | MBL |

WT means wild-type.
MBL means metallo-beta-lactamase.
C-plasmid means a plasmid-borne AmpC beta-lactamase.
Bold letters indicate the presence of a metallo-beta-lactamase or a serine carbapenemase which is consistent with the conclusion from the chromogenic beta-lactamase assay 5.3 Detection of an AmpC Beta-Lactamase This example demonstrates that compositions comprising a detectable beta-lactamase substrate and one or more beta-lactamase inhibitors may be used to detect the presence of an AmpC.

5.3.1 Materials & Methods

Chromogenic Beta-Lactamase Assay

Representative *E. coli* strains were each streaked on a Trypticase™ Soy Agar with 5% Sheep Blood agar plate and the plate was incubated at 35° C. for 18 hours. Afterwards, a sample of *E. coli* from each plate was added to 1 ml of sterile water in a BD 2054 Falcon tube to a turbidity of about 1.6 as measured by a Microscan turbidity reader. 50 µl of a cell suspension was added to each of the following 150 µl compositions to bring the concentration in each composition to be the following: (i) Composition 1 comprising 50 µM of nitrocefin and 50 mM of phosphate buffer pH 7.0; (ii) Composition 2 comprising 50 µM of nitrocefin 5 mM of cloxacillin, and 50 mM of phosphate buffer pH 7.0; (iii) Composition 3 comprising 50 µM of nitrocefin, 1 mM of clavulanic acid and 50 mM of phosphate buffer pH 7.0; and (iv) Composition 4 comprising 50 µM of nitrocefin, 5 mM of cloxacillin, 1 mM of clavulanic acid and 50 mM of phosphate buffer pH 7.0. The color of the nitrocefin after 60 minutes was assessed visually. The hydrolysis of nitrocefin by a beta-lactamase causes the color of the composition to change from yellow to red.

the beta-lactamase assay described herein to the results obtained by the cefoxitin MIC assay and the beta-lactamase profile determined previously by isoelectric focusing (IEF) and PCR testing using the same *E. coli* strains in Table 17. The conclusions based on the chromogenic beta-lactamase assay results are consistent with the conclusions based upon the cefoxitin MIC, IEF and PCR results for the detection of the presence of an AmpC in a sample.

TABLE 17

| | Comp. #1 | Comp. #2 | Comp. #3 | Comp. #4 | Conclusion based on Chromogenic Assay |
|---|---|---|---|---|---|
| 1 | − | − | − | − | WT |
| 2 | + | + | + | − | AmpC, OSBL or AmpC, ESBL |
| 3 | + | − | + | − | AmpC |
| 4 | + | − | − | − | OSBL or ESBL |
| 5 | + | + | + | − | AmpC, OSBL or AmpC, ESBL |
| 6 | + | + | − | − | OSBL or ESBL |
| 7 | + | Reduced + | − | − | OSBL or ESBL |
| 8 | + | − | + | − | AmpC |
| 9 | + | + | + | + | carbapenemase |
| 10 | + | − | + | − | AmpC |
| 11 | + | + | + | − | AmpC, OSBL or AmpC, ESBL |

WT means wild-type or no beta-lactamase.
OSBL means original-spectrum beta-lactamase.
ESBL means extended-spectrum beta-lactamase.
AmpC means AmpC beta-lactamase either plasmid-borne or chromosomal.

TABLE 18

| | Cefoxitin MIC | Conclusion based on reference methods | Conclusion based on chromogenic beta-lactamase assay |
|---|---|---|---|
| 1 | <=4 | WT | No detectable β-lactamase |
| 2 | >32 | OSBL, C-plasmid | AmpC, OSBL or AmpC, ESBL |
| 3 | >32 | OSBL, C-chromo | AmpC |
| 4 | 32 | OSBL | ESBL or OSBL |
| 5 | >32 | ESBL, C-plasmid | AmpC, OSBL or AmpC, ESBL |

TABLE 18-continued

| Cefoxitin MIC | Conclusion based on reference methods | Conclusion based on chromogenic beta-lactamase assay |
|---|---|---|
| 6 | =32 | ESBL, C-chromo | ESBL or OSBL |
| 7 | =8 | ESBL | ESBL or OSBL |
| 8 | >32 | C-chromo | AmpC |
| 9 | >32 | Carbapenemase | Carbapenemase |
| 10 | >32 | C-plasmid | AmpC |
| 11 | >32 | OSBL, C-plasmid | AmpC, OSBL or AmpC, ESBL |

WT means wild-type or beta-lactamase.
OSBL means original-spectrum beta-lactamase.
ESBL means extended-spectrum beta-lactamase.
AmpC means an AmpC beta-lactamase that is either plasmid-borne or chromosomal.
C-plasmid means plasmid-borne.

5.4 Detection of an ESBL

This example demonstrates that compositions comprising a detectable beta-lactamase substrate and one or more beta-lactamase inhibitors may be used to detect the presence of an ESBL.

5.4.1 Materials & Methods

Chromogenic Beta-Lactamase Assay

Representative E. coli and Klebsiella pneumoniae strains from BD collection were each streaked on a Trypticase™ Soy Agar with 5% Sheep Blood agar plate and the plate was incubated at 35° C. for 18 hours. Afterwards, a sample of E. coli or Klebsiella pneumoniae from each plate was added to 1 ml of sterile water in a BD 2054 Falcon tube to a desired turbidity (reading 1.5 for sample 2-5, 8-10, reading 1.0 for sample 1-2 and reading 0.5 for sample 6-7) as measured by a Microscan turbidity reader. 50 µl of a cell suspension was added to each of the following 1500 compositions to bring the final concentration in each composition to be the following: (i) Composition 1 comprising 50 µM of nitrocefin and 50 mM of phosphate buffer pH 7.0; (ii) Composition 2 comprising 50 µM of nitrocefin, 0.1 mM of clavulanic acid, and 50 mM of phosphate buffer pH 7.0; (iii) Composition 3 comprising 50 µM of nitrocefin, 25 mM of cefotaxime and 50 mM of phosphate buffer pH 7.0; and (iv) Composition 4 comprising 50 µM of nitrocefin, 1.25 mM of ceftriaxone (Toku-E, Japan) and 50 mM of phosphate buffer pH 7.0. The color of the nitrocefin after 20 minutes or 60 minutes was assessed visually. The hydrolysis of nitrocefin by a beta-lactamase causes the color of the composition to change from yellow to red.

MIC Assays

MIC Assays of CTX (cefotaxime), CAZ (cefotaxime/clavulanic acid), CAZ (ceftazidime) and CCZ (ceftazidime/clavulanic acid) were performed by microbroth dilution method according to the CLSI (Clinical and Laboratory Standards Institute) standard.

5.4.2 Results

The results of a chromogenic beta-lactamase assay for representative E. coli (ESCCOL) and Klebsiella pneumoniae (KLEPNEP) strains are summarized in Table 19, below. Table 20, below, compares the conclusions based on the beta-lactamase assay described herein to the results obtained by the cefoxitin MIC assay and the beta-lactamase profile determined previously by isoelectric focusing (IEF) and PCR testing using the same strains in Table 19. The conclusions based on the chromogenic beta-lactamase assay results are consistent with the conclusions based upon the cefoxitin MIC, IEF and PCR results for the detection of the presence of an ESBL in a sample.

TABLE 19

| Organism | Comp. #1 | Comp. #2 | Comp. #3 | Comp. #4 | Conclusion |
|---|---|---|---|---|---|
| 1 ESCCOL | + | − | − | − | ESBL |
| 2 ESCCOL | + | − | − | − | ESBL |
| 3 ESCCOL | + | − | + | + | OSBL |
| 4 ESCCOL | + | − | + | + | OSBL |
| 5 ESCCOL | − | − | − | − | WT |
| 6 KLEPNEP | + | − | reduced + | reduced + | ESBL |
| 7 KLEPNEP | + | − | − | − | ESBL |
| 8 KLEPNEP | + | − | + | − | OSBL |
| 9 KLEPNEP | + | − | + | + | OSBL |
| 10 KLEPNEP | − | − | − | − | WT |

WT means wild-type or without beta-lactamase.
ESBL means extended-spectrum beta-lactamase.
OSBL means original-spectrum beta-lactamase.

TABLE 20

| Organism | CTX MIC, µg/ml | CCX MIC, µg/ml | CAZ MIC, µg/ml | CCZ MIC, µg/ml | Conclusion based on reference methods | Conclusion based on chromogenic beta-lactamase assay |
|---|---|---|---|---|---|---|
| 1 ESCCOL | =32 | <=0.25 | >128 | <=0.25 | ESBL | ESBL |
| 2 ESCCOL | >64 | <=0.25 | 16 | <=0.25 | ESBL | ESBL |
| 3 ESCCOL | <=0.25 | <=0.25 | <=0.25 | <=0.25 | OSBL | OSBL |
| 4 ESCCOL | <=0.25 | <=0.25 | <=0.25 | <=0.25 | OSBL | OSBL |
| 5 ESCCOL | <=0.25 | <=0.25 | <=0.25 | <=0.25 | WT | WT |
| 6 KLEPNEP | >64 | <=0.25 | >128 | =4 | ESBL | ESBL |
| 7 KLEPNEP | >64 | <=0.25 | =8 | <=0.25 | ESBL | ESBL |
| 8 KLEPNEP | <=0.25 | <=0.25 | <=0.25 | <=0.25 | OSBL | OSBL |
| 9 KLEPNEP | <=0.25 | <=0.25 | <=0.25 | <=0.25 | OSBL | OSBL |
| 10 KLEPNEP | =0.5 | =0.5 | <=0.25 | <=0.25 | WT | WT |

WT means wild-type or without beta-lactamase.
OSBL means original-spectrum beta-lactamase.
ESBL means extended-spectrum beta-lactamase.
Bold letters indicate the presence of an ESBL, which is consistent with the conclusion from the chromogenic beta-lactamase assay.
Note that assay for sample 6 was finished at 20 minutes and the rest samples finish at 1 hour.

5.5 Detection of Beta-Lactamases in the Presence of Lysis Reagents

This example demonstrates that the in situ lysis of bacterial cells and the detection of beta-lactamases provides a high level of sensitivity of the beta-lactamase assay, which can be particularly advantageous when detecting certain beta-lactamases expressed by certain types of bacteria (e.g., gram negative bacteria).

5.5.1 Materials and Methods

Panel Production.

Stock solutions with nitrocefin, trehalose, and/or reagents used to lyse the bacterial cells in pH6 MES buffer were prepared and dispensed into wells on the bottom part of Phoenix™ panel (BD. USA), with one stock solution in one well. Panels were then dried in an oven for approximately 30 min at approximately 70° C. The top part of Phoenix panel was then attached to the bottom part forming a panel system ready for inoculation. The concentrations of reagents after rehydration following Phoenix panel inoculation were 3 mg/ml lysozyme, 1 mM EDTA, and 1% trehalose in 0.1M pH6 MES buffer.

Inoculation and Lysis Testing.

Representative strains of bacteria, such as *E. coli* and *Klebsiella pneumoniae*, were each streaked on a Trypticase™ Soy Agar with 5% Sheep Blood agar plate (BD, USA) and the plates were incubated at 35° C. for 18 hours. Afterwards, colonies from pure culture on each plate were inoculated into BD Phoenix ID broth (BD, USA) and adjusted to a desired turbidity of approximately 0.5 MacFarland. The bacterial cell suspension was then poured into the ID side of the Phoenix panels that were specifically made for cell lysis testing. Once inoculated, the panel was loaded into Phoenix instrument, where nitrocefin hydrolysis rate was monitored by colorimetric signals changes every 20 minutes for 16 hours.

Microorganism.

The presence of beta-lactamase in the strains tested herein was previously characterized by isoelectric focusing (IEF) gel electrophoresis, PCR testing, or MIC assays, which were performed by microbroth dilution method according to the CLSI (Clinical and Laboratory Standards Institute) standard.

5.5.2 Results

As shown in Table 21, below, some strains that harbor intracellular beta-lactamase have relatively low nitrocefin activity (<=4 within 10 hrs on Phoenix panel) in the absence of lysis reagents. The addition of lysis reagents in Phoenix wells significantly improved the nitrocefin hydrolysis rate by those cells. Some strains exhibited relatively high nitrocefin activity (>4 within 10 hrs on Phoenix panel) in the absence of lysis reagents. With respect to those strains, the presence of lysis reagents did not result in a change or only resulted in a slight improvement in the nitrocefin activity. The lysis reagents did not inhibit the nitrofecin activity of the beta-lactamases expressed by the bacterial strains. Neither lysozyme nor EDTA, alone or in combination, hydrolyzed nitrocefin. Without being bound by any theory, it is believed that the improvement in the nitrocefin hydrolysis rate is primarily because more beta-lactamase is released from periplasmic space, and thus, more beta-lactamase is accessible to its substrate, nitrocefin.

TABLE 21

| Sample | Organism | Presence of intracellular beta-lactamase | NCF activity | NCF activity with lysis reagent |
|---|---|---|---|---|
| 1 | E. coli | + | 1.9 | 7.2 |
| 2 | E. coli | + | 2.1 | 7.7 |
| 3 | E. coli | + | 2.3 | 8.1 |
| 4 | E. coli | + | 1.9 | 6.8 |
| 5 | E. coli | + | 8.2 | 9.1 |
| 6 | E. coli | + | 7.2 | 8.1 |

TABLE 21-continued

| Sample | Organism | Presence of intracellular beta-lactamase | NCF activity | NCF activity with lysis reagent |
|---|---|---|---|---|
| 7 | E. coli | + | 6.8 | 8.4 |
| 8 | E. coli | − | 1.7 | 1.8 |
| 9 | Klebsiella pneumoniae | + | 1.3 | 4.6 |
| 10 | Klebsiella pneumoniae | + | 3.3 | 6.3 |
| 11 | Klebsiella pneumoniae | + | 3.9 | 6.1 |
| 12 | Klebsiella pneumoniae | + | 2.6 | 5.6 |
| 13 | Klebsiella pneumoniae | + | 6.7 | 6.8 |
| 14 | Klebsiella pneumoniae | + | 7.5 | 8.8 |
| 15 | Klebsiella pneumoniae | + | 9.1 | 9.5 |
| 16 | Klebsiella pneumoniae | − | 1.2 | 1.8 |

NCF activity, the value shown is the maximum nitrocefin hydrolysis rate within 10 hrs following Phoenix panel loading into the instrument. The unit of activity is calculated based on Phoenix signals.

Equivalents

Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference.

Citation or discussion of a reference herein shall not be construed as an admission that such is prior art to the present invention.

What is claimed:

1. A kit for detecting the presence of a beta-lactamase, comprising, in one or more containers:
    (a) a first composition comprising a detectable beta-lactamase substrate and an AmpC inhibitor; and
    (b) a second composition comprising a detectable beta-lactamase substrate, an AmpC inhibitor, and a serine beta-lactamase inhibitor in an amount sufficient to inhibit an extended-spectrum beta-lactamase (ESBL) and an original-spectrum beta-lactamase (OSBL) but not a class A serine carbapenemase.

2. A kit for detecting the presence of a beta-lactamase, comprising, in one or more containers:
    (a) a first composition comprising a detectable beta-lactamase substrate and an AmpC inhibitor;
    (b) a second composition comprising a detectable beta-lactamase substrate, an AmpC inhibitor, and a serine beta-lactamase inhibitor in an amount sufficient to inhibit an ESBL and an OSBL but not a class A serine carbapenemase; and
    (c) a third composition comprising a detectable beta-lactamase substrate, an AmpC inhibitor, a serine beta-lactamase inhibitor in amount sufficient to inhibit an ESBL and an OSBL but not a class A serine carbapenemase, and a metal chelator.

3. The kit of claim 2 further comprising a fourth composition comprising a detectable beta-lactamase substrate and a serine beta-lactamase inhibitor in an amount sufficient to inhibit an ESBL and an OSBL but not a class A serine carbapenemase.

4. A kit for detecting the presence of a beta-lactamase, comprising, in one or more containers:
   (a) a first composition comprising a detectable beta-lactamase substrate and an AmpC inhibitor;
   (b) a second composition comprising a detectable beta-lactamase substrate, an AmpC inhibitor, and a serine beta-lactamase inhibitor in an amount sufficient to inhibit an ESBL and an OSBL but not a class A serine carbapenemase; and
   (c) a third composition comprising a detectable beta-lactamase substrate and a serine beta-lactamase inhibitor in an amount sufficient to inhibit an ESBL and an OSBL but not a class A serine carbapenemase.

5. The kit of claim 1 further comprising a third composition comprising a detectable beta-lactamase substrate and an ESBL inhibitor.

6. The kit of claim 3 further comprising a fifth composition comprising a detectable beta-lactamase substrate and an ESBL inhibitor.

7. The kit of claim 1, 2 or 4, wherein the detectable beta-lactamase substrate is nitrocefin, pyridinium-2-azo-p-dimethylaniline chromophore, (7R)-3-(((3-carboxy-4-nitrophenyl)thio)methyl)-8-oxo-7-(2-(thiophen-2-yl)acetamido)-5-thia-1-azabicyclo[4.2.0]oct-2-ene-2-carboxylic acid, or (7R)-7[2-aminothiazol-4-yl]-(z)-2-(1-carboxy-1-methylethoxyimino)acetamido)-3-(2,4-dinitrostyryl)-3-cephem-4-carboxylic acid trifluoroacetate, E-isomer.

8. The kit of claim 1, 2 or 4, wherein the AmpC inhibitor is cloxacillin, a salt form of cloxacillin, (2S,3S)-3-(((Z)-2-(((1,5-dihydroxy-4-oxo-1,4-dihydropyridin-2-yl)methoxy)imino)-2-(thiophen-2-yl)ethyl)amino)-2-methyl-4-oxoazetidine-1-sulfonic acid, boronic acid, or a boronic acid derivative.

9. The kit of claim 1, 2 or 4, wherein the serine beta-lactamase inhibitor is clavulanic acid, tazobactum, sulbactam, or a salt form thereof.

10. The kit of claim 5 or 6, wherein the ESBL inhibitor is cefotaxime, ceftazidime, or a salt form thereof.

11. The kit of claim 2, wherein the metal chelator is dipicolinic acid (DPC), diethyl dithiocarbamate (DEDTC), N,N,N',N'-tetrakis-(2-pyridylmethyl)-ethylenediamine (TPEN), Ethylenediaminetetraacetic acid (EDTA), 2,3-dimercapto-1-propane sulfonic acid (DMPS) or 1,10-phenathroline.

12. The kit of claim 1, 2 or 4, wherein each composition comprises a lysis reagent.

13. The kit of claim 1, 2 or 4, wherein each composition comprises a lysis reagent and an agent that promotes the stabilization of the lysis reagent.

14. The kit of claim 1, 2 or 4, wherein each composition comprises a lysis reagent, an agent that promotes the stabilization of the lysis reagent and an agent that enhances the lysis of a bacterial cell by a lysis reagent.

15. The kit of claim 1, 2 or 4, wherein each composition comprises lysozyme and trehalose.

16. The kit of claim 1, 2 or 4, wherein each composition comprises lysozyme, trehalose and EDTA.

17. The kit of claim 1, 2 or 4, wherein each composition is dried and present on or in a different solid support.

18. The kit of claim 12, wherein each composition is dried and present on or in a different solid support.

19. The kit of claim 13, wherein each composition is dried and present on or in a different solid support.

20. The kit of claim 14, wherein each composition is dried and present on or in a different solid support.

* * * * *